(12) United States Patent
Chilkoti et al.

(10) Patent No.: US 11,467,156 B2
(45) Date of Patent: Oct. 11, 2022

(54) NONFOULING BIOSENSORS

(71) Applicant: Duke University, Durham, NC (US)

(72) Inventors: Ashutosh Chilkoti, Durham, NC (US);
Aaron Franklin, Durham, NC (US);
Benjamin Yellen, Durham, NC (US);
Angus Hucknall, Durham, NC (US);
Daniel Joh, Durham, NC (US);
Roozbeh Abedini-Nassab, Durham, NC (US); Joseph Andrews, Durham, NC (US)

(73) Assignee: Duke University, Durham, NC (US)

( * ) Notice: Subject to any disclaimer, the term of this patent is extended or adjusted under 35 U.S.C. 154(b) by 47 days.

(21) Appl. No.: 16/305,696

(22) PCT Filed: Jun. 1, 2017

(86) PCT No.: PCT/US2017/035530
§ 371 (c)(1),
(2) Date: Nov. 29, 2018

(87) PCT Pub. No.: WO2017/210476
PCT Pub. Date: Dec. 7, 2017

(65) Prior Publication Data
US 2020/0378916 A1 Dec. 3, 2020

Related U.S. Application Data

(60) Provisional application No. 62/414,877, filed on Oct. 31, 2016, provisional application No. 62/343,926, filed on Jun. 1, 2016.

(51) Int. Cl.
*G01N 33/543* (2006.01)
*G01N 27/12* (2006.01)
(Continued)

(52) U.S. Cl.
CPC ..... *G01N 33/54373* (2013.01); *G01N 27/126* (2013.01); *G01N 27/227* (2013.01);
(Continued)

(58) Field of Classification Search
CPC ......... G01N 27/4146; G01N 33/54373; G01N 27/126
See application file for complete search history.

(56) References Cited

U.S. PATENT DOCUMENTS 4,415,732 A  11/1983 Caruthers et al.
4,458,066 A  7/1984 Caruthers et al.
(Continued)

FOREIGN PATENT DOCUMENTS

AU  2007265628 B2  12/2012
CA     2327325 A1  11/1999
(Continued)

OTHER PUBLICATIONS

Hess et al., Graphene Transistors for Multifunctional Polymer Brushes for Biosensing Applications, Applied Materials & Interfaces, vol. 6, pp. 9705-9710. (Year: 2014).*
(Continued)

*Primary Examiner* — Melanie Brown
(74) *Attorney, Agent, or Firm* — Michael Best & Friedrich LLP

(57) ABSTRACT

Disclosed are sensors that include a carbon nanotube channel and a non-fouling polymer layer, where the non-fouling polymer layer and the carbon nanotube channel do not directly contact each other and are separated by a dielectric layer. The disclosed sensors may be used, e.g., as biosensors for the accurate and sensitive detection of analytes within a sample. Also disclosed are methods of making and using the sensors.

21 Claims, 42 Drawing Sheets

(51) Int. Cl.
*G01N 27/22* (2006.01)
*G01N 27/414* (2006.01)

(52) U.S. Cl.
CPC ..... *G01N 27/4146* (2013.01); *G01N 33/5438* (2013.01); *G01N 27/127* (2013.01)

(56) References Cited

U.S. PATENT DOCUMENTS

| | | |
|---|---|---|
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Feigner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Feigner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,179 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 1/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1* | 9/2004 | Snow ................ H01L 51/0048 438/800 |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1* | 7/2011 | Ah ................ B01L 3/502761 435/5 |
| 2011/0207673 A1 | 8/2011 | Chilkoti et al. |
| 2011/0248698 A1* | 10/2011 | Kikuchi ............ G01N 27/4145 324/76.11 |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2014/0326600 A1* | 11/2014 | Li ................ B82Y 40/00 204/403.14 |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1* | 7/2016 | Herget ............... G01N 27/4145 |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |

(56) References Cited

U.S. PATENT DOCUMENTS

| | | | |
|---|---|---|---|
| 2016/0348147 A1 | 12/2016 | Lopez et al. | |
| 2016/0355802 A1 | 12/2016 | Isaacs et al. | |
| 2017/0088670 A1 | 3/2017 | Rowan et al. | |
| 2017/0102357 A1* | 4/2017 | Liang | H01L 29/7781 |
| 2017/0166621 A1 | 6/2017 | Boettcher et al. | |
| 2017/0170142 A1 | 6/2017 | Edelstein et al. | |
| 2017/0189545 A1 | 7/2017 | Lee et al. | |
| 2017/0233714 A1 | 8/2017 | Chilkoti et al. | |
| 2017/0239363 A1 | 8/2017 | Chilkoti et al. | |
| 2017/0369651 A1 | 12/2017 | Cheng et al. | |
| 2018/0037609 A1 | 2/2018 | Chilkoti et al. | |
| 2018/0135060 A1 | 5/2018 | Romero Ramos et al. | |
| 2018/0161772 A1 | 6/2018 | Rammohan et al. | |
| 2018/0171337 A1 | 6/2018 | O'Neill et al. | |
| 2018/0200196 A1 | 7/2018 | Fahmy et al. | |
| 2018/0217136 A1 | 8/2018 | Chilkoti et al. | |
| 2018/0231469 A1 | 8/2018 | Gibbons et al. | |
| 2018/0238864 A1 | 8/2018 | Burd et al. | |
| 2018/0258157 A1 | 9/2018 | Chilkoti et al. | |
| 2018/0326044 A1 | 11/2018 | Carter | |
| 2018/0327752 A1 | 11/2018 | Pillay et al. | |
| 2019/0016763 A1 | 1/2019 | Kitazawa et al. | |
| 2019/0204309 A1 | 7/2019 | Gibbs | |
| 2019/0285623 A1 | 9/2019 | Chilkoti et al. | |
| 2019/0292549 A1 | 9/2019 | Zhang et al. | |
| 2019/0345228 A1 | 11/2019 | Chilkoti et al. | |
| 2020/0078313 A1 | 3/2020 | Roy et al. | |
| 2020/0121809 A1 | 4/2020 | Hope et al. | |
| 2020/0148724 A1 | 5/2020 | Chilkoti et al. | |
| 2020/0163878 A1 | 5/2020 | Baumhof et al. | |
| 2020/0181555 A1 | 6/2020 | Hinojosa et al. | |
| 2021/0154143 A1 | 5/2021 | Chilkoti et al. | |

FOREIGN PATENT DOCUMENTS

| | | |
|---|---|---|
| CA | 2423488 A1 | 4/2002 |
| CN | 104725628 B | 4/2018 |
| EP | 2664340 B1 | 6/2006 |
| EP | 1670315 B1 | 4/2017 |
| JP | 2014-156428 A | 8/2014 |
| JP | 2014-534265 A | 12/2014 |
| WO | WO1991/019813 A1 | 12/1991 |
| WO | WO 2003/040165 A2 | 10/2002 |
| WO | WO 2004/096124 A2 | 11/2004 |
| WO | WO 2006/004778 A2 | 1/2006 |
| WO | WO2006/110292 A2 | 10/2006 |
| WO | WO 2007/073486 A2 | 6/2007 |
| WO | WO 2007/108013 A2 | 9/2007 |
| WO | WO 2007/134245 A2 | 11/2007 |
| WO | 2008/012543 A1 | 1/2008 |
| WO | 2008/030968 A2 | 3/2008 |
| WO | WO 2009/067584 A1 | 5/2009 |
| WO | WO 2010/054699 A1 | 5/2010 |
| WO | WO 2010/057154 A1 | 5/2010 |
| WO | WO 2010/096422 A1 | 8/2010 |
| WO | 2011/025572 A1 | 3/2011 |
| WO | WO 2011/123813 A2 | 10/2011 |
| WO | WO2012/162426 A1 | 11/2012 |
| WO | WO2013/049234 A2 | 4/2013 |
| WO | WO 2013/065009 A1 | 5/2013 |
| WO | 2013/106715 A1 | 7/2013 |
| WO | WO2014/037373 A1 | 3/2014 |
| WO | WO 2014/194244 A1 | 12/2014 |
| WO | WO2015/011231 A1 | 1/2015 |
| WO | WO 2015/130846 A2 | 9/2015 |
| WO | 2016/065300 A1 | 4/2016 |
| WO | WO 2016/065273 A1 | 4/2016 |
| WO | WO 2016/090103 A1 | 6/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |
| WO | 2017/192449 A1 | 11/2017 |
| WO | WO2018/115401 A1 | 6/2018 |
| WO | WO 2018/144854 A1 | 8/2018 |
| WO | 2019/103744 A2 | 5/2019 |
| WO | 2019/147954 A1 | 8/2019 |
| WO | WO2020/037214 A1 | 2/2020 |
| WO | 2020/160472 A1 | 8/2020 |

OTHER PUBLICATIONS

Hwang et al., Synthesis and Characterization of Polystyrene Brushes for Organic Thin Film Transistors, Journal of Nanoscience and Nanotechnology, vol. 12, pp. 4137-4141. (Year: 2012).*

Park et al., Polymer Brush as a Facile Dielectric Surface Treatment for High-Performance, Stable, Soluble Acene-Based Transistors, Chemistry of Materials, vol. 22, pp. 5377-5382. (Year: 2010).*

United States Patent Office Notice of Allowance for U.S. Appl. No. 15/387,536 dated Mar. 13, 2019 (13 pages).

United States Patent Office Notice of Allowance for U.S. Appl. No. 15/561,799 dated Apr. 2, 2019 (6 pages).

United States Patent Office Notice of Allowance for U.S. Appl. No. 15/387,540 dated Apr. 17, 2019 (9 pages).

Park et al., "Protein stitchery: Design of a protein for selective binding to a specific DNA sequence," PNAS, 1992, vol. 89:9094-9096.

Olafsen et al., "Covalent disulfide-linked anti-CEA diabody allows site-specific conjugation and radiolabeling for tumor targeting applications," Protein Engineering, Design & Selection, 2004, 17(1):21-27.

Hu et al., "Nanografting De Novo Proteins onto Gold Surfaces," Langmuir, 2005, vol. 21:9103-9109.

McDaniel, "Assembly of Highly Asymmetric Genetically-Encoded Amphiphiles for Thermally Targeted Delivery of Therapeutics," Dissertation, 2013, 295 pages.

International Search Report and Written Opinion for Application No. PCT/US2019/044911 dated Dec. 10, 2019 11 pages).

International Search Report and Written Opinion for Application No. PCT/US2019/050077 dated Jan. 27, 2020 (19 pages).

United States Patent Office Action for U.S. Appl. No. 16/058,924 dated Nov. 26, 2019 (23 pages).

Chockalingam et al., "Design and application of stimulus-responsive peptide systems," Protein Engineering, Design & Selection, 2007, 20(4):155-161.

United States Patent Office Action for U.S. Appl. No. 16/335,734 dated Nov. 20, 2020 (15 pages).

United States Patent Office Action for U.S. Appl. No. 16/525,374 dated Dec. 7, 2020 (9 pages).

Alarcon et al., "Exendin 4 controls insulin production in rat islet beta cells predominantly by potentiation of glucose-stimulated proinsulin biosynthesis at the translational level," Diabetologia, 2006, 49(12):2920-2929.

American Diabetes Association (2018) Standards of medical care in diabetes—2018. Diabetes Care 41(Suppl 1):S1-S159.

Arner et al., "FGF21 attenuates lipolysis in human adipocytes—a possible link to improved insulin sensitivity," FEBS Lett, 2008, 582(12):1725-1730.

Badi, "Non-linear PEG-based thermoresponsive polymer systems," Progress in Polymer Science, 2017, 66, 54-79.

Baggio et al., "Biology of Incretins: GLP-1 and GIP," Gastroenterology, 2007, 132(6):2131-2157.

Beenken et al., "The FGF family: biology, pathophysiology and therapy," Nat Rev Drug Discov, 2009, 8(3):235-253.

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, 2017, 27(12):1-9.

Bobo et al., "Nanoparticle-based medicines: a review of FDA-approved materials and clinical trials to date." Pharmaceutical research 33.10 (2016): 2373-2387.

Buteau et al., "Glucagon-like peptide-1 prevents beta cell glucolipotoxicity," Diabetologia, 2004, 47(5):806-815.

Butler et al., "β-Cell Deficit and Increased β-Cell Apoptosis in Humans With Type 2 Diabetes," Diabetes, 2003, 52(1):102-110.

(56) References Cited

OTHER PUBLICATIONS

Cabrera et al., "Automated, High-Throughput Assays for Evaluation of Human Pancreatic Islet Function," Cell Transplant, 2008, 16(10):1039-1048.
Cabrera et al., "Glutamate Is a Positive Autocrine Signal for Glucagon Release," Cell Metab, 2008, 7(6):545-554.
Centers for Disease Control and Prevention (2017) National Diabetes Statistics Report, 2017. ed U.S. Dept of Health and Human Services (Atlanta).
Chatterjee et al., "Type 2 diabetes," The Lancet, 2017, 389(10085): 2239-2251.
Chilkoti et al., "Stimulus responsive elastin biopolymers: applications in medicine and biotechnology," Curr Opin Chem Biol, 2006, 10(6):652-657.
Coskun et al., "Fibroblast Growth Factor 21 Corrects Obesity in Mice," Endocrinology, 2008, 149(12):6018-6027.
Day et al., "A new glucagon and GLP-1 co-agonist eliminates obesity in rodents," Nat Chem Biol, 2009, 5:749.
Deyoung et al.."Encapsulation of exenatide in poly-(D,L-lactide-co-glycolide) microspheres produced an investigational long-acting once-weekly formulation for type 2 diabetes," Diabetes Technol Ther, 2011, 13, 1145-1154.
Ding et al., "βKlotho Is Required for Fibroblast Growth Factor 21 Effects on Growth and Metabolism," Cell Metab, 2012, 16(3):387-393.
Drucker "Mechanisms of Action and Therapeutic Application of Glucagon-like Peptide-1," Cell Metab, 2018, 27(4):740-756.
Drucker, "Incretin action in the pancreas: potential promise, possible perils, and pathological pitfalls," Diabetes, 2013, 62, 3316-3323.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
El-Assaad et al., "Saturated Fatty Acids Synergize with Elevated Glucose to Cause Pancreatic β-Cell Death," Endocrinology, 2003, 144(9):4154-4163.
Finan et al., "A rationally designed monomeric peptide triagonist corrects obesity and diabetes in rodents," Nat Med, 2015, 21:27-36.
Finan et al., "Unimolecular Dual Incretins Maximize Metabolic Benefits in Rodents, Monkeys, and Humans," Sci Transl Med, 2013, 5(209):209ra151.
Fosgerau et al., "Peptide therapeutics: current status and future directions," Drug Discovery Today, 2015, 20, 122-128.
Gaich et al., "The Effects of LY2405319, an FGF21 Analog, in Obese Human Subjects with Type 2 Diabetes," Cell Metab, 2013, 18(3):333-340.
Ganson et al., "Pre-existing anti-polyethylene glycol antibody linked to first-exposure allergic reactions to pegnivacogin, a PEGylated RNA aptamer," J Allergy Clin Immunol, 2016, 137(5): 1610-1613, e1617.
Gao, "Site-specific andin situgrowth of stealth polymer conjugates of proteins with significally improved pharmacology," Journal of Controlled Release, 2013, 172(1):e116-e117.
Gilroy et al., "Fusion of fibroblast growth factor 21 to a thermally responsive biopolymer forms an injectable depot with sustained anti-diabetic action," J Control Release, 2018, 277:154-164.
Gu et al., "Enzymatic Synthesis of Nucleobase-Modified Single-Stranded DNA Offers Turnable Resistance to Nuclease Degradation," Biomacromolecules, 2018, 19, 3525-3535.
Gu et al., "Photocontrolled micellar aggregation of amphiphilic DNA-azobenzene conjugates," Colloids Surfaces B: Biointerfaces, 2015, 135, 126-132.
Ha et al., "Immunoglobulin Fc Heterodimer Platform Technology: From Design to Applications in Therapeutic Antibodies and Proteins," Front Immunol, 2016, 7(394) (in English).
Hampp et al., "Use of Antidiabetic Drugs in the U.S., 2003-2012," Diabetes Care, 2014, 37: 1367-1374.
Hart et al., "Attenuation of FGF signalling in mouse β-cells leads to diabetes," Nature, 2000, 408:864.

Ito et al., "Impaired negative feedback suppression of bile acid synthesis in mice lacking βKlotho," J Clin Invest, 2005, 115(8):2202-2208.
Johnson et al., "Fibroblast Growth Factor 21 Reduces the Severity of Cerulein-Induced Pancreatitis in Mice," Gastroenterology, 2009, 137(5): 1795-1804.
Kaspar et al., "Future directions for peptide therapeutics development," Drug Discovery Today, 2013, 18, 807-817.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, 2015, 26(11):608-617.
Kharitonenkov et al., "Fibroblast growth factor 21 night watch: advances and uncertainties in the field," J Intern Med, 2016, 281(3):233-246.
Kharitonenkov et al., "Inventing new medicines: The FGF21 story," Mol Metab, 2014, 3(3):221-229.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, 2007, 30, 1487-93.
Kurosu et al., "Tissue-specific Expression of βKlotho and Fibroblast Growth Factor (FGF) Receptor Isoforms Determines Metabolic Activity of FGF19 and FGF21," J Biol Chern, 2007, 282(37):26687-26695.
Laybutt et al., "Endoplasmic reticulum stress contributes to beta cell apoptosis in type 2 diabetes," Diabetologia, 2007, 50(4):752-763.
Lee et al., "Nanoparticle-Delivered Chemotherapy: Old Drugs in New Packages." Oncology (Williston Park, NY) 31.3 (2017): 198-208.
Lee et al., "Structures of β-klotho reveal a 'zip code'-like mechanism for endocrine FGF signaling," Nature, 2018, 553:501-505.
Leibowitz et al., "Glucose-Regulated Proinsulin Gene Expression Is Required for Adequate Insulin Production during Chronic Glucose Exposure," Endocrinology, 2002, 143(9):3214-3220.
Li et al., "Prediction of solvent-induced morphological changes of polyelectrolyte diblock copolymer micelles," Soft Matter, 2015, 11(42): 8236-45.
Lin et al., "Adiponectin Mediates the Metabolic Effects of FGF21 on Glucose Homeostasis and Insulin Sensitivity in Mice," Cell Metab, 2013, 17(5):779-789.
Lin et al., "Functional expression of a biologically active fragment of soluble gp130 as an ELP-fusion protein in transgenic plants: purification via inverse transition cycling," Biochem J, 2006, 398(3):577-583.
Lin et al., "Statistical properties of the traditional algorithm-based designs for phase I cancer clinical trials," Biostatistics, 2001, 2(2):203-215.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, 2007, 40, 2503-2508.
Lutz et al., "Preparation of Ideal PEG Analogues with a Tunable Thermosensitivity by Controlled Radical Copolymerization of 2-(2-Methoxyethoxy) Methacrylate and Oligo(ethylene glycol) Methacrylate," Macromolecules, 2006, 39, 893-896.
Magnusson et al., "Ion-Sensitive "Isothermal" Responsive Polymers Prepared in Water," Journal of the American Chemical Society, 2008, 130, 10852-10853.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, 2008, 93(12):4810-4817.
Meier et al., "Determination of Optimal Sample Size for Quantification of β-Cell Area, Amyloid Area and β-Cell Apoptosis in Isolated Islets," J Histochem Cytochem, 2015, 63(8):663-673.

(56) References Cited

OTHER PUBLICATIONS

Mu et al., "FGF21 Analogs of Sustained Action Enabled by Orthogonal Biosynthesis Demonstrate Enhanced Antidiabetic Pharmacology in Rodents," Diabetes, 2012, 61(2):505-512.
Nanoprecision Medical, "Pipeline, Type II Diabetes," <http://www.nanoprecisionmedical.com/pipeline/diabetes> webpage available as early as Aug. 2018.
Nauck "Glucagon-like Peptide 1 (GLP-1) in the Treatment of Diabetes," Horm Metab Res, 2004, 36(11/12):852-858 (in English).
Nies et al., "Fibroblast Growth Factor Signaling in Metabolic Regulation," Front Endocrinol, 2016, 6(193) (in English).
Ozer et al., "Site-Specific and Stoichiometric Stealth Polymer Conjugates of Therapeutic Peptides and Proteins," Bioconjug Chem, 2017, 28(3):713-723.
Pang et al., "A Modular Method for the High-Yield Synthesis of Site-Specific Protein-Polymer Therapeutics," Angew Chem Int Ed Engl, 2016, 55, 10296-10300.
Park et al., "Exendin-4 and exercise improve hepatic glucose homeostasis by promoting insulin signaling in diabetic rats," Metabolism, 2010, 59, 123-133.
Poitout et al., "Glucolipotoxicity: Fuel Excess and β-Cell Dysfunction," Endocr Rev, 2008, 29(3):351-366.
Potthoff et al., "Endocrine fibroblast growth factors 15/19 and 21: from feast to famine," Genes Dev, 2012, 26(4):312-324.
Qi et al., "A brush-polymer conjugate of exendin-4 reduces blood glucose for up to five days and eliminates poly(ethylene glycol) antigenicity," Nat Biomed Eng, 2016, 1:0002.
Ray et al., "Aptamer-mediated delivery of chemotherapy to pancreatic cancer cells." Nucleic acid therapeutics, 2012, 22(5): 295-305.
Riedel et al., "Engineered glucagon-like peptide-1-producing hepatocytes lower plasma glucose levels in mice," Am J Physiol Endocrinol Metab, 2009, 296(4):E936-E944.
Rodriguez-Diaz et al., "Alpha cells secrete acetylcholine as a non-neuronal paracrine signal priming beta cell function in humans," Nat Med, 2011, 17:888-892.
Schwendeman et al., "Injectable controlled release depots for large molecules," J Control Release, 2014, 190, 240-253.
Shusharina et al., "Micelles of Diblock Copolymers with Charged and Neutral Blocks: Scaling and Mean-Field Lattice Approaches," Macromolecules, 2000, 33(10): 3892-3901.
Singhal et al., "Fibroblast Growth Factor 21 (FGF21) Protects against High Fat Diet Induced Inflammation and Islet Hyperplasia in Pancreas," PLoS One, 2016, 11(2):e0148252.
Smith et al., "The Role of Beta Cell Glucagon-like Peptide-1 Signaling in Glucose Regulation and Response to Diabetes Drugs," Cell Metab, 2014, 19(6):1050-1057.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, 2017, 158(5):1314-1327.
Sun et al., "Autofluorescence Imaging of Living Pancreatic Islets Reveals Fibroblast Growth Factor-21 (FGF21)-Induced Metabolism," Biophys J, 2012, 103(11):2379-2388.
Sun et al., "On the Thermally Reversible Dynamic Hydration Behavior of Oligo(ethylene glycol) Methacrylate-Based Polymers in Water," Macromolecules, 2013, 46, 236-246.
Talukdar et al., "A Long-Acting FGF21 Molecule, PF-05231023, Decreases Body Weight and Improves Lipid Profile in Non-human Primates and Type 2 Diabetic Subjects," Cell Metab, 2016, 23(3):427-440.
Tang et al., "Enzymatic Polymerization of High Molecular Weight DNA Amphiphiles That Self-Assemble into Star-Like Micelles," Advanced Materials, 2014, 26(19): 3050-3054.
Tang et al., "High-Molecular-Weight Polynucleotides by Transferase-Catalyzed Living Chain-Growth Polycondensation," Angew. Chem., 2017, 56(24): 6778-6782.
Tomiyama et al., "Relevant use of Klotho in FGF19 subfamily signaling system in vivo," Proc Natl Acad Sci USA, 2010, 107(4):1666-71.
Tschöp et al., "Unimolecular Polypharmacy for Treatment of Diabetes and Obesity," Cell Metab, 2016, 24(1):51-62.
Urry, "Free energy transduction in polypeptides and proteins based on inverse temperature transitions," Prog Biophys Mol Biol, 1992, 57(1):23-57.
Vlieghe et al., "Synthetic therapeutic peptides: science and market," Drug Discovery Today, 2010, 15, 40-56.
Wali et al., "Measuring Death of Pancreatic Beta Cells in Response to Stress and Cytotoxic T Cells," Methods in Molecular Biology, 2015, 1292:165-176.
Wei et al., "Fibroblast growth factor 21 promotes bone loss by potentiating the effects of peroxisome proliferator-activated receptor γ," Proc Natl Acad Sci USA, 2012, 109(8):3143-3148.
Wente et al., "Fibroblast Growth Factor-21 Improves Pancreatic β-Cell Function and Survival by Activation of Extracellular Signal-Regulated Kinase 1/2 and Akt Signaling Pathways," Diabetes, 2006, 55(9):2470-2478.
Xiaodong et al., "FGF21 Is Not a Major Mediator for Bone Homeostasis or Metabolic Actions of PPARα and PPARγ Agonists," J Bone Miner Res, 2017, 32(4):834-845.
Xu et al., "Downregulation of GLP-1 and GIP Receptor Expression by Hyperglycemia," Diabetes, 2007, 56(6):1551-58.
Xu et al., "Fibroblast Growth Factor 21 Reverses Hepatic Steatosis, Increases Energy Expenditure, and Improves Insulin Sensitivity in Diet-Induced Obese Mice," Diabetes, 2009, 58(1):250-259.
Yamamoto et al., "ATRP Synthesis of Thermally Responsive Molecular Brushes from Oligo(ethylene oxide) Methacrylates," Macromolecules, 2007, 40, 9348-9353.
Yang et al., "Long Term Exendin-4 Treatment Reduces Food Intake and Body Weight and Alters Expression of Brain Homeostatic and Reward Markers," Endocrinology, 2014, 155, 3473-3483.
Yusta et al., "GLP-1 receptor activation improves β cell function and survival following induction of endoplasmic reticulum stress," Cell Metab, 2006, 4(5):391-406.
Zhang et al., "In Depth Analysis on the Unusual Multistep Aggregation Process of Oligo(ethylene glycol) Methacrylate-Based Polymers in Water," Macromolecules, 2014, 47, 4728-4737.
Zununi Vahed et al., "Targeted cancer drug delivery with aptamer-functionalized polymeric nanoparticles," Journal of drug targeting, 2019, 27(3):292-299.
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
Aaron et al., "Elastin as a Random-Network Elastomer—a Mechanical and Optical Analysis of Single Elastin Fibers," Biopolymers, 1981, 20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic, " Bioeng Transl Med, Jun. 2016, 1(1):10-29.
Arami et al., "In vivo delivery, pharmacokinetics, biodistribution and toxicity of iron oxide nanoparticles," Chem Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3):198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.

(56) References Cited

OTHER PUBLICATIONS

Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.
Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Brangwynne et al., "Polymer physics of intracellular phase transitions," Nature Physics, Nov. 2015, 11 (11):899-904.
Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci U S A, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6): 1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell-material feedback," Nature chemical biology, Sep. 2019, 15(10): 1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci U S A, 2013, 110(33): 13392-13397.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.

Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Ehlerding et al., "Biodegradable and Renal Clearable Inorganic Na No. particles," Adv Sci (Weinh), Feb. 2016, 3(2):1500223.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Elsabahy et al., "Design of polymeric nanoparticles for biomedical delivery applications," Chem Soc Rev, 2012, 41 (7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.
Farokhzad et al., "Targeted nanoparticle-aptamer bioconjugates for cancer chemotherapy in vivo," Proc Natl Acad Sci U S A, 2006, 103(16):6315-20.
Franzmann et al., "Phase separation of a yeast prion protein promotes cellular fitness," Science, Jan. 2018, 359(6371):eaao5654.
Garcia Quiroz et al., "Syntax of Phase Transition Peptide Polymers with LCST and UCST Behavior," Jan. 1, 2013, Retrieved from the Internet: URL: https://dukespace.lib.duke.edu/dspace/bitstream/handle/10161/7256/GarciaQuirozduke0066D 11972.pdf?sequence=1&isAllowed=y.
Geng et al., Shape effects of filaments versus spherical particles in flow and drug delivery, Nat Nanotechnol, 2007, 2(4):249-55.
Gilbreth et al., "Structural insights for engineering binding proteins based on non-antibody scaffolds," Curr Opin Struct Biol, 2012, 22(4):413-20.
Gillies et al., "Dendrimers and dendritic polymers in drug delivery," Drug Discovery Today, 2005, 10(1):35-43.
Goldsmith et al., "Enzyme engineering: reaching the maximal catalytic efficiency peak," Curr Opin Struct Biol, Dec. 2017, 47:140-150.
Graff et al., "Theoretical analysis of antibody targeting of tumor spheroids: importance of dosage for penetration, and affinity for retention," Cancer Research, 2003, 63(6): 1288-1296.
Gratton et al., "The effect of particle design on cellular internalization pathways," Proc Natl Acad Sci U S A, 2008, 105(33):11613-8.
Gu et al., "Precise engineering of targeted nanoparticles by using self-assembled biointegrated block copolymers," Proc Natl Acad Sci U S A, 2008, 105(7):2586-91.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al.."Functional Implications of Intracellular Phase Transitions," Biochemistry, May 2018, 57(17):2415-2423.
Huber et al., "Designer amphiphilic proteins as building blocks for the intracellular formation of organelle-like compartments," Nat Mater, Jan. 2015, 14(1):125-132.
Jiang et al., "Nanoparticle-mediated cellular response is size-dependent," Nat Nanotechnol, 2008, 3(3): 145-50.
Jokerst et al., "Nanoparticle PEGylation for imaging and therapy," Nanomedicine (Lond), 2011, 6(4):715-28.
Jurney et al., "Unique size and shape-dependent uptake behaviors of non-spherical nanoparticles by endothelial cells due to a shearing flow," J Control Release, Jan. 2017, 245:170-176.
Kamaly et al., "Targeted polymeric therapeutic nanoparticles: design, development and clinical translation," Chem Soc Rev, 2012, 41(7):2971-3010.
Karagoz et al., "Polymerization-Induced Self-Assembly (PISA)—control over the morphology of nanoparticles for drug delivery applications," Polym. Chem., Jan. 2014, 5(2):350-355.

(56) References Cited

OTHER PUBLICATIONS

Kataoka et al., "Block copolymer micelles for drug delivery: Design, characterization and biological significance," Advanced Drug Delivery Reviews, 2001, 47:113-131.

Kelly et al., "Shape-specific, monodisperse nano-molding of protein particles," J Am Chem Soc, 2008, 130(16):5438-9.

Kesharwani et al., "Dendrimer as nanocarrier for drug delivery," Progress in Polymer Science, Feb. 2014, 39(2):268-307.

Kulkarni et al., "Design of lipid nanoparticles for in vitro and in vivo delivery of plasmid DNA," Nanomedicine, May 2017, 13(4): 1377-1387.

Lee et al., "Polymersomes for drug delivery: design, formation and characterization," J Control Release, 2012, 161(2):473-83.

Lewis et al., "Use of digitized video microscopy with a fluorogenic enzyme substrate to demonstrate cell-and compartment-specific gene expression in Salmonella enteritidis and Bacillus subtilis," Molecular microbiology, 1994, 13:655-662.

Li et al., "Phase transitions in the assembly of multivalent signalling proteins," Nature, 2012, 483(7389):336-340.

Li et al., "Tunable Assembly of Protein-Microdomains in Living Vertebrate Embryos," Advanced Biosystems, Oct. 2018, 2(10):1800112.

Lin et al., "Formation and Maturation of Phase-Separated Liquid Droplets by RNA-Binding Proteins," Mol Cell, Oct. 2015, 60(2):208-219.

Lin et al., "Intrinsically disordered sequences enable modulation of protein phase separation through distributed tyrosine motifs," J Biol Chem, Nov. 2017, 292(46): 19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17): 178101.

Liong et al., "Multifunctional inorganic nanoparticles for imaging, targeting, and drug delivery," ACS Nano, 2008, 2(5):889-96.

Liu et al., "Integrin 60 $v\beta_3$ -Targeted Cancer Therapy," Drug Dev Res, 2008, 69(6):329-339.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry 2009, 19(22):3576-3590.

Lukyanov et al., "Tumor-targeted liposomes: doxorubicin-loaded long-circulating liposomes modified with anti-cancer antibody," J Control Release, 2004, 100(1):135-44.

Lyons et al., "Comparisons of Recombinant Resilin-like Proteins: Repetitive Domains Are Sufficient to Confer Resilin-like Properties," Biomacromolecules, 2009, 10(11):3009-3014.

Lyons et al., "Design and facile production of recombinant resilin-like polypeptides: Gene construction and a rapid protein purification method," Protein Engineering Design & Selection, 2007, 20(1):25-32.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Malam et al., "Liposomes and nanoparticles: nanosized vehicles for drug delivery in cancer," Trends Pharmacol Sci 2009, 30(11):592-9.

Manders et al., "Dynamics of three-dimensional replication patterns during the S-phase, analysed by double labelling of DNA and confocal microscopy," Journal of cell science, 1992, 103(Pt 3):857-862.

Mao et al., "Net charge per residue modulates conformational ensembles of intrinsically disordered proteins," Proc Natl Acad Sci U S A, 2010, 107(18):8183-8188.

Masood, "Polymeric nanoparticles for targeted drug delivery system for cancer therapy," Mater Sci Eng C Mater Biol Appl, Mar. 2016, 60:569-578.

Mastria et al., "Nanoparticle formulation improves doxorubicin efficacy by enhancing host antitumor immunity," J Control Release, Jan. 2018, 269:364-373.

McKenzie et al., "Multivalent Binding of a Ligand-Coated Particle: Role of Shape, Size, and Ligand Heterogeneity," Biophys J, Apr. 2018, 114(8): 1830-1846.

Meng et al., "Stimuli-responsive polymersomes for programmed drug delivery," Biomacromolecules, 2009, 10(2):197-209.

Merkel et al., "Using mechanobiological mimicry of red blood cells to extend circulation times of hydrogel microparticles," Proc Natl Acad Sci U S A, 2011, 108(2):586-91.

Mitragotri et al., "Physical approaches to biomaterial design," J. Nat Mater, 2009, 8(1):15-23.

Modery et al., "Heteromultivalent liposomal nanoconstructs for enhanced targeting and shear-stable binding to active platelets for site-selective vascular drug delivery," Biomaterials, 2011, 32(35):9504-9514.

Molliex et al., "Phase separation by low complexity domains promotes stress granule assembly and drives pathological fibrillization," Cell, Sep. 2015, 163(1):123-133.

Moosmann et al., "Alpha complementation of LacZ in mammalian cells," Nucleic Acids Res, 1996, 24(6):1171-1172.

Mozhdehi et al., "Genetically Encoded Cholesterol-Modified Polypeptides," Journal of the American Chemical Society, Jan. 2019, 141(2):945-951.

Mozhdehi et al., "Genetically encoded lipid-polypeptide hybrid biomaterials that exhibit temperature-triggered hierarchical self-assembly," Nature chemistry, May 2018, 10(5):496-505.

Muiznieks et al., "Proline periodicity modulates the self-assembly properties of elastin-like polypeptides," J Biol Chem, 2010, 285(51):39779-39789.

Muro, "Challenges in design and characterization of ligand-targeted drug delivery systems," J Control Release, 2012, 164(2):125-37.

Napier et al., "Nanoparticle drug delivery platform," Journal of Macromolecular Science, Part C: Polymer Reviews, 2007, 47(3):321-327.

Nayeem et al., "Engineering enzymes for improved catalytic efficiency: a computational study of site mutagenesis in epothilone-B hydroxylase," Protein Eng Des Sei, 2009, 22(4):257-266.

Ni et al., "Engineering of inorganic nanoparticles as magnetic resonance imaging contrast agents," Chern Soc Rev, Nov. 2017, 46(23):7438-7468.

Niu et al., "The role of adhesion molecules, $\alpha v\beta 3$, $\alpha v\beta 5$ and their ligands in the tumor cell and endothelial cell adhesion," Eur J Cancer Prev, 2007, 16(6):517-27.

Nott et al., "Phase transition of a disordered nuage protein generates environmentally responsive membraneless organelles," Mol Cell, Mar. 2015, 57(5):936-947.

Ortega et al., "Hydrodynamic properties of rodlike and dislike particles in dilute solution," The Journal of Chemical Physics, 2003, 119(18):9914-9919.

Pak et al., "Sequence Determinants of Intracellular Phase Separation by Complex Coacervation of a Disordered Protein," Mol Cell, Jul. 2016, 63(1):72-85.

Palmerston Mendes et al., "Dendrimers as Nanocarriers for Nucleic Acid and Drug Delivery in Cancer Therapy," Molecules, Aug. 2017, 22(9):1401.

Pardridge, "The blood-brain barrier: bottleneck in brain drug development," NeuroRx, 2005, 2(1):3-14.

Parker et al., "Antibody mimics based on human fibronectin type three domain engineered for thermostability and high-affinity binding to vascular endothelial growth factor receptor two," Protein Eng Des Sel, 2005, 18(9):435-44.

Pastuszka et al., "A tunable and reversible platform for the intracellular formation of genetically engineered protein microdomains," Biomacromolecules, 2012, 13(11):3439-3444.

Peng et al., "Length-dependent prediction of protein intrinsic disorder," BMC Bioinformatics, 2006, 7:208.

Petros et al., "Strategies in the design of nanoparticles for therapeutic applications," Nat Rev Drug Discov, 2010, 9(8):615-27.

(56) References Cited

OTHER PUBLICATIONS

Qamar et al., "FUS Phase Separation Is Modulated by a Molecular Chaperone and Methylation of Arginine Cation-pi Interactions," Cell, Apr. 2018, 173(3):720-734.e15.

Quiroz et al., "Intrinsically disordered proteins access a range of hysteretic phase separation behaviors," Scientific advances, Oct. 2019, 5(10):eaax5177.

Ravikumar et al., "Mimicking adhesive functionalities of blood platelets using ligand-decorated liposomes," Bioconjugate chemistry, 2012, 23(6):1266-1275.

Rolland et al., "Direct fabrication and harvesting of monodisperse, shape-specific nanobiomaterials," J Am Chem Soc, 2005, 127(28):10096-100.

Rosenholm et al., "Towards multifunctional, targeted drug delivery systems using mesoporous silica nanoparticles—opportunities & challenges," Nanoscale, 2010, 2(10):1870-83.

Rösler et al., "Advanced drug delivery devices via self-assembly of amphiphilic block copolymers," Advanced Drug Delivery Reviews, 2001, 53:95-108.

Ryu et al., "Elastin-like polypeptide for improved drug delivery for anticancer therapy: preclinical studies and future applications," Expert Opinion on Drug Delivery, 2014, 12(4):653-667.

Sanna et al., "Targeted therapy using nanotechnology: focus on cancer," Int J Nanomedicine, Jan. 2014, 9:467-83.

Schnell et al., "Expression of integrin αvβ3 in gliomas correlates with tumor grade and is not restricted to tumor vasculature," Brain Pathol, 2008, 18(3):378-86.

Sharma et al., "Dendrimer nanoarchitectures for cancer diagnosis and anticancer drug delivery," Drug Discov Today, Feb. 2017, 22(2):314-326.

Sharma et al., "PLGA-based nanoparticles: A new paradigm in biomedical applications," TrAC Trends in Analytical Chemistry, Jun. 2016, 80:30-40.

Sharma et al., "Polymer particle shape independently influences binding and internalization by macrophages," Journal of Controlled Release, 2010, 147(3):408-412.

Shi et al., "Triggered sorting and co-assembly of genetically engineered protein microdomains in the cytoplasm," Adv Mater, 2014, 26(3):449-454.

Shin et al., "Liquid phase condensation in cell physiology and disease," Science, Sep. 2017, 357(6357):eaaf4382.

Sickmeier et al., "DisProt: the Database of Disordered Proteins," Nucleic Acids Res, 2007, 35:D786-793.

Simon et al., "Engineered Ribonucleoprotein Granules Inhibit Translation in Protocells," Molecular cell, Jul. 2019, 75(1):66-75.

Simon et al., "Programming molecular self-assembly of intrinsically disordered proteins containing sequences of low complexity," Nat Chem, Jun. 2017, 9(6):509-515.

Skerra, "Alternative non-antibody scaffolds for molecular recognition," Curr Opin Biotechnol, 2007, 18(4):295-304.

Smits et al., "Elastin-Like Polypeptide Based Nanoparticled: Design Rationale Toward Nanomedicine," Macromolecular Bioscience, 2014, 15(1):36-51.

Steichen et al., "A Review of Current Nanoparticle and Targeting Moieties for the Delivery of Cancer Therapeutics," Eur J Pharm Sci, 2013, 48(3):416-27.

Strulson et al., "RNA catalysis through compartmentalization," Nat Chem, 2012, 4(11):941-946.

Suk et al., "PEGylation as a Strategy for Improving Nanoparticle-Based Drug and Gene Delivery ," Adv Drug Deliv Rev, Apr. 2016, 99(Pt A):28-51.

Swider et al., "Customizing Poly(lactic-Co-Glycolic Acid) Particles for Biomedical Applications," Acta Biomater, Jun. 2018, 73:38-51.

Talelli et al., "Core-Crosslinked Polymeric Micelles: Principles, Preparation, Biomedical Applications and Clinical Translation," Nano Today, Feb. 2015, 10(1):93-117.

Thakor et al., "Clinically Approved Nanoparticle Imaging Agents," J Nucl Med, Oct. 2016, 57(12):1833-1837.

Theillet et al., "The alphabet of intrinsic disorder: I. Act like a Pro: On the abundance and roles of proline residues in intrinsically disordered proteins," Intrinsically Disord Proteins, 2013, 1(1):e24360.

Truong et al., "Polymeric filomicelles and nanoworms: two decades of synthesis and application," Polymer Chemistry, Jun. 2016, 7(26):4295-4312.

Truong et al., "The Importance of Nanoparticle Shape in Cancer Drug Delivery," Expert Opin Drug Deliv, Jan. 2015, 12(1):129-42.

Truong, et al., "The effect of hydration on molecular chain mobility and the viscoelastic behavior of resilin-mimetic protein-based hydrogels," Biomaterials, 2011, 32(33):8462-73.

Uversky et al., "Intrinsically disordered proteins as crucial constituents of cellular aqueous two phase systems and coacervates," FEBS Lett, Jan. 2015, 589(1):15-22.

Uversky et al., "Understanding protein non-folding," Biochim Biophys Acta, 2010, 1804(6):1231-1264.

Vazquez-Lombardi et al., "Challenges and Opportunities for Non-Antibody Scaffold Drugs," Drug Discov Today, Oct. 2015, 20(10):1271-83.

Venkataraman et al., "The Effects of Polymeric Nanostructure Shape on Drug Delivery," Adv Drug Deliv Rev, 2011, 63(14-15):1228-46.

Verma et al., "Effect of surface properties on nanoparticle-cell interactions," Small, 2010, 6(1):12-21.

Von Roemeling et al., "Breaking Down the Barriers to Precision Cancer Nanomedicine," Trends Biotechnol, Feb. 2017, 35(2):159-171.

Vonarbourg et al., "Evaluation of pegylated lipid nanocapsules versus complement system activation and macrophage uptake," J Biomed Mater Res A, 2006, 78(3):620-8.

Vrhovski et al., "Coacervation Characteristics of Recombinant Human Tropoelastin," European Journal of Biochemistry, 1997, 250(1):92-98.

Wang et al., "A Molecular Grammar Governing the Driving Forces for Phase Separation of Prion-like RNA Binding Proteins," Cell, Jul. 2018, 174(3):688-699.e616.

Wang et al., "More effective nanomedicines through particle design," Small, 2011, 7(14):1919-31.

Wang et al., "Nanoparticle delivery of cancer drugs," Annu Rev Med, 2012, 63:185-98.

Wang et al., "Stimuli-responsive Dendrimers in Drug Delivery," Biomater Sci, Mar. 2016, 4(3):375-90.

Wang et al., "The Weak Link: Optimization of the Ligand-Nanoparticle Interface To Enhance Cancer Cell Targeting by Polymer Micelles," Nano Lett Oct. 2017, 17(10):5995-6005.

Wechsel et al., "Renal Cell Carcinoma: Immunohistological Investigation of Expression of the Integrin αvβ3," Anticancer research, 1999, 19(2C): 1529-1532.

Weis et al., "αV Integrins in Angiogenesis and Cancer," Cold Spring Harb Perspect Med, 2011, 1(1):a006478.

Weitzhandler et al., "Micellar Self-Assembly of Recombinant Resilin-/Elastin-Like Block Copolypeptides," Biomacromolecules, Aug. 2017, 18(8):2419-2426.

Wilkins et al., "Hydrodynamic Radii of Native and Denatured Proteins Measured by Pulse Field Gradient NMR Techniques," Biochemistry, 1999, 38(50): 16424-16431.

Wimley et al., "Experimentally determined hydrophobicity scale for proteins at membrane interfaces," Nature Structural & Molecular Biology, 1996, 3(10):842-848.

Wright et al., "Intrinsically disordered proteins in cellular signalling and regulation," Nat Rev Mol Cell Biol, Jan. 2015, 16(1):18-29.

Xie et al., "The Effect of Shape on Cellular Uptake of Gold Nanoparticles in the Forms of Stars, Rods, and Triangles," Sci Rep, Jun. 2017, 7(1):3827.

Xiong et al., "Engineering of amphiphilic block copolymers for polymeric micellar drug and gene delivery," J Control Release, 2011, 155(2):248-61.

Xu et al., "Inorganic nanoparticles as carriers for efficient cellular delivery," Chemical Engineering Science, 2006, 61(3):1027-1040.

Zhao et al., "Cellular uptake, intracellular trafficking, and cytotoxicity of nanomaterials," Small, 2011, 7(10): 1322-37.

Zhao et al., "Tumor αvβ3 Integrin Is a Therapeutic Target for Breast Cancer Bone Metastases," Cancer Res, 2007, 67(12):5821-30.

(56) References Cited

OTHER PUBLICATIONS

United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
U.S. Appl. No. 13/245,459, filed Sep. 26, 2011, 8,470,967, Jun. 25, 2013.
U.S. Appl. No. 13/904,836, filed May 29, 2013, 8,912,310, Dec. 16, 2014.
U.S. Appl. No. 14/572,391, filed Dec. 16, 2014, 9,771,396, Jun. 25, 2013.
U.S. Appl. No. 15/679,751, filed Aug. 17, 2017, 2018/0037609, Feb. 8, 2018.
PCT/US2016/024202, Mar. 25, 2016, WO2016/154530, Sep. 26, 2016.
U.S. Appl. No. 15/561,799, filed Sep. 26, 2017, 10,385,115, Aug. 20, 2019.
U.S. Appl. No. 16/525,374, filed Jul. 29, 2019, 2019/0345228, Nov. 14, 2019.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, 10,364,451, Jul. 30, 2019.
U.S. Appl. No. 15/387,540, filed Dec. 21, 2016, 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
PCT/US20168/032785, May 15, 2018, WO2018/213320, Nov. 22, 2018.
U.S. Appl. No. 16/614,282, filed Nov. 15, 2019.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
PCT/US2017/051661, Sep. 14, 2017, WO2018/053201, Mar. 22, 2018.
U.S. Appl. No. 16/332,865, filed Mar. 13, 2019.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
PCT/US2018/040409, Jun. 29, 2018, WO2019/006374, Jan. 3, 2019.
U.S. Appl. No. 16/625,899, filed Dec. 23, 2019.
PCT/US2019/050077, Sep. 6, 2019.
PCT/US2019/061144, Nov. 13, 2019.
PCT/US2019/015176, Jan. 25, 2019, WO2019/147954, Aug. 1, 2019.
PCT/US2019/023583, Mar. 22, 2019, WO2019/183476, Sep. 26, 2019.
PCT/US2019/030022, Apr. 30, 2019, WO2019/213150, Nov. 7, 2019.
PCT/US2019/044911, Aug. 2, 2019.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
United States Patent Office Action for U.S. Appl. No. 15/749,797 dated Oct. 20, 2020 (16 pages).
AACR, "AACR Cancer Progress Report 2016," Clin Cancer Res, 2016, 22, 143 pages.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overcome the pathophysiological barriers of pancreatic cancer," Nat Rev Clin Oncol, 2016, 13, 750-765.
Aladini et al., "Chemical Synthesis and Characterization of Elastin-Like Polypeptides (ELPs) With Variable Guest Residues," J Pept Sci, 2016, 22(5):334-342.
Albanese et al., "The effect of nanoparticle size, shape, and surface chemistry on biological systems," Annu. Rev. Biomed. Eng., 2012, 14, 1-16.
Alconcel et al., "FDA-approved poly(ethylene glycol)-protein conjugate drugs," Polym. Chem. 2, 2011, 1442-1448.
Alley et al., "Feasibility of drug screening with panels of human tumor cell tines using a microculture tetrazolium assay," Cancer Res., 1988, 48, 589-601.
Aluri et al., "Elastin-like peptide amphiphiles Form nanofibers with tunable length," Biomacromolecules, 2012, 13, 2645-2654.
Amiram et al., "A depot-forming glucagon-like peptide-1 fusion protein reduces blood glucose for five days with a single injection," J. Control. Release, 2013, 172, 144-151.
Amiram et al., "Injectable protease-operated depots of glucagon-like peptide-1 provide extended and tunable glucose control," Proc. Natl. Acad. Sci. 110, 2013, 2792-2797.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Antos et al., "Lipid Modification of Proteins through Sortase-Catalyzed Transpeptidation," J. Am. Chem. Soc. 2008, 130, 16338-16343.
Antos et al., "Site-Specific N- and C-Terminal Labeling of a Single Polypeptide Using Sortases of Different Specificity," J. Am. Chem. Soc. 2009, 131, 10800-10801.
Arias et al., "Superior preclinical efficacy of gemcitabine developed as chitosan nanoparticulate system," Biomacromolecules 2011, 12, 97-104.
Armstrong et al., "Antibody against poly(ethylene glycol) adversely affects PEG-asparaginase therapy in acute lymphoblastic leukemia patients," Cancer 110, 2007, 103-111.
Armstrong et al., "The Hydrodynamic Radii of Macromolecules and Their Effect on Red Blood Cell Aggregation," Biophys. J., 2004, 87, 4259-4270.
Arnida et al., "Geometry and surface characteristics of gold nanoparticles influence their biodistribution and uptake by macrophages," Eur J Pharm Biopharm, 2011, 77, 417-423.
Asai et al., "Protein polymer hydrogels by in situ, rapid and reversible self-gelation," Biomaterials, 2012, 33, 5451-5458.
Atun et al., "Expanding global access to radiotherapy," Lancet Oncol, 2015, 16, 1153-1186.
Averick et al., "ATRP under biologically relevant conditions: grafting from a protein," ACS Macro. Lett. 1, 2012, 6-10.
Averick et al., "Protein-polymer hybrids: conducting ARGET ATRP from a genetically encoded cleavable ATRP initiator," Eur. Polym. J. 49, 2013, 2919-2924.
Awai et al., "Studies ofthe metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, 2013, 34, 2361-2369.

(56) References Cited

OTHER PUBLICATIONS

Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, 2012, 109(40):16101-16106.
Azhdarinia et al., "Regional radiochemotherapy using in situ hydrogel," PharmRes., 2005, 22, 776-783.
Bache et al., "Investigating the accuracy of microstereotactic-body-radiotherapy utilizing anatomically accurate 3D printed rodent-morphic dosimeters," Medical Physics, 2015, 42, 846-855.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Bailey et al., "Genomic analyses identify molecular subtypes of pancreatic cancer," Nature, 2016, 531, 47-52.
Bamford et al., "The COSMIC (Catalogue of Somatic Mutations in Cancer) database and website," British Journal of Cancer, 2004, 91, 355-358.
Banga et al., "Parenteral controlled delivery and parmacokinetics of therapeutic peptides and proteins," (CRC Press, Boca Raton, FL, 2005).
Bansal et al., "PEGylation improves pharmacokinetic profile, liver uptake and efficacy of Interferon gamma in liver fibrosis," J. Control. Release 2011, 154, 233-240.
Barbuti et al., "Paclitaxel through the ages of anticancer therapy: Exploring its role in chemoresistance and radiation therapy," Cancers, 2015, 7, 2360-2371.
Barnett et al., "Normal tissue reactions to radiotherapy: towards tailoring treatment dose by genotype," Nat Rev Cancer, 2009, 9, 134-142.
Barton et al., "Estimating the demand for radiotherapy form the evidence: A review of changes from 2003 to 2012," Radiother Oncol, 2014, 112, 140-144.
Baskar et al., "Cancer and Radiation Therapy: Current Advances and Future Directions," Int. J. Med. Sci., 2012, 9, 193-199.
Bedford et al., "WW domain-mediated interactions reveal a spliceosome-associated protein that binds a third class of proline-rich motif: The proline glycine and methionine-rich motif," PNAS, 1998, 95: 10602-10607.
Begg et al., "Strategies to improve radiotherapy with targeted drugs," Nat Rev Cancer, 2011, 11, 239-253.
Bellucci et al., "A noncanonical function of sortase enables site-specific conjugation of small molecules to lysine residues in proteins," Angew. Chem. Int. Ed. 54, 2015, 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.
Bender et al., "Synthesis, Crystallization, and Biological Evaluation of an Orally Active Prodrug of Gemcitabine," J. Med. Chem. 2009, 52, 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, 2011, 50, 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, 2010, 142, 312-318.
Bhattacharyya et al., "A paclitaxel-loaded recombinant polypeptide nanoparticle outperforms Abraxane in multiple murine cancer models," Nat. Commun. 2015, 6, 7939.

Bidwell et al., "Development of elastin-like polypeptide for thermally targeted delivery of doxorubicin," Biochemical Pharmacology, 2007, 73(5):620-631.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation Multiple exploitable mechanisms for combined treatment," Eur J Cancer, 2013, 49, 245-253.
Bocci et al., "The pharmacological bases of the antiangiogenic activity of paclitaxel," Angiogenesis, 2013, 16, 481-492.
Bochicchio et al., "Investigating by CD the molecular mechanismof elasticity of elastomeric proteins," Chirality, 2008, 20, 985-994.
Boekhorst et al., "Genome-wide detection and analysis of cell wall-bound proteins with LPxTG-like sorting motifs," J. Bacteriol. 187, 2005, 4928-4934.
Boldt, "Use of albumin: an update," Br J. Anaesth, 2010, 104 (3), 276-284.
Bond, "Exenatide (Byetta) as a novel treatment option for type 2 diabetes mellitus," Proc. (Bayl. Univ. Med. Cent.) 19, 2006, 281-284.
Bontempo et al., "Streptavidin as a macroinitiator for polymerization: in situ protein-polymer conjugate formation," J. Am. Chem. Soc., 2005, 6508-6509.
Boyer et al., "Well-Defined Protein-Polymer Conjugates via in Situ RAFT Polymerization," J. Am. Chem. Soc. 2007, 129, 7145-7154.
Branco et al., "Self-assembling materials for therapeutic delivery," Acta Biomaterialia, 2009, 5(3): p. 817-831.
Broyer et al., "Emerging synthetic approaches for protein-polymer conjugations," Chem Commun. 2011, 47, 2212.
Brusa et al., "Antitumor activity and pharmacokinetics of liposomes containing lipophilic gemcitabine prodrugs," Anticancer Res. 2007, 27, 195-199.
Burchard, "Light Scattering Techniques," Physical techniques for the study of food biopolymers, 1994, 151-213.
Burnouf, "Modern plasma fractionation," Transfus. Med. Rev., 2007, 21 (2), 101-117.
Cabral et al., "Accumulation of sub-100 nm polymeric micelles in poorly permeable tumours depends on size," Nature Nanotechnology, 2011, 6, 815-823.
Cai et al., "Long-acting preparations of exenatide," Drug Des. Dev. Ther. 7, 2013, 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, 2012, 12, 2165-2170.
Camilloni et al., "Determination of secondary structure populations in disordered states of proteins using nuclear magnetic resonance chemical shifts," Biochemistry, 2012, 51, 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.
Cardenes et al., "Locally advanced pancreatic cancer: Current therapeutic approach," The Oncologist, 2006, 11, 612-623.
Carrico et al., "Introducing genetically encoded aldehydes into proteins," Nat Chem Biol, 2007, 3(6):321-322.
Cataldo et al., "Radiation-induced crosslinking of collagen gelatin into a stable hydrogel," Journal of Radioanalytical and Nuclear Chemistry, 2008, 275, 125-131.

(56) References Cited

OTHER PUBLICATIONS

Ceska et al., "A new and rapid method for the clinical determination of α-amylase activities in human serum and urine. Optimal conditions," Clinica Chimica Acta, 1969, 26, 437-444.
Chakrabartty et al., "Stability of α-Helices," Adv Protein Chem, 1995, 46, 141-176.
Chang et al., "Tumor-stroma interaction in orthotopic primary pancreatic cancer xenografts during hedgehog pathway inhibition," Int. J. Cancer, 2013, 133, 225-235.
Chaudhury et al., "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, 2012, 89, 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am. Chem. Soc., 2009, 132(13):4577-4579.
Chen et al., "Rheology of Soft Materials," Annual Review of Condensed Matter Physics, 2010, 1, 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials 34, 2013, 8776-8785.
Chilkoti et al., "Design of thermally responsive, recombinant polypeptide carriers for targeted drug delivery," Advance Drug Delivery Reviews, 2002, 54:1093-1111.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, 2006, 6, 662-668.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem. 2013, 24, 1161-1173.
Cho et al., "Effects of hofmeister anions on the phase transition temperature of elastin-like polypeptides," J. Phys. Chem. B., 2008, 112, 13765-13771.
Cho et al., "Hydrogen bonding of β-turn structure is stabilized in D(2)O," J Am Chem Soc, 2009, 131, 15188-15193.
Cho et al., "Therapeutic nanoparticles for drug delivery in cancer," Clin Cancer Res., 2008, 14, 1310-1316.
Choi et al., "Renal Clearance of Nanoparticles," Nature biotechnology, 2007, 25(10): p. 1165-1170.
Chow et al., "Peptide-based biopolymers in biomedicine and biotechnology," Mater. Sci. Eng. R Reports, 2008, 62, 125-155.
Chow et al., "Ultra-High Expression of a Thermally Responsive Recombinant Fusion Protein in E. coli," Biotechnology Progress, 2006, 22(3):638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, 2009, 18:1377-1387.
Christensen et al., "Predicting Transition Temperatures of Elastin-Like Polypeptide Fusion Proteins," Biomacromolecules, 2013, 14(5): p. 1514-1519.
Cid-Arregui et al., "Perspectives in the treatment of pancreatic adenocarcinoma," World Journal of Gastroenterology, 2015, 21, 9297-9316.
Ciezki et al., "Brachytherapy or surgery? A composite view," Oncology, 2009, 23, 960-964.
Cima, "A VMA Guidelines for the Euthanasia of Animal: 2013 Edition," Journal of the American Veterinary Medical Association, 2013, 242, 102 pages.
Cirulis et al., "Viscoelastic properties and gelation of an elastin-like polypeptide," Journal of Rheology, 2009, 53, 1215-1228.
Clarke et al., "Tropoelastin massively associates during coacervation to form quantized protein spheres," Biochemistry, 2006, 45, 9989-9996.
Clavée et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., 2007, 2, 3247.
Colomb et al., "Radiation-Convertible Polymers fromNorbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, 2011, 9, 22-31.
Craik et al., "The future of peptide-based drugs," Chemical biology & drug design 81, 2013, 136-147.
Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalia Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.
Darzynkiewicz et al., "DNA content measurement for DNA ploidy and cell cycle analysis," Current Protocols in Cytometry, 2001, 7.5.1-7.5.24.
Dasgupta et al., "Isopeptide Ligation Catalyzed by Quintessential Sortase A: Mechanistic Cues From Cyclic and Branched Oligomers of Indolicidin," The Journal of Biological Chemistry, 2011, vol. 286, No. 27, pp. 23996-24006, Supplemental Information.
De et al., "Temperature-Regulated Activity of Responsive Polymer-Protein Conjugates Prepared by Grafting-from via RAFT Polymerization," J. Am. Chem. Soc. 2008, 130, 11288-11289.
De Simone et al., "Accurate random coil chemical shifts from an analysis of loop regions in native states of proteins," J Am Chem Soc, 2009, 131, 16332-16333.
Deer et al., "Phenotype and genotype of pancreatic cancer cell lines," Pancreas, 2010, 39, 425-435.
Dejana et al., "The role of adherens junctions and VE-cadherin in the control of vascular permeability," J Cell Sci, 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylationfor stabilizing biologies," Acta Biomater. 2009, 5, 560-569.
Deshayes et al., "Radium 223 dichloride for prostate cancer treatment," Drug Des Devel Ther, 2017, 11, 2643-2651.
Diana et al., "Prognostic role and correlation of CA9, CD31, CD68 and CD20 with the desmoplastic stroma in pancreatic ductal adenocarcinoma," Oncotarget, 2016, 7, 72819-72832.
Diehl et al., "A Good Practice Guide to the Administration of Substances and Removal of Blood Including Routes and Volumes," J Appl Toxicol, 2001, 21, 15-23.

(56) References Cited

OTHER PUBLICATIONS

Ding et al., "Mechanism for the alpha-helix to beta-hairpin transition," Proteins, 2003, 53, 220-228.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003,91:31-43.
Dreher et al., "Temperature triggered self-assembly of polypeptides into multivalent spherical micelles," J. Am. Chem. Soc. 2008, 130, 687-694.
Dreher et al., "Thermal cycling enhances the accumulation of a temperature-sensitive biopolymer in solid tumors," Cancer Res, 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., 2007, 341, 207-214.
Drucker et al., "The incretin system glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Du et al., "Endoscope-assisted brachytherapy for pancreatic cancer: From tumor killing to pain relief and drainage," Journal of interventional gastroenterology, 2011, 1, 23-27.
Du et al., "Tailor-made dual pH-sensitive polymer-doxorubicin nanoparticles for efficient anticancer drug delivery," J. Am Chem. Soc., 2011, 133, 17560-17563.
Duan et al., "Fibronectin type III domain based monobody with high activity," Biochemistry, 2007 46(44):12656-12664.
Dubey et al., "Development and evaluation of folate functionalized albumin nanoparticles for targeted delivery of gemcitabine," Int J Pharm., 2015, 492(1-2):80-91.
Ducreux et al., "Radiation plus docetaxel and cisplatin in locally advanced pancreatic carcinoma: A non-comparative randomized phase II trial," Digestive and Liver Disease, 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Eisenhaber et al., "Prediction of lipid posttranslational modifications and localization signals fromprotein sequences: Big-Π, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, 2017, 45, 228-247.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, 2010, 7(4):1015-1026.
Falk et al., "Hyperthermia in oncology," Int J Hyperthermia, 2001, 17, 1-18.

Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Feng et al., "Protein resistant surfaces: comparison of acrylate graft polymers bearing oligo-ethylene oxide and phosphorylcholine side chains," Biointerphases, 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, 2015, 16, 3389-3398.
Fluegel et al., "Chain stiffness of elastin-like polypeptides," Biomacromolecules 2010, 11, 3216-3218.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.
Friedman et al., "Directed Evolution to Low Nanomolar Affinity of a Tumor-Targeting Epidermal Growth Factor Receptor-Binding Affibody Molecule," J. Mol. Biol., 2008, 376, 1388-1402.
Frilling et al., "Recommendations for management of patients with neuroendocrine liver metastases," The lancet oncology, 2014, 15, e8-21.
Fu et al., Recent Patents on Anti-Cancer Drug Discovery, 2009. 4(3): p. 262-272.
Fujiwara et al., "Modulating effect of the PI3-kinase inhibitor LY294002 on cisplatin in human pancreatic cancer cells," Journal of Experimental & Clinical Cancer Research, 2008, 27, 76.
Furgeson et al., "Structural optimization of a "smart" doxorubicin-polypeptide conjugate for thermally targeted delivery to solid tumors," Journal of Controlled Release, 2006, 110:362-369.
Furumoto et al., "Effect of coupling of albumin onto surface of PEG liposome on its In vivo disposition," International Journal of Pharmaceutics, 2007, 329(1-2): p. 110-116.
Gaberc-Porekar et al., "Obstacles and pitfalls inthe PEGylation of therapeutic proteins," Curr. Opin. Drug Discov. Devel. 11, 2008, 242-250.
Gabizon et al., "Prolonged circulation time and enhanced accumulation in malignant exudates of doxorubicin encapsulated in polyethylene-glycol coated liposomes," Cancer Res. 1994, 54, 987-992.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009, 15231-15236.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and in patients treated with PEG-conjugated agents," Expert Opinion. Drug Deliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank AccessionNM_001182082.1 (2017).

(56) References Cited

OTHER PUBLICATIONS

Ghoorchian et al., "Molecular architecture influences the thermally induced aggregation behavior of elastin-like polypeptides," Biomacromolecules, 2011, 12, 4022-4029.

Gianni et al., "Nonlinear pharmacokinetics and metabolism of paclitaxel and its pharmacokinetic/pharmacodynamic relationships in humans," J. Clin. Oncol., 1995, 13 (1), 180-190.

Giberti et al., "Radical retropubic prostatectomy versus brachytherapy for low-risk prostatic cancer: a prospective study," World J Urol, 2009, 27, 607-612.

Gibson et al., "Enzymatic assembly of DNA molecules up to several hundred kilobases," Nat Methods, 2009, 6, 343-345.

Glassman et al., "Toughening of Thermoresponsive Arrested Networks of Elastin-Like Polypeptides To Engineer Cytocompatible Tissue Scaffolds," Biomacromolecules, 2016, 17, 415-426.

Gluck et al., "Single Vector System for Efficient N-myristoylation of Recombinant Proteins in E. coli," Pios One. 2010, 5(4) e100881.

Göke et al., "Exendin-4 is a high potency agonist and truncated exendin-(9-39)-amide an antagonist at the glucagon-like peptide 1-(7-36)-amide receptor of insulin-secreting b-cells," J. Biol. Chem 268, 1993, 19650-19655.

Gordon et al., "Protein N-myristoylation," J. Biol. Chem., 1991, 266, 8647-8650.

Gosline et al., "Elastic proteins: biological roles and mechanical properties," Philos Trans R Soc Lond B Biol Sci, 2002, 357, 121-132.

Gottlieb et al., "NMR chemical shifts of common laboratory solvents as trace impurities," J. Org. Chem., 1997, 62, 7512-7515.

Goutelle et al., "The Hill equation: a review of its capabilities in pharmacological modelling. Fundam," Clin. Pharmacol. 22, 2008, 633-648.

Greco et al., "The search for synergy: a critical review from a response surface perspective," Pharmacological Reviews, 1995, 24, 331-385.

Green et al., "Abraxane®, a novel Cremophor®-free, albumin-bound particle form of paclitaxel for the treatment of advanced non-small-cell lung cancer," Annals of Oncology, 2006, 17, 1263-1268.

Green et al., "Novel dipeptidyl peptidase IV resistant analogues of glucagon-like peptide-1 (7-3 6)amide have preserved biological activities in vitro conferring improved glucose-lowering action in vivo" J. of Mol. Endocrin., 2003, 31(3): 529-540.

Greenfield, "Using circular dichroism spectra to estimate protein secondary structure," Nat. Protoc., 2006, 1(6):2876-90.

Grimm et al., "Advances in Brachytherapy," Reviews in Urology, 2004, 6, S37-S48.

Grover et al., "Protein-Polymer Conjugates: Synthetic Approaches by Controlled Radical Polymerizations & Interesting Applications", Curr Opin Chem Bioi., Dec. 2010; 14(6): 818-827.

Güngör et al., "Pancreatic cancer," British Journal of Pharmacology, 2014, 171, 849-858.

Guo et al., "Nanoparticles escaping RES and endosome: challenges for siRNA delivery for cancer therapy," J. Nanomaterials, 2011, 2011: 1-12.

Gustafsson, "Nonlinear structured-illumination microscopy: widefield fluorescence imaging with theoretically unlimited resolution," Proc Natl Acad Sci U S A, 2005, 102, 13081-13086.

Gustafsson, "Surpassing the lateral resolution limit by a factor of two using structured illumination microscopy," Short Communication. Journal of Microscopy, 2000, 198, 82-87.

Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.

Haider et al., "Genetically engineered polymers: Status and prospects for controlled release," J. Control. Release, 2004, 95, 1-26.

Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.

Hamada et al., "Novel therapeutic strategies targeting tumor-stromal interactions in pancreatic cancer," Frontiers in Physiology, 2013, vol. 4, Article 331, 7 pages.

Hamidi et al., "Pharmacokinetic Consequences of Pegylation," Drug Deliv. 2006, 13, 399-409.

Hamley, "Self-assembly of amphiphilic peptides," Soft Matter, 2011, 7, 4122.

Han et al., "Survival of patients with advanced pancreatic cancer after iodine[125] seeds implantation brachytherapy: A meta-analysis," Medicine, 2017, 96, e5719.

Harmon et al., "A Model for Hysteresis Observed in Phase Transitions of Thermally Responsive Instrinsically Disordered Protein Polymers," Biophysical Journal, 2017, 112(3):207a.

Harries et al., "Nanoparticle Albumin-Bound Paclitaxel for Metastatic Breast Cancer," J. Clin Oncol., 2005, 23(31):7768-7771.

Harris et al., "Pegylation," Clinical Pharmacokinetics, 2001, 40(7):539-551.

Hartgerink et al., "Self-assembly and mineralization of peptide-amphiphile nanofibers," Science, 2001, 294, 1684-8.

Hassouneh et al., "Elastin-like Polypeptide Diblock Copolymers Self-Assemble into Weak Micelles," Macromolecules, 2015, 48, 4183-4195.

Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.

Hassouneh et al., "Fusions of elastin-like polypeptides to pharmaceutical proteins," Methods Enzymol., 2012, 502, 215-37.

Hassouneh et al., "Unexpected Multivalent Display ofProteins by Temperature Triggered Self-assembly of Elastin-like Polypeptide Block Copolymers," Biomacromolecules, 2012, vol. 13, Issue 4, pp. 1598-1605.

Hathout et al., "Analysis of seed loss and pulmonary seed migration in patients treated with virtual needle guidance and robotic seed delivery," American journal of clinical oncology, 2011, 34, 449-453.

He et al., "Comparative genomics of elastin Sequence analysis of a highly repetitive protein," Matrix Biology, 2007, 26:524-540.

He et al., "Improving protein resistance of α-Al2O3 membranes by modification with POEGMA brushes," Applied Surface Science, 2011, 258 (3), 1038-1044.

Heagerty et al., Biometrics, "Time-dependent ROC curves for censored survival data and a diagnostic marker," 2000, 56(2):337-44.

Heal et al., "N-Myristoyl transferase-mediated protein labelling in vivo," Org. Biomol. Cham., 2008, 6(13):2308-2315.

Heal et al., "Site-specific N-terminal labelling of proteins in vitro and in vivo using N-myristoyl transferase and bioorthogonal ligation chemistry," Chem. Commun., 2008, 3, 480-482.

Heredia et al., "In Situ Preparation of Protein-" Smart" Polymer Conjugates with Retention of Bioactivity," J. Am. Chem. Soc. 2005, 127, 16955-16960.

Herrero-Vanrell et al., "Self-assembled particles of an elastin-like polymer as vehicles for controlled drug release," J Control Release, 2005, 102, 113-122.

Hershfteld et al., "Induced and pre-existing anti-polyethylene glycol antibody in a trial of every 3-week dosing of pegloticase for refractory gout, including in organ transplant recipients," Arthritis Res. Ther. 16, 2014, R63.

Hidalgo, "Pancreatic Cancer," N Engl J Med, 2010, 362, 1605-1617.

Hingorani et al., "Phase Ib Study of PEGylated Recombinant Human Hyaluronidase and Gemcitabine in Patients with Advanced Pancreatic Cancer," Clinical Cancer Research, 2016, 22, 2848-2854.

Ho et al., "Chemoenzymatic Labeling of Proteins for Imaging in Bacterial Cells," J. Am. Chem. Soc., 2016, 138(46):15098-15101.

Ho et al., "Internal radiation therapy for patients with primary or metastatic licpatic cancer: a review," Cancer, 1998, 83, 1894-1907.

Hober et al., "Protein A chromatography for antibody purification," Journal of Chromatography B 848, 2007, pp. 40-47.

(56) References Cited

OTHER PUBLICATIONS

Hochkoeppler, "Expanding the landscape of recombinant protein production in *Escherichia coli*," Biotechnol. Lett., 2013, 35, 1971-1981.
Holehouse et al., "CIDER: Classification of Intrinsically Disordered Ensemble Regions," Biophysical Journal, 2015, vol. 108, Issue 2, Supplement 1, p. 228a.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011, 42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.
Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Ito et al., "In vivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogenperoxide systemto synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.
Jia et al., "Preparation, physicochemical characterization and cytotoxicity in vitro of gemcitabine-loaded PEG-PDLLA nanovesicles," World J. Gastroenterol. 2010, 16(8):1008-1013.
Jiang et al., "The internal structure of self-assembled peptide amphiphiles nanofibers," Soft Matter, 2007, 3, 454.
Jin et al., "Protein-resistant polyurethane prepared by surface-initiated atom transfer radical graft polymerizafion (ATRgP) of water-soluble polymers: effects of main chain and side chain lengths of grafts," Colloids and surfaces. B, Biointerfaces, 2009, 70 (1), 53-9.
Johansson et al., "Structure, Specificity, and Mode of Interaction for Bacterial Albumin-binding Modules," J. Biol. Chem. 2002, 277(10), 8114-8120.
Johansson et al., "The GA module, a mobile albumin-binding bacterial domain, adopts a three-helix-bundle structure," FEBS Lett, 1995, 374(2): 257-261.
Jonsson et al., "Engineering of a femtomolar affinity binding protein to human serum albumin," Protein Engineering Design and Selection, 2008, 21(8): 515-527.
Junutula et al., "Site-specific conjugation of a cytotoxic drug to antibody improves the therapeutic index," Nat Biotechnol, 2008, 26(8):925-932.
Kaighn et al., "Establishment and characterization of a human prostatic carcinoma cell line (PC-3)," Investigative urology, 1979, 17, 16-23.
Kaitin et al., "Pharmaceutical innovafioninthe 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanoski et al., "The role of nausea in food intake and body weight suppression by peripheral GLP-1 receptor agonists, exendin-4 and liraglutide," Neuropharmacology 62, 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version2.5 <http://rsb.info.nih.gov/ij/plugins/fraclac/FLHelp/Introduction.htm> 1999-2012.
Katakura, "Nuclear Data Sheets for A = 125," Nuclear Data Sheets, 2011, 112, 495-705.
Kato et al., "Acidic extracellular microenvironment and cancer," Cancer Cell Int, 2013, 13, 89, 8 pages.
Katti et al., "Amino acid repeat patterns inprotein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, 2012, 4(1):59-63.
Keller et al., "Empirical Statistical Model To Estimate the Accuracy ofPeptide Identifications Made by MS/MS and Database Search," Anal. Chem. 2002, 74, 5383-5392.
Kelly et al., "How to study proteins by circular dichroism," Biochim Byophys. Acta—Proteins Proteomics, 2005, 1751(2):119-39.
Keten et al., "Nanoconfmeme nt controls stiffness, strength and mechanical toughness of β-sheet crystals in silk," Nat Mater, 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., 2006, 24, 1065-1066.
Khazov et al., "Nuclear Data Sheets for A = 131," Nuclear Data Sheets, 2006, 107, 2715-2930.

(56) References Cited

OTHER PUBLICATIONS

Kim et al., "Recombinant elastin-mimetic biomaterials: Emerging applications in medicine," Adv Drug Deliv Rev, 2010, 62, 1468-1478.
Kim et al., "Site-Specific PEGylated Exendin-4 Modified with a High Molecular Weight Tri meric PEG Reduces Steric Hindrance and Increases Type 2 Antidiabetic Therapeutic Effects," Bioconjugate Chem. 2012, 23, 2214-2220.
Kim et al., "Ultrasensitive Carbon nanotube-based biosensors using antibody-binding fragments," Analytical Biochemistry, 2008, 381, 193-198.
Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11): 1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., 2015, 26(10):2153-2160.
Kulkarni et al., "Selective functionalization of the protein N terminus with N-myristoyl transferase for bioconjugation in cell lysate," ChemBioChem, 2013, 14, 1958-1962.
Kumar et al., "N-Terminal Region of the Catalytic Domain of Human N-Myristoyltransferase 1 Acts as an Inhibitory Module," PLoS One, 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Le Droumaguet et al., "Recent advances in the design of bioconjugates from controlled/living radical polymerization," Polym. Chem. 2010, 1, 563-598.
Le Meins et al., "Hybrid polymer/lipid vesicles: State of the art and future perspectives," Mater. Today, 2013, 16, 397-402.
Leader et al., "Protein therapeutics: a summary and pharmacological classification," Nat. Rev. Drug Discov. 7, 2008, 21-39.
Lee et al., "Atomistic molecular dynamics simulations of peptide amphiphile self-assembly into cylindrical nanofibers," J. Am. Chem. Soc., 2011, 133, 3677-3683.
Lee et al., "Immunohistochemical analysis of claudin expression in pancreatic cystic tumors," Oncology Reports, 2011, 25(4): 971-978.
Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.
Lee et al., "Mechanical properties of cross-linked syntheti elastomeric polypentapeptides," Macromolecules, 2001, 34, 5968-5974.
Lee et al., "Phase transition and elasticity of protein-based hydrogels," J. Biomater. Sci. Polymer Edn, 2001, 12, 229-242.
Lee et al., "Theranostic nanoparticles with controlled release of gemcitabine for targeted therapy and MRI of pancreatic cancer," ACS Nano 2013, 7(3):2078-2089.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., 2011, 77(22):8114-28.
Leung et al., "Bio-Click Chemistry: Enzymatic Functionalization of PEGylated Capsules for Targeting Applications**," Angew. Chem. Int. Ed. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs withPeptidic Albumin Binding Domains: Potent Anti-Diabetic Agents with Extended Duration of Action," PLoS ONE, 2014, 9(2): e87704, 9 pages.
Li et al., "Elastin is an essential determinant of arterial morphogenesis," Nature, 1998, 393, 276-280.
Li et al., "Molecular description of the LCST behavior of an elastin-like polypeptide," Biomacromolecules, 2014, 15, 3522-3530.
Li et al., "Nanoparticles Evading The Reticuloendothelial System Role of The Supported Bilayer," Biochim. Biophys. Acta, 2009, 1788 (10), 2259-2266.
Li et al., "Pancreatic cancer," Lancet, 2004, 363, 1049-1057.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macromol. Rapid Common, 2015, 36(1):90-95.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Proteinby Cationic Elastin-like Polypeptides" Biomacromolecules, 2007, 8(5): 1417-1424.
Lim et al., "In situ cross-linking of elastin-like polypeptide block copolymers for tissue repair," Biomacromolecules, 2008, 9, 222-230.
Lim et al., "In vivo post-translational modifications of recombinant mussel adhesive protein in insect cells," Biotechnol. Prog., 2011, 27, 1390-1396.
Lin et al., "Utility of immunohistochemistry inthe pancreatobiliary tract," Arch Pathol Lab Med, 2015, 139, 24-38.

(56) References Cited

OTHER PUBLICATIONS

Linder et al., "Lipid Modifications of G Protein Subunits," J. Biol. Chem., 1991, 266(7):4654-4659.
Ling et al., "Protein thioester synthesis enabled by sortase," J. Am Chem Soc, 2012, 134(26): 10749-10752.
Litiere et al., "RECIST—learning from the past to build the future," Nat Rev Clin Oncol, 2017, 14, 187-192.
Liu et al., "Brachytherapy using injectable seeds that are self-assembled from genetically encoded polypeptides in situ," Cancer Res, 2012, 72, 5956-5965.
Liu et al., "Hydrophobic modifications of cationic polymers for gene delivery," Prog. In Polym. Sci., 2010, 35, 1144-1162.
Liu et al., "In Situ Formation of Protein-Polymer Conjugates through Reversible Addition Fragmentation Chain Transfer Polymerization," Angew. Chem. Int. Ed. 2007, 46, 3099-3103.
Liu et al., "Injectable intratumoral depot of thermally responsive polypeptide-radionuclide conjugates delays tumor progression in a mouse model," J. Control Release, 2010, 144(1):2-9.
Liu et al., "Tracking the in vivo fate of recombinant polypeptides by isotopic labeling," Journal of Controlled Release, 2006, 114, 184-192.
Liu et al., "Tumor accumulation, degradation and pharmacokinetics of elastin-like polypeptides in nude mice," Journal of Controlled Release, 2006, 116, 170-178.
Livingstone, "Theoretical property predictions. Curr Top Med Chem FIELD Full Journal Tide: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, 2009, 262-269.
Ludden, "Nonlinear pharmacokinetics: clinical Implications," Clin Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng., 2017, 1, 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., 2017, 56: 13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, 2015, 137, 15362-15365.
Ma et al., "Non-fouling" oligo(ethylene glycolj-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.
MacEwan et al., "Applications of elastin-like polypeptides in drug delivery," Journal of Controlled Release, 2014, 190: p. 314-330.
MacEwan et al., "Controlled apoptosis by a thermally toggled nanoscale amplifier of cellular uptake," Nano Letters, 2014, 14, 2058-2064.
MacEwan et al., "Digital switching of local arginine density in a generically encoded self-assembled polypeptide nanoparticle controls cellular uptake," Nano Lett., 2012, 12, 3322-3328.
MacEwan et al., "Elastin-like polypeptides: Biomedical applications of tunable biopolymers," Biopolymers, 2010, 94, 60-77.
MacEwan et al., "Non-chromatographic Purification of Recombinant Elastin-like Polypeptides and their Fusions with Peptides and Proteins from *Escherichia coli*," 2014, 88, p. e51583.

MacEwan et al., "Phase Behavior and Self-Assembly of Perfectly Sequence-Defined and Monodisperse Multiblock Copolypeptides," Biomacromolecules, 2017, 18(2):599-609.
Mack et al., "Antiobesity action of peripheral exenatide (exendin-4) in rodents: effects onfood intake, body weight, metabolic status and side-effect measures," Int. J. Obes. 30, 2006, 1332-1340.
MacKay et al., "Self-assembling chimeric polypeptide-doxorubicin conjugate nanoparticles the abolish tumors after single injection," Nat Mater, 2009, 8(12):993-999.
Maeda et al., "Tumor vascular permeability and the EPR effect in macromolecular therapeutics: a review," J. Control. Release, 2000, 65(1-2)271-284.
Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, 2010, 671-678.
Maitra et al., "Pancreatic Cancer," Annu Rev Pathol Mech Dis, 2008, 3, 157-188.
Malik et al., "Recent advances in protein and peptide drug delivery systems," Curr. Drug Deliv. 2, 2007, 141-151.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, 2012, 72, 5566-5575.
Mao et al., "DNA repair by nonhomologous end joining and homologous recombination during cell cycle inhuman cells," Cell cycle, 2008, 7, 2902-2906.
Mao et al., "Sortase-mediated protein ligation: a new method for protein engineering," J. Am. Chem. Soc., 2004, 126(9):2670-2671.
Maraffinii et al., "Sortases and the art of anchoring proteins to the envelopes of Gram-positive bacteria," Microbiol Mol Biol Rev, 2006, 70(1): 192-221.
Mariam et al., "Albumin corona on nanoparticles—a strategic approach in drug delivery," Drug Deliv., 2016, 23 (8), 2668-2676.
Marr et al., "Effect of Temperature on the Composition of Fatty Acids in *Escherichia coli*," J Bacteriol., 1962, 84(6):1260-7.
Marten et al., "A randomized multicentre phase II trial comparing adjuvant therapy inpatients with interferon alpha-2b and 5-FU alone or in combination with either external radiation treatment and cisplatin (CapRI) or radiation alone regarding event-free survival—CapRI-2," BMC Cancer, 2009, 9, 1-8.
Maskarinec et al., "Protein engineering approaches to biomaterials design," Curr. Opin. Biotechnol., 2005, 16, 422-426.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, 2015, 208:52-8.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, 2012, 64, 710-719.
Matyjaszewski et al., "Atom transfer radical polymerization," Chem. Rev. 101, 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the CollagenType IVTriple Helix: Cis/Trans Proline-Induced Multiple 1H NMR Conformations and

(56) References Cited

OTHER PUBLICATIONS

Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, 2010, 457-469.
McDaniel et al., "A unilied model for de novo design of elastin-like polypeptides with tunable inverse transition temperatures," Biomacromolecules, 2013, 14(8):2866-2872.
McDaniel et al., "Actively targeting solid tumours with thermoresponsive drug delivery systems that respond to mild hyperthermia," Int J Hyperthermia, 2013, 29, 501-510.
McDaniel et al., "Doxorubicin-conjugated chimeric polypeptide nanoparticles that respond to mild hyperthermia," Control. Release, 2012, 159 (3), 362-367.
McDaniel et al., "Drug delivery to solid tumors by elastin-like polypeptides," Adc. Drug Deliver. Rev., 2010, 62(15):1456-1467.
McDaniel et al., "Noncanonical Self-Assembly of Highly Asymmetric Genetically Encoded Polypeptide Amphiphiles into Cylindrical Micelles," Nano Lett, 2014, 14(11):6590-6598.
McDaniel et al., "Rational design of "heat seeking" drug loaded polypeptide nanoparticles that thermally target solid tumors," Nano Letters, 2014, 14, 2890-2895.
McDaniel et al., "Self-assembly of thermally responsive nanoparticles of a genetically encoded peptide polymer by drug conjugation," Chem Int. Ed. 2013, 52, 1683-1687.
McDaniel et al., "Recursive Directional Ligation by Plasmid Reconstruction Allows Rapid and Seamless Cloning of Oligomeric Genes," Biomacromolecules, 2010, 11(4):944-952.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
Mejuch et al., "Synthesis of lipidated proteins," Bioconjug. Chem. 27, 2016, 1771-1783.
Mero et al., "Transglutaminase-mediated PEGylation of proteins: direct identification of the sites protein medificationby mass spectrometry using a novel monodisperse PEG," Bioconjug Chem, 2009, 20(2):384-389.
Merrick et al., "Seed fixity in the prostate/periprostatic region following brachytherapy," International journal of radiation oncology, biology, physics, 2000, 46, 215-220.
Methods and Welfare Considerations in Behavioral Research with Animal. (2002).
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, 2013, 62, 317-326.
Micsonai et al. "Accurate secondary structure prediction and fold recognition for circular dichroism spectroscopy," Proc Natl Acad Sci U S A, 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Mosbach et al., "Formation of proinsulin by immobilized Bacillus subtilis," Nature, 1983, 302, 543-545.
Muiznieks et al., "Structural changes and facilitated association of tropoelastin," Archives of Biochemistry and Biophysics, 2003, 410, 317-323.
Muiznies et al., "Modulated growth, stability and interactions of liquid-like coacervate assemblies of elastin," Matrix Biology 36, 2014, pp. 39-50.
Muñnoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III Temperature and pH dependence," J Mol Biol, 1995, 245, 297-308.
Muralidharan et al., "Protein Ligation: an Enabling Technology for the Biophysical Analysis of Proteins," Nature Methods, 2006, vol. 3, No. 6, pp. 429-438.
Murphy et al., "A dosimetric model of duodenal toxicity after stereotactic body radiotherapy for pancreatic cancer," Int J Radiation Oncology Biol Phys, 2010, 78, 1420-1426.
Na et al., "Thermoresponsive pore structure of biopolymer microspheres for a smart drug carrier," Langmuir, 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials 2014, 35(24):6482-6497.
Naim et al., "A Synthetic Resilin Is Largely Unstructured," Biophysical Journal, 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Neidigh et al., "Exendin-4 and glucagon-like-peptide-q: NMR structural comparisons inthe solution and micelle-associated states," Biochemistry 40, 2001, 13188-13200.
Nettles et al., "Applications of elastin-like polypeptides in tissue engineering," Adv Drug Deliv Rev, 2010, 62, 1479-1485.
Nettles et al., "In situ crosslinking elastin-like polypeptide gels for application to articular cartilage repair in a goat osteochondral defect model," Tissue Eng Part A, 2008, 14, 1133-1140.
Newcomb et al., "Advances in cryogenic transmission electron microscopy for the characterization of dynamic self-assembling nanostructures," Current Opinion in Colloid and Interface Science, 2012, 17, 350-359.
Newton et al., "Commissioning a small-field biological irradiator using point, 2D, and 3D dosimetry techniques," Medical Physics, 2011, 38, 6754-6762.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. 2006, 45, 4697-4699.

(56) References Cited

OTHER PUBLICATIONS

Nie, "Understanding and overcoming major barriers in cancer nanomedicine," Nanomedicine (Lond) 2010, 5 (4), 523-528.
Nielsen, "Incretin mimetics and DPP-IV inhibitors for the treatment of type 2 diabetes," Drug Discov. Today 10, 2005, 703-710.
Nilvebrant et al., "The albumin-binding domain as a scaffold for protein engineering," Computational and Structural Biotechnology Journal, 2013, 6: e201303009, 8 pages.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, 2008, 9, 2755-2763.
O'Day et al., "Therapeutic Protein-polymer Conjugates: Advancing beyond PEGylation," J. Am Chem. Soc., 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Ortony et al., "Internal dynamics of a supramolecular nanofibre," Nat. Mater., 2014, 13, 1-5.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, 2010, 102, 456-463.
Palta et al., "Interim Acute Toxicity Analysis and Surgical Outcomes of Neoadjuvant Gemcitabine/nab-Paclitaxel and Hypo fractionated Image Guided Intensity Modulated Radiation Therapy in Resectable and Borderline Resectable Pancreatic Cancer (ANCHOR) Study," International Journal of Radiation Oncology • Biology • Physics, 2016, 96, S204-S205.
Palva et al., "Secretion of interferon by Bacillus subtilis," Gene, 1983, 22, 229-235.
Paolino et al., "Folate-targeted supramolecular vesicular aggregates as a new frontier for effective anticancer treatment in in vivo model," Eur. J. Pharm. Biopharm. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release 2010, 144(2):144-150.
Paoloni et al., "Translation of new cancer treatments from pet dogs to humans," Nat. Rev. Cancer 2008, 8 (2), 147-156.
Papa et al., "PEGylated Liposomal Gemcitabine: Insights Into a Potential Breast Cancer Therapeutic," Cell Oncol. (Dordr) 2013, 36(6):449-457.
Paramonov et al., "Self-assembly of peptide-amphiphile nanofibers: The roles of hydrogen bonding and amphiphilic packing," J. Am. Chem. Soc., 2006, 128, 7291-7298.
Park et al., "Formulation optimization and in vivo proof-of-concept study of thermosensitive liposomes balanced by phospholipid, elastin-like polypeptide, and cholesterol," PLoS One, 2014, 9: e103116, 13 pages.
Parkes et al. "Discovery and development of exenatide: the first antidiabetic agent to leverage the multiple benefits ofthe incretin hormone, GLP-1," Expert Opinion Drug Deliv. 8, 2012, 219-244.
Parveen et al., "Nanomedicine," Clinical Pharmacokinetics, 2006, 45(10):965-988.
Patil et al., "Cellular delivery of doxorubicin via pH-controlled hydrazone linkage using multifunctional nano vehicle based on poly(beta-1-malic acid)," Int J Mol Sci, 2012, 13, 11681-11693.
Peeler et al., "Genetically encoded initiator for polymer growth from proteins," J. Am. Chem. Soc. 132, 2010, 13575-13577.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., 2017, 28(5):1403-1412.

Phan et al., "Temperature-responsive self-assembly of charged and uncharged hydroxyethylcellulose-graft-poly(N-isopropylacrylamide) copolymer in aqueous solution," Colloid Polym Sci., 2011, 289 (9), 993-1003.
Pinkas et al., "Tunable, post-translational hydroxylation of collagen domains in *Escherichia coli*," ACS Chem. Biol., 2011, 6, 320-324.
Pliarchopoulou et al., "Pancreatic cancer: Current and future treatment strategies," Cancer Treatment Reviews, 2009,35, 431-436.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve The Properties of Cytokines," PNAS, 2011, vol. 108, No. 8, pp. 3169-3174.
Potters et al., "12-year outcomes following permanent prostate brachytherapy inpatients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21, 418-429.
Provenzano et al., "Hyaluronan, fluid pressure, and stromal resistance in pancreas cancer," Br J Cancer, 2013, 108, 1-8.
Pulaski et al., "Mouse 4T1 breast tumor model," Curr. Protoc. Immunol., 2001, Chapter 20, Unit 20.2.
Qi et al., Dataset for A brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: a biomedical perspective," Polym Chem. 5, 2014, 266-276.
Qi et al., "Protein-polymer conjugation—moving beyond PEGylation," Curr. Opin Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Development of Orthotopic Pancreatic Tumor Mouse Models," Methods Mol Biol, 2013, 980: 215-223.
Qiu et al., "Polymer Architecture and Drug Delivery," Pharmaceutical Research, 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Sequence heuristics to encode phase behaviour in intrinsically disordered protein polymers," Nat. Mater., 2015, 14, 1164-1171.
Rabotyagova et al., "Protein-based block copolymers," Biomacromolecules, 2011, 12, 269-289.
Radivojac et al., "Intrinsic Disorder and Functional Proteomics," Biophysical Journal, 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, 2016, 76.

(56) References Cited

OTHER PUBLICATIONS

Rankine et al., "Investigating end-to-end accuracy of image guided radiation treatment delivery using a micro-irradiator," Physics in Medicine and Biology, 2013, 58, 7791-7801.
Rao et al., "Synthetic nanoparticles camouflaged with biometric erythrocyte membranes for reduced reticuloendothelial system uptake," Nanotechnology, 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Rauscher et al. "Proline and Glycine Control Protein Self-Organization into Elastomeric or Amyloid Fibrils," Structure, 2006, 14:1667-1676.
Regier et al., AmericanHeart Association2014 Scientific Sessions, 2015, vol. 7, pp. 299-303.
Reguera et al., "Thermal Behavior and Kinetic Analysis of the Chain Unfolding and Refolding and of the Concomitant Nonpolar Solvationand Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Engineered fibronectin type III domain with a RGDWE sequence binds with enhanced affinity and specificity to human $\alpha v\beta 3$ integrin," J Mol Biol, 2003, 326(5):1475-1488.
Richards et al., "Man's best friend: what can pet dogs teach US about non-Hodgkin lymphoma?" Inmunol Rev., 2016, 263 (1), 173-191.
Riddles et al., "Ellmaris reagent: 5,5'-dithiobis(2-nitrobenzoic acid)—a reexamination," Anal Biochem 1979, 94(1):75-81.
Rincon et al., "Biocompatibility of elastin-like polymer poly(VPAVG) microparticles: in vitro and invivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, 2015, 17, 661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Römer et al., "The elaborate structure of spider silk: structure and function of a natural high performance fiber," Prion 2, 2008, 154-161.
Roopenian et al., "FcRn: the neonatal Fc receptor comes of age," Nat. Rev. Immunol., 2007, vol. 7, No. 9, 715-725.
Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem Pharmacol. 1996, 51(7):911-908.
Russo et al., "The role of neoadjuvant therapy inpancreatic cancer: a review," Future Oncol, 2016, 12, 669-685.
Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Saifer et al., "Selectivity of binding of PEGs and PEG-like oligomers to anti-PEG antibodies induced by methoxyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schaal et al., "Biopolymer $\alpha$-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schellenberger et al., "A recombinant polypeptide extends the in vivo half-life of peptides and proteins in a tunable manner," Nat. Biotechnol. 27, 2009, 1186-1188.
Schlaff et al., "Bringing the heavy: carbon ion therapy inthe radiobiological clinical context," Radiation Oncology, 2014, 9, 1-18.
Schneider et al., "NIH Image to ImageJ: 25 years of image analysis," Nature Methods, 2012, 9, 671-675.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shadwick, "Mechanical design in arteries," J Exp Biol, 1999, 202, 3305-3313.
Shang et al., "pH-Dependent Protein Conformational Changes in Albumim:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Shen et al., "Conjugation site modulates the in vivo stability and therapeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.

(56) References Cited

OTHER PUBLICATIONS

Sherman et al., "Next-GenerationPEGylationEnables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.
Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Siegel et al., "Absorbed fractions for electrons and beta particles in spheres of various sizes," J Nucl Med, 1994, 35, 152-156.
Siegwart et al., "ATRP In The Design of Functional Materials for Biomedical Applications," Prog Polymer Science, 2012, vol. 37, No. 1, pp. 18-37.
Silberstein et al., "The SNM Practice Guideline for Therapy of Thyroid Disease with $^{131}$I, 3.0," J Nucl Med, 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Sisson et al., "Radiation safety in the treatment of patients with thyroid diseases by radioiodine 131I: practice recommendations of the American Thyroid Association," Thyroid, 2011, 21, 335-346.
Sonawane et al., "Hydrazo linkages inpH responsive drug delivery systems," European Journal Pharmaceutical Sciences, 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, 2016, 234:83-89.
Sriraman et al., "Barriers to drug delivery in solid tumors," Tissue Barriers, 2014, 2, 2-10.
Stefl et al., "RNA sequence-and shape-dependent recognition by proteins in the ribonucleoprotein particle" EMBO reports (2005) 6(1):33-38.
Stock et al., "Penile erectile function after permanent radioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.
Strohmaier et al., "Comparisonof $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, 2015, 10, 1-17.
Sumerlin, "Proteins as Initiators of Controlled Radical Polymerization: Grafting-from via ATRP and RAFT," ACS Macro Lett. 2012, 1, 141-145.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "EUS-guided interstitial brachytherapy of the pancreas: a feasibitity study," Gastrointestinal Endoscopy, 2005, 62, 775-779.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, 2014, 42, 1508-1516.
Swee et al., "Sortase-mediated modification of αDEC205 affords optimization of antigen presentation and immunization against a set of viral epitopes," Proc Natl Acad Sci USA, 2013, 110(4):1428-1433.
Swers et al., Multivalent Scaffold Proteins as Superagonists of TRAIL Receptor 2-Induced Apoptosis, Mol Cancer Ther, 2013, 12, 1235-1244.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., 2016, 15, 419-424.
Tang et al., "Identification of PECAM-1 in solid tumor cells and its potential involvement in tumor cell adhesion to endothelium," J. Biol. Chem, 1993, 268, 22883-22894.
Tantakitti et al., "Energy landscapes and functions of supramolecular systems," Nat. Mater., 2016, 15, 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Teicher, "In vivo/exvivo and in situ assays used in cancer research: a brief review," Toxicol. Pathol., 2009, 37 (1), 114 122.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tompa et al., "Fuzzy complexes: polymorphism and structural disorder in protein-protein interactions," Trends Biochem Sci, 2008, 33, 2-8.
Tong et al., "Protein Modification with Amphiphilic Block Copoly(2-oxazoline)s as a New Platform for Enhanced Cellular Delivery," Mol. Pharm, 2010, vol. 7, No. 4, pp. 984-992.
Ton-That et al., "Assembly of pili onthe surface of Corynebacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypep-

(56) References Cited

OTHER PUBLICATIONS tide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," SeminRadiat Oncol, 2014, 24, 140-147.
Trieu et al., "P0157 Preclinical evaluation of NBN-paclitaxel in pancreatic cancer xenograft models," Eur J Cancer, 2014, 50, e53.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11): 1454-61.
Tsarevsky et al., "Deactivation efficiency and degree of control over polymerization in ATRP in protic solvents," Macromolecules 37, 2004, 9768-9778.
Tsume et al., "The development of orally administrable gemcitabine prodrugs with D-enantiomer amino acids: Enhanced membrane permeability and enzymatic stability," Eur. J. Pharm Biopharm. 2014, 86(3):514-523.
Tu et al., "Stages in tropoelastin coalescence during synthetic elastin hydrogel formation," Micron, 2010, 41, 268-272.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Tward et al., "Survival of men with clinically localized prostate cancer treated with prostatectomy, brachytherapy, or no definitive treatment: impact of age at diagnosis," Cancer, 2006, 107, 2392-2400, doi: 10.1002/cncr.22261.
Uchida et al., "Potential of adenovirus-mediated REIC/Dkk-3 gene therapy for use inthe treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am Chem. Soc., 1991, 113(11):4346-4348.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.

Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21): 1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al.,"Polyoxazoline: Chemistry, properties and applications," Bioconjugate Chem., 2011, vol. 22, pp. 976-986.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry oftropoelastin," Eur J Biochem, 1998, 258, 1-18.
Vrignaud et al., "Strategies for the nanoencapsulation of hydrophilic molecules in polymer-based nanoparticles," Biomaterials 2011, 32(33):8593-8604.
Walczak, "Death Receptor-Ligand Systems in Cancer, Cell Death, and Inflammation," Cold Spring Harb. Perspect. Biol., 2013, 5, a008698.
Walsh et al., "Post-translational modifications inthe context of therapeutic proteins," Nat. Biotechnol., 2006, 24, 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm 2014, 11, 1140-1150.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparticles in Endo-Lysosomes by Local pH," Nano Lett, 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Wendt et al., "DNA-mediated Folding and Assembly of MyoD-E47 Heterodimers," Journal of Biol. Chem, 1998, 273(10):5735-5743.
Werle et al., "Strategies to improve plasma half life time of peptide and protein drugs," Amino Acids 30, 2006, 351-367.
Wienkers et al., "Predicting in vivo drug interactions from in vitro drug discovery data," Nat. Rev. Drug. Discov. 2005, 4(10):825-833.
Williams et al., "Targeted radionuclide therapy," Medical Physics, 2008, 35, 3062-3068.
Williamson et al., "Efficient N-terminal labehngof proteins by use of sortase," Angew Chem Int ed Engl, 2012, 51(37):9377-9380.

(56) References Cited

OTHER PUBLICATIONS

Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, 2016, 79, 405-412.
Xia et al., "Tunable self-assembly of genetically engineered silk—elastin-like protein polymers," Biomacromolecules, 2011, 12, 3844-3850.
Xu et al., "A quality by design (QbD) case study on liposomes containing hydrophilic API: II. Screening of critical variables, and establishment of design space at laboratory scale," Int. J. Pharm 2012, 423(2):543-553.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Genetically engineered block copolymers: influence of the length and structure of the coiled-coil blocks on hydrogel self-assembly," Pharm Res, 2008, 25, 674-682.
Xu et al., "Role of pancreatic stellate cells inpancreatic cancer metastasis," Am J of Pathology, 2010, 177, 2585-2596.
Xu et al., "Self-assembly behavior of peptide amphiphiles (PAs) with different length of hydrophobic alkyl tails," Colloids Surfaces B Biointerfaces, 2010, 81, 329-335.
Yang et al., "Poly(carboxybetaine) nanomaterials enable long circulation and prevent polymer-specific antibody production," Nano Today, 2014, 9(1):10-16.
Yates et al., "Contemporary management of patients with high-risk non-muscle-invasive bladder cancer who fail intravesical BCG therapy," World journal of urology, 2011, 29, 415-422.
Yeo et al., "Coacervation of tropoelastin," Adv Colloid Interface Sci, 2011, 167, 94-103.
Yokoe et al., "Albumin-conjugated PEG liposome enhances tumor distribution of liposomal doxorubicin in rats," International Journal of Pharmaceutics, 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm Res., 1999, 16(7): 1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem Pharmacol, 2007, 73: 84-93.
Youn et al., "High-yield production of biologically active mono-PEGylated salmon calcitonin by site-specific PEGylation," J. Control. Release 117, 2007, 371-379.
Yousefpour et al., "Co-opting biology to deliver drugs," Biotechnol Bioeng, 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett. 2018, 18(12): 7784-7793.
Yu et al., "Effectiveness and security of CT-guided percutaneous implantation of (125)1 seeds in pancreatic carcinoma," The British journal of radiology, 2014, 87, 20130642, 7 pages.
Zhang et al., "A self-assembly pathway to aligned monodomain gels," Nat. Mater., 2010, 9, 594-601.
Zhang et al., "Nanoparticles in medicine: therapeutic applications and developments," Clin Pharmacol. Ther. 2008, 83(5):761-769.
Zhang et al., "Novel agents for pancreatic ductal adenocarcinoma: emerging therapeutics and future directions," Jounral of Hematology & Oncology, 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "A new Bliss Independence model to analyze drug combination data," J Biomol Screen, 2014, 19, 817-821.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem Phys. 1948, 16, 1099-1116.
Zini et al., "Contemporary management of adrenocortical carcinoma," European urology, 2011, 60, 1055-1065.
Zong et al., "Crystal structures of *Staphylococcus aureus* sortase A and its substrate complex," J. Biol. Chem. 279, 2004, 31383-31389.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
United States Patent Office Actionfor U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Actionfor U.S. Appl. No. 13/942,037 dated Jan. 15, 2016 (19 pages).
United States Patent Office Actionfor U.S. Appl. No. 13/942,037 dated Jun. 4, 2015 (33 pages).
United States Patent Office Actionfor U.S. Appl. No. 13/942,037 dated Nov. 28, 2016 (22 pages).
United States Patent Office Actionfor U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Actionfor U.S. Appl. No. 14/572,391 dated Oct. 26, 2016 (11 pages).

(56) References Cited

OTHER PUBLICATIONS

United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US2019/061144 dated May 21, 2020 (15 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13:4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15:283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Chu et al., "Controllable monodisperse multiple emulsions," Angew Chem Int Ed Engl, 2007, 46: 8970-8974.
Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Giiffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64:1868-1873.
Hwang et al., "Differentially degradable janus particles for controlled release applications," Macromol Rapid Commun, 2012, 33: 1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7:4821-4827.
Ma et al., "Core-shell hydrogel microcapsules for improved islets encapsulation," Adv Healthc Mater, 2013, 2: 667-672.
Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8: 1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membrane-less organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22:1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.
United States Patent Office Notice of Allowance for U.S. Appl. No. 16/332,865 dated Apr. 2, 2021 (10 pages).
Resh, "Covalent Lipid Modifications of Proteins," Curr Biol., May 2013, 23(10): R431-R435.
United States Patent Office Action for Application No. 16/477,229 dated Apr. 12, 2021 (14 pages).
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1:S49-52.
Arshavsky-Graham et al., "Lab-on-a-Chip Devices for Point-of-Care Medical Diagnostics," Advances in Biochemical Engineering/Biotechnology, 2020, 19 pages.
Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.

(56) References Cited

OTHER PUBLICATIONS

Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009,98(4): 1556-1567.
Chen et al., "Real-world patterns of pegloticase use for treatment of gout: descriptive multidatabase cohort study," BMJ Open, 2020, 10: e041167, 6 pages.
Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.
Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.
Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chem Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2:214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21 (19): 1968-1971.

Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.
McAndrews et al., "Heterogeneous antibodies against SARS-CoV-2 spike receptor binding domain and nucleocapsid with implications for COVID-19 immunity," JCI Insight, 2020, 5(18):e142386, 14 pages.
McElvaney et al., "A linear prognostic score based on the ratio of interleukin-6 to interleukin-10 predicts outcomes in COVID-19," EBioMedicine, 2020, 61: 103026, 8 pages.
Mejía-Salazar et al., "Microfluidic Point-of-Care Devices: New Trends and Future Prospects for eHealth Diagnostics," Sensors, 2020, 20: 1951, 19 pages.
Miller et al., "Disease and healthcare burden of COVID-19 in the United States," Nat Med, 2020, 26:1212-1217.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Norman et al., "Ultrasensitive high-resolution profiling of early seroconversion in patients with COVID-19," Nat Biomed Eng, 2020, 11 pages.
Nunn et al., "Crystal Structure of Tobacco Etch Virus Protease Shows the Protein C Terminus Bound within the Active Site," Journal of Molecular Biology, 2005, 350: 145-155.

(56) References Cited

OTHER PUBLICATIONS

Nyborg et al., "A Therapeutic Uricase with Reduced Immunogenicity Risk and Improved Development Properties," PLoS One, 2016, 11(12): e0167935, 23 pages.
Okba et al., "Severe Acute Respiratory Syndrome Coronavirus 2-Specific Antibody Responses in Coronavirus Disease Patients," Emerg Infect Dis, 2020, 26: 1478-1488.
Ozer et al., "Effect of Molecular Architecture on Cell Interactions and Stealth Properties of PEG," Biomacromolecules, 2017, 18: 2699-2710.
Pecoraro et al., "A systematic evaluation of immunoassay point-of-care testing to define impact on patients' outcomes," Ann Clin Biochem, 2017, 54(4): 420-431.
Ponti et al., "Biomarkers associated with COVID-19 disease progression," Crit Rev Clin Lab Sci, 2020, 57, 11 pages.
Posthuma-Trumpie et al., "Lateral flow (immuno)assay: its strengths, weaknesses, opportunities and threats. A literature survey," Anal Bioanal Chem, 2009, 393: 569-582.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ravichandran et al., "Antibody signature induced by SARS-CoV-2 spike protein immunogens in rabbits," Sci Transl Med, 2020, 10.1126/scitranslmed.abc3539, 9 pages.
Rogers et al., "Isolation of potent SARS-CoV-2 neutralizing antibodies and protection from disease in a small animal model," Science, 2020, 369: 956-963.
Rosadas et al., "Testing for responses to the wrong SARS-CoV-2 antigen," Lancet, 2020, 396: e23.
Rothe et al., "Transmission of 2019-nCoV Infection from an Asymptomatic Contact in Germany," N Engl J Med, 2020, 382: 10, 2 pages.
Seow et al., "Longitudinal evaluation and decline of antibody responses in SARS-CoV-2 infection," medRxiv, 2020, 24 pages.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Tang et al., "Laboratory Diagnosis of COVID-19: Current Issues and Challenges," J Clin Microbiol, 2020, 58: e00512-20, 9 pages.
Turner et al., "Challenges and Opportunities for the Subcutaneous Delivery of Therapeutic Proteins," Journal of Pharmaceutical Sciences, 2018, 107(5): 1247-1260.
U.S. FDA—Classify your medical devices. Updated as of: Feb. 7, 2020. Available at: <https://www.fda.gov/medical-devices/overview-device-regulation/classify-your-medical-device>.
U.S. FDA—In Vitro Diagnostics. Updated as of: Oct. 25, 2019. Available at: <https://www.fda.gov/medical-devices/products-and-medical-procedures/vitro-diagnostics>.
Vaninov, "In the eye of the COVID-19 cytokine storm," Nat Rev Immunol, 2020, 20: 277, 1 page.
Vashist et al., "Emerging Technologies for Next-Generation Point-of-Care Testing," Trends Biotechnol, 2015, 33(11): 692-705.
Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Whitman et al., "Evaluation of SARS-CoV-2 serology assays reveals a range of test performance," Nat Biotechnol, 2020, 38:1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581: 465-469.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
Nikolic et al., "Structural basis for the recognition of LDL-receptor family members by VSV glycoprotein," Nature Communications, 2018, 9:1029,12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
International Search Report and Written Opinion for Application No. PCT/US2021/046833 dated Nov. 8, 2021 (12 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.

(56) References Cited

OTHER PUBLICATIONS

Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapters, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chern. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chern. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chern. Res., 1978, 11(5): 211-217.
Maier et al., "From selection hits to clinical leads: progress in aptamer discovery," Mol. Ther. Methods Clin. Dev., 2016, 3: 16014, 10 pages.
Mcmanus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chern Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," Aaps J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor IXa," Nature, 2002, 19(6902): 90-94.
Shu et al., "GISAID: Global initiative on sharing all influenza data - from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 Dna polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vase Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The No. of operations required for completing breast reconstruction," Plast Reconstr Surg Glob Open, 2012, 2: e242.
Frandsen et al., "Recombinant protein-based polymers for advanced drug delivery," Chern Soc Rev, 2012,41:2696-2706.
Gabriel et al., "Fat grafting and breast reconstruction: tips for ensuring predictability," Gland Surg, 2015, 4:232-243.
Gylbert, "Applanation tonometry for the evaluation of breast compressibility," Scand J Plast Reconstr Surg Hand Surg, 1989, 23: 223-229.
Hsu et al., "Fat grafting's past, present, and future: why adipose tissue is emerging as a critical link to the advancement of regenerative medicine," Aesthet Surg J, 2015, 32: 892-899.
Kronowitz et al., "Delayed-lmmediate Breast Reconstruction," Plastic and Reconstructive Surgery, 2004, 113: 1617- 1628.

(56) References Cited

OTHER PUBLICATIONS

Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co - injections of Autologous Fat with Fillers," International Journal of Surgery & Surgical Techniques, 2016, 2: 7 pages.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg(Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB - P15214 (Gst_Promi) acessed online at <https://www.uniprot.org/uniprot/P15214 6/> on Jun. 8, 2021, 7 p.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 15/749,797 dated Jun. 2, 2022 (6 pages).
United States Patent Office Action for Application No. 16/477,229 dated Jun. 13, 2022 (11 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).

\* cited by examiner

NONFOULING BIOSENSORS

CROSS-REFERENCE TO RELATED APPLICATION

This present patent application is a national stage filing under 35 U.S.C. § 371 of International Application No. PCT/US2017/035530, filed on Jun. 1, 2017, which application claims priority to U.S. Provisional Application No. 62/343,926 filed on Jun. 1, 2016, and U.S. Provisional Application No. 62/414,877 filed on Oct. 31, 2016, the content of which are incorporated fully herein by reference in their entirety.

BACKGROUND

Printed electronics is a rapidly expanding field as it offers easy integration into current manufacturing processes, is inherently low-cost, and enables rapid fabrication of large-area sensors for use in Internet-of-Things (IoT) technologies. Recently, nanomaterials have provided a viable path forward for printed electronics, especially with the commercial availability of solution-processed semiconducting carbon nanotubes (CNTs). Printed CNT thin-film transistors (TFTs) have shown high performance, while remaining robust to the environment, unlike the more traditional printed organic semiconductors. CNTs have also proven useful in highly sensitive biosensor applications, where small changes in charge in the vicinity of the CNTs can produce a sizeable electrical response. Nonetheless, there is still a need for improved CNT-based biosensors that can accurately and sensitively detect analytes in a biological milieu without, e.g., rinsing or pre-sample calibration.

SUMMARY

In one aspect, disclosed are sensors that include a conductive substrate; a first dielectric layer positioned on the conductive substrate; a carbon nanotube channel comprising at least one carbon nanotube, the carbon nanotube channel being positioned on the first dielectric layer; a source electrode and a drain electrode positioned on the carbon nanotube channel; a second dielectric layer positioned on the carbon nanotube channel; a non-fouling polymer layer comprising hydroxy terminated poly oligo(ethylene glycol) methyl methacrylate (POEGMA), alkoxy terminated POEGMA, a copolymer of alkoxy-terminated POEGMA and hydroxy-terminated POEGMA, or a combination thereof, the non-fouling polymer layer being positioned on the second dielectric layer; and at least one capture agent adapted to specifically bind to a target analyte, the capture agent being bound to the non-fouling polymer layer.

In another aspect, disclosed are methods of detecting the presence or absence of an analyte. The methods include contacting the disclosed sensor with a sample; measuring an electrical property of the carbon nanotube channel; and determining the presence of the analyte, wherein the presence of the analyte is detected through a change in the electrical property of the carbon nanotube channel upon binding of the analyte to the capture agent.

DETAILED DESCRIPTION

Figure 1:
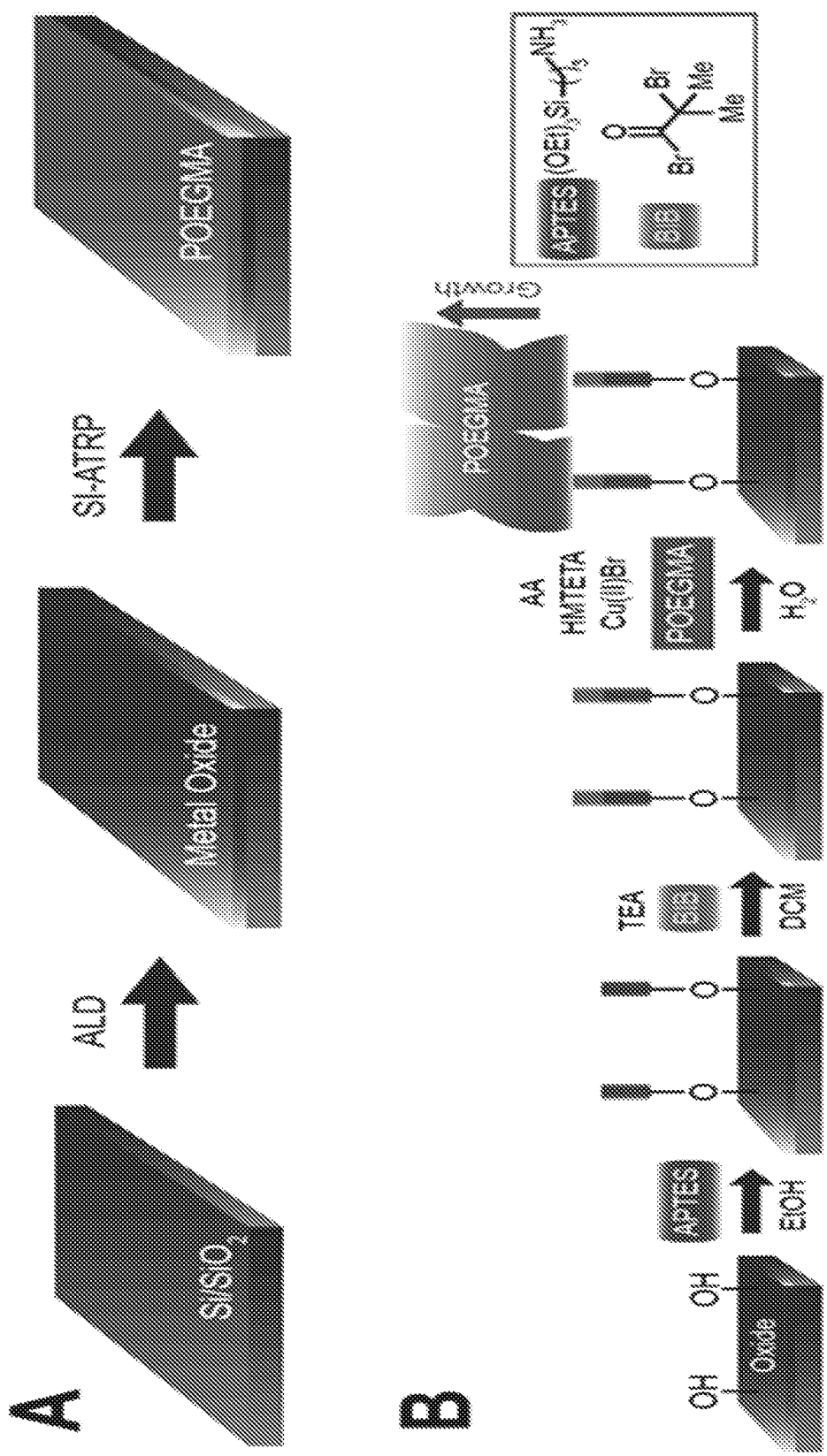
FIG. 1 is a schematic showing Poly oligo(ethylene glycol) methyl ether methacrylate (POEGMA) brush growth from dielectric oxide materials by surface-initiated atom transfer radical polymerization (SI-ATRP).

Disclosed herein are biosensors that show advantageous accuracy and sensitivity of detection of target analytes in biological samples. The biosensors include a POEGMA-based non-fouling polymer layer and a printed carbon nanotube thin-filmed transistor, where a dielectric layer is positioned in between the carbon nanotube thin film and the POEGMA layer. The biosensors can detect the presence (or absence) of an analyte through binding interactions between the target analyte and capture agent(s) printed, non-covalently onto the POEGMA layer, which can then result in a change of an electrical property of the carbon nanotube thin-filmed transistor.

It was found that POEGMA can be synthesized onto metal oxide surfaces—in particular, high-permittivity ("high-κ") metal oxide dielectrics, and that POEGMA can function as a dielectric, thereby permitting the biosensors to maintain good electrical conductivity, while also having the advantage of POEGMA's non-fouling property. Furthermore, it was found that POEGMA has a high breakdown voltage characteristic, which allows the disclosed biosensors to function up to high voltages.

In addition, it was found that a more robust and reliable sensor can be provided when there is a dielectric layer positioned in between the POEGMA layer and the carbon nanotube transistor film. It is well-recognized in the art that it is desirable to have the capture agent as close to the carbon nanotube film as possible, as the closer proximity can achieve a greater change in signal due to the binding event between the capture agent and the target analyte. For example, Kim et al., "Ultrasensitive carbon nanotube-based biosensors using antibody-binding fragments," *Anal. Biochem.*, vol. 381, no. 2, pp. 193-198, 2008, which is incorporated by reference herein in its entirety, found that proximity (e.g., Debeye length in this instance) of the capture agent to the CNT channel impacted the overall sensitivity of the sensor. Specifically, Kim et al. found that smaller fragments of the capture agent (e.g., fragment of an antibody) were able to sense concentrations at a lower limit of 1 pg/ml IgG, while the larger full antibodies had a lower limit of approximately 1000 ng/ml IgG. In fact, they suggested that the Debeye length is approximately 3 nm in a 10 mM buffer solution, and that the capture agents must fit in this range to electrostatically alter the CNT channel in order to modulate the conductance. Yet, it has been found with the disclosed sensors that the capture agent does not have to be in direct contact or in relatively close proximity to the carbon nanotube channel to achieve sensitive and accurate detection of a target analyte. Rather, sensitive detection can still be achieved when at least a dielectric layer is positioned in between the capture agent and the carbon nanotube film.

The advantages of the disclosed biosensors have been demonstrated through the detection of leptin within a serum sample down to a concentration of 10 pg/ml, with a detection range of $10^5$. Moreover, the biosensors needs calibration only with the dry transistor characteristics, furthering its viability as a real world, commercial biosensor application.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "alkoxy" as used herein, refers to a radical of the formula R—O—, wherein R is a straight-chain or branched alkyl group having from 1 to 20, in particular 1 to 4 carbon atoms. Examples include methoxy, ethoxy, n-propoxy, iso-propoxy, n-butoxy, 2-butoxy, iso-butoxy (2-methyl-propoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

2. Sensors

Figure 15:
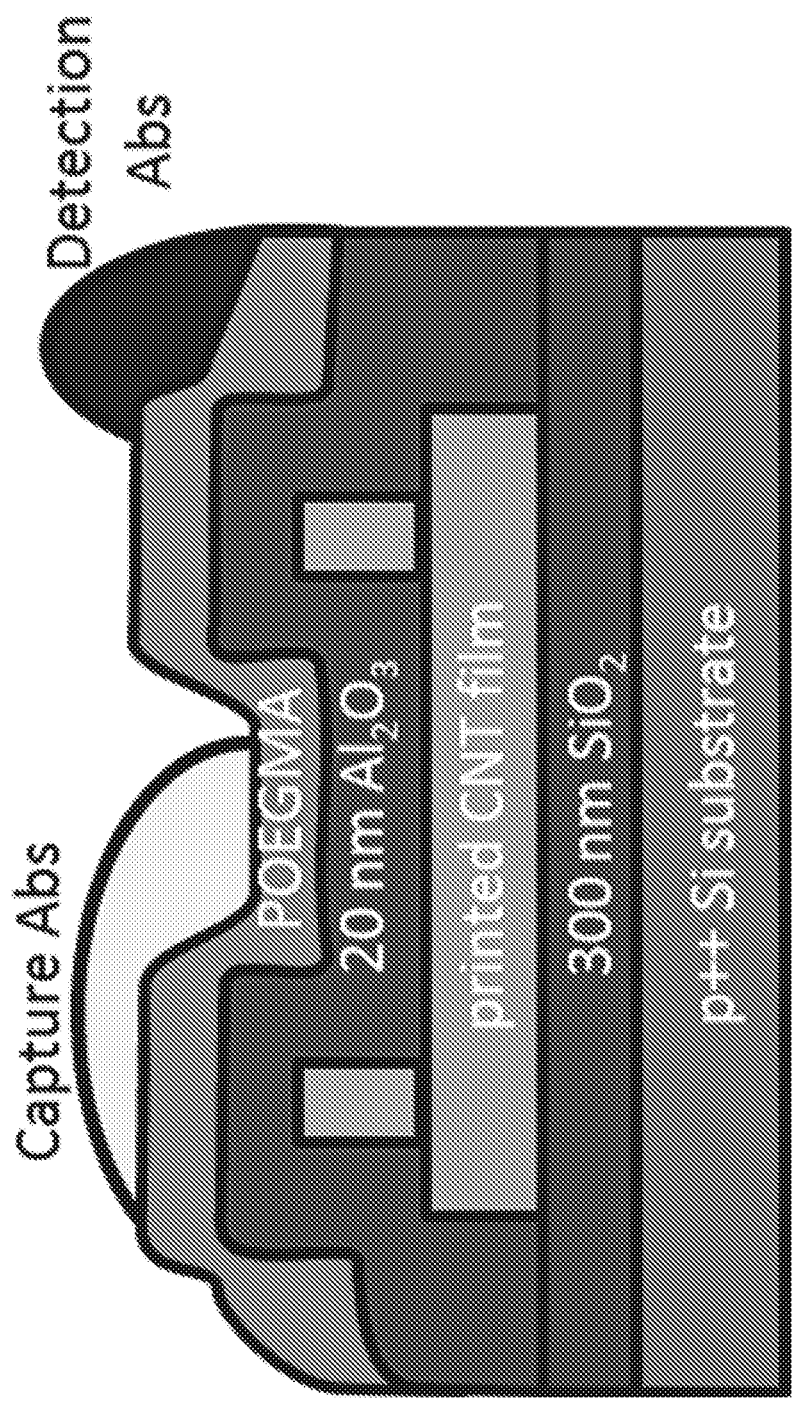
FIG. 15 is a schematic of a sensor including a second dielectric layer positioned in between the non-fouling polymer layer and the carbon nanotube channel, as well as capture and detections agents printed onto the non-fouling polymer layer.

Disclosed herein are sensors that include a multi-layered structure. The sensor includes a conductive substrate, a first dielectric layer, a carbon nanotube channel, a second dielectric layer, a non-fouling polymer layer and at least one capture agent. FIG. 15 shows an embodiment of the sensor, where the conductive substrate serves as the base of the sensor, and the first dielectric layer, carbon nanotube channel, second dielectric layer, and non-fouling polymer layer are positioned above the substrate in that order (e.g., bottom: conductive substrate—top: non-fouling polymer layer). The sensors can be used to accurately detect whether an analyte is present within a sample, e.g., a biological sample. In some embodiments, the sensor can be a field effect transistor sensor.

A. Conductive Substrate

The sensor includes a conductive substrate. The conductive substrate may serve as the base of the sensor. The conductive substrate may act as a gate of the sensor, where voltage is applied. Accordingly, the conductive substrate can be configured to have a voltage applied to it. The conductive substrate may include any suitable material that allows the disclosed sensors to perform their intended function, e.g., the substrate may be any material that can be configured to have a voltage applied thereto, while also being able to electrostatically affect and/or control the carbon nanotube channel. Examples include, but are not limited to, silicon, doped silicon, a III-V group semiconductor substrate, a II-VI group semiconductor substrate, an epitaxially grown silicon-germanium substrate, a glass substrate, a quartz substrate, a metal substrate or a plastic substrate. In some embodiments, the conductive substrate may include p-doped silicon. In some embodiments, the conductive substrate may consist of doped silicon. In some embodiments, the conductive substrate may be p-doped silicon.

The conductive substrate may have a varying thickness. For example, the conductive substrate may have a thickness of from about 10 nm to about 20 µm, such as from about 100 nm to about 10 µm, or from about 500 nm to about 10 µm.

B. Dielectric Layers

The sensor includes a first dielectric layer and a second dielectric layer. The dielectric layers are positioned in different locations of the sensor. The first dielectric layer is positioned on the conductive substrate, and is between the conductive substrate and the carbon nanotube channel. The second dielectric layer is positioned on the carbon nanotube channel, and is between the carbon nanotube channel and the non-fouling polymer layer. The first and second dielectric layers may directly contact each other, but the first dielectric layer may not directly contact the non-fouling polymer layer, and the second dielectric layer may not directly contact the conductive substrate.

The dielectric layers may include any suitable dielectric material known within the art that allows the sensor to perform its intended function. In some embodiments, at least one of the first and second dielectric layers may include a metal oxide. In some embodiments, the first and second dielectric layers may both include a metal oxide. Further, in some embodiments the first and second dielectric layers may each independently consist essentially of a metal oxide. In still further embodiments, the first and second dielectric layers may each independently consist of a metal oxide. In embodiments where the first and second dielectric layers both include a metal oxide, the dielectric layers may include the same metal oxide, or they may include different metal oxides. Examples of metal oxides include, but are not limited to, $SiO_2$, $Sc_2O_3$, $Al_2O_3$, $TiO_2$, $MgO$, $In_2O_3$, $SnO_2$, $ZnO$, $ZnMgO$, or any combination thereof. In some embodiments, the first dielectric layer includes $SiO_2$. In some embodiments, the second dielectric layer may include $Al_2O_3$.

The first and second dielectric layers may each independently have a varying thickness. For example, the first dielectric layer may have a thickness of from about 10 nm to about 500 nm, such as from about 50 nm to about 400 nm or from about 100 nm to about 350 nm. In some embodiments, the first dielectric layer may have a thickness of greater than 10 nm, greater than 50 nm, greater than 100, greater than 150 nm, or greater than 200 nm. In some embodiments, the first dielectric layer may have a thickness of less than 500 nm, less than 450 nm, less than 400 nm, or less than 350 nm.

In addition, the second dielectric layer may have a thickness of from about 5 nm to about 50 nm, such as from about 10 nm to about 40 nm, from about 10 nm to about 30 nm, or from about 10 nm to about 25 nm. In some embodiments, the second dielectric layer may have a thickness of greater than 5 nm, greater than 6 nm, greater than 7 nm, greater than 8 nm, greater than 9 nm, greater than 10 nm, greater than 15 nm, greater than 20 nm, or greater than 25 nm. In some embodiments, the second dielectric layer may have a thickness of less than 50 nm, less than 45 nm, less than 40 nm, less than 35 nm, or less than 30 nm.

In some embodiments, the second dielectric layer may have a thickness less than that of the first dielectric layer. For example, the second dielectric layer may have a thickness of about 20 nm, while the first dielectric layer may have a thickness of about 300 nm.

C. Carbon Nanotube Channel

The sensor includes a carbon nanotube channel. The carbon nanotube channel is positioned on the first dielectric layer, and is in between at least a portion of the first and second dielectric layers. The carbon nanotube channel may be printed onto the first dielectric layer. In some embodiments, the carbon nanotube channel may be a film (and/or transistor film) printed onto the first dielectric layer.

The carbon nanotube channel includes at least one carbon nanotube (CNT), wherein the carbon nanotube can be a semi-conducting CNT. In some embodiments, the carbon nanotube channel may include a plurality of CNTs. For example, the carbon nanotube channel may include greater than 5 CNTs, greater than 10 CNTs, greater than 50 CNTs, or greater than 100 CNTs. The CNTs may include additional elements (e.g., doped CNTs), as long as the CNT still possess characteristics of a semiconductor material. Additional elements include, but are not limited to, boron, nitrogen, iron, zinc, nickel, cadmium, tin, antimony or combinations thereof. The CNT may have a diameter from about 0.5 nm to about 50 nm, wherein the length of the CNT may be from about 0.5 μm to about 1000 μm, or a combination thereof.

The carbon nanotube channel may have a varying thickness. For example, the carbon nanotube channel may have a thickness of from about 1 nm to about 50 nm, such as from about 1 nm to about 25 nm, or from about 1 nm to about 10 nm. In some embodiments, the carbon nanotube channel may have a thickness of greater than 1 nm, greater than 2 nm, greater than 3 nm, or greater than 4 nm. In some embodiments, the carbon nanotube channel may have a thickness of less than 50 nm, less than 40 nm, less than 30 nm, less than 20 nm, or less than 10 nm.

In addition, the sensor can include at least two electrodes positioned on the carbon nanotube channel. The electrodes may include a source electrode and a drain electrode, and the source and drain electrodes may be positioned at opposite ends of the carbon nanotube channel. The electrodes may include any suitable material known in the art that allows the sensor to perform its intended function. Examples of electrode materials include, but are not limited to, platinum, gold, silver, chrome, copper, aluminum, nickel, palladium, titanium, molybdenum, lead, iridium, rhodium, cobalt, tungsten, tantalum, erbium, ytterbium, samarium, yttrium, gadolinium, terbium, cerium or any combination thereof. In some embodiments, the electrodes may include silver. In some embodiments, the electrodes may be both silver.

D. Non-Fouling Polymer Layer

The sensor includes a non-fouling polymer layer that can decrease non-specific binding and/or adsorption of non-target analytes to the sensor. Non-fouling, as used herein with respect to the polymer layer, relates to the inhibition (e.g., reduction or prevention) of growth of an organism as well as to non-specific or adventitious binding interactions between the polymer layer and an organism or biomolecule (e.g., cell, protein, nucleotide, etc.). The non-fouling polymer layer is positioned on the second dielectric layer, and does not directly contact the carbon nanotube channel. As mentioned above, it has been found that a more robust and reliable sensor can be provided when the non-fouling polymer layer does not directly contact the carbon nanotube channel, but rather has a second dielectric layer positioned between these two layers.

The non-fouling property of the polymer layer is due in part to the inclusion of poly oligo(ethylene glycol) methyl methacrylate (POEGMA). POEGMA can instill a non-fouling characteristic to the polymer layer due to its composition and the structure that it has on the second dielectric's surface. For example, POEGMA can form a brush-like structure on the second dielectric layer. The brush-like structure of POEGMA can be achieved through suitable polymerization conditions of growing the polymer on the surface of the second dielectric material, which are described in more detail below.

POEGMA can have different terminal functional groups. In some embodiments, POEGMA may be alkoxy terminated. In some embodiments, POEGMA can be hydroxy terminated, methoxy terminated, or ethoxy terminated homopolymers. In other embodiments, POEGMA can be a copolymer of alkoxy-terminated POEGMA and hydroxy-terminated POEGMA. In some embodiments, the POEGMA can be a combination of the different aforementioned homo- and copolymers of POEGMA. In some embodiments, POEGMA can be the only polymer included in the non-fouling polymer layer.

POEGMA may have varying ethylene glycol repeat units within its polymer chains. For example, POEGMA may have an ethylene glycol repeat unit of from about 2 to about 20, such as from about 2 to about 10 or from about 2 to about 4. In some embodiments, POEGMA can have an ethylene glycol repeat unit of greater than 1, greater than or equal to 2, greater than or equal to 3, greater than or equal to 4, or greater than or equal to 5. In some embodiments, POEGMA can have an ethylene glycol repeat unit of less than or equal to 20, less than or equal to 18, less than or equal to 16, less than or equal to 14, less than or equal to 12, or less than or equal to 10.

Generally, POEGMA brush-like structure can be formed in a very controlled manner, thereby allowing for precise control over the final thickness of the non-fouling polymer layer, as well as the density at which it is applied to the second dielectric layer. For example, the non-fouling polymer layer may have a thickness of from about 5 nm to about 150 nm, such as from about 10 nm to about 125 nm or from about 10 nm to about 100 nm. In some embodiments, the non-fouling polymer layer may have a thickness of greater than 5 nm, greater than 10 nm, greater than 20 nm, or greater than 30 nm. In addition, the non-fouling polymer layer may have a density (on the second dielectric surface) of from about 10 mg/m to about 500 mg/m, such as from about 20 mg/m to about 200 mg/m or from about 40 mg/m to about 100 mg/m.

It has been found that POEGMA not only has non-fouling properties, but also can be used as part of a sensor device without impeding its performance. For example, POEGMA can have a permissitivity (when hydrated) of from about 50 to about 80, such as from about 55 to about 70, or from about 60 to about 70. In some embodiments, the POEGMA can have a permissitivity (when hydrated) of about 69. In addition, the POEGMA may have a break voltage of greater than 100 kV/cm, greater than 125 kV/cm, greater than 150 kV/cm, greater than 175 kV/cm, or greater than 180 kV/cm. In some embodiments, the POEGMA may have a break voltage of about 183 kV/cm.

In addition to POEGMA, the non-fouling polymer layer may include other components and/or compounds that would aid in the overall function of the sensor. Further description of the non-fouling polymer layer can be found in International Application Publication WO 2017/015132, which is incorporated herein by reference in its entirety.

E. Capture Agent

The sensor includes at least one capture agent that is adapted to specifically bind to a target analyte, the capture agent being bound to the non-fouling polymer layer. The capture agent does not directly contact the carbon nanotube channel. For example, the capture agent can be separated from the carbon nanotube channel by a distance of greater than 5 nm, greater than 10 nm, greater than 20 nm, greater than 50 nm, or greater than 100 nm.

The capture agent can be printed onto the non-fouling polymer layer, which can allow the capture agent to be non-covalently bound to the polymer layer. In addition, printing of the capture agent can allow for the capture agent to be precisely located on the polymer layer, and in some instance the capture agent can be confined to specific locations of the non-fouling polymer layer, e.g., a capture region. Methods of applying the capture agent to the polymer layer are described in greater detail below.

The number of capture agents and/or regions can vary widely and can depend on several factors including the size and shape of the sensor, the intended use of the sensor (e.g., a point-of-care diagnostic, a panel array, protein, tissue, cellular, chemical compounds, antibody, carbohydrate, etc.), and the like. The capture agent is generally one member of a specific binding pair, where the capture agent is adapted to bind to a target analyte. Examples of suitable capture agents include, but are not limited to, antigens, antibodies, peptides, proteins, nucleic acids, nucleic acid and/or peptide aptamers, ligands, receptors, and the like. In some embodiments, the capture agent is an antibody, such as a monoclonal or a polyclonal antibody.

In some embodiments, the capture agent can comprise a biomarker associated with any disease, disorder, or biological state of interest. Accordingly, the selection of the capture agent can be driven by the intended use or application of the sensor and methods described herein and can include any molecule known to be associated with a disease, disorder, or biological state of interest, or any molecule suspected of being associated with a disease, disorder, or biological state of interest.

In some embodiments, the capture agent can comprise a biomarker associated with a microbial infection, examples include, but are not limited to: Anthrax, Avian influenza, Botulism, Buffalopox, Chikungunya, Cholera, Coccidioidomycosis, Creutzfeldt-Jakob disease, Crimean-Congo haemorrhagic fever, Dengue fever, Dengue haemorrhagic fever, Diphtheria, Ebola haemorrhagic fever, Ehec (*E. coli* 0157), Encephalitis, Saint-Louis, Enterohaemorrhagic *Escherischia coli* infection Enterovirus, Foodborne disease, Haemorrhagic fever with renal syndrome, Hantavirus pulmonary syndrome, Hepatitis, Human Immunodeficiency Virus (HIV), Influenza, Japanese encephalitis, Lassa fever, Legionellosis, Leishmaniasis, Leptospirosis, Listeriosis, Louseborne typhus, Malaria, Marburg haemorrhagic fever, Measles, Meningococcal disease, Monkeypox, Myocarditis Nipah virus, O'Nyong-Nyong fever, Pertussis, Plague, Poliomyelitis, Rabies, Relapsing fever, Rift Valley fever, Severe acute respiratory syndrome (SARS), Shigellosis, Smallpox vaccine—accidental exposure, Staphylococcal food intoxication, Syphilis, Tularaemia, Typhoid fever, West Nile virus, and Yellow fever.

Additionally, the biomarker may be associated with obesity. For example, the biomarker may be leptin.

F. Detection Agent

The sensor may further include at least one detection agent that is adapted to specifically bind to a target analyte or a binding complex formed by the target analyte and the capture agent. Similar to the capture agent, the detection agent may be precisely printed at discrete locations of the polymer layer. In some embodiments, the regions may include the detection agent also include an excipient and are denoted as labile regions. Generally, the description regarding the capture agent (and what it can include) can be applied to the detection agent, except that the detection agent (when present) becomes soluble after a certain amount of time following contacting the sensor with a sample. For the purposes of brevity, this description will not be repeated here.

In some embodiments, the capture agent can remain non-covalently bound to the polymer layer (e.g., polymer brush) upon contact with a sample such as a biological fluid, buffer, or aqueous solvent, while the excipient present in the labile region can absorb in to the polymer brush and block absorption of the detection agent. Accordingly, when exposed to a sample, such as a sample comprising a biological fluid, the detection agent can be solubilized and released into the sample, and can bind to an analyte of interest. The excipient can also further stabilize the detection agent during storage.

In some embodiments, the excipient can be a molecule or a combination of molecules that is selected to allow a stable, but non-permanent, association between the detection agent and the polymer. In some embodiments the excipient can be partially soluble, substantially soluble or soluble in an aqueous solution (e.g., buffer, water, sample, biological fluid, etc.). In such embodiments, the excipient can be selected from the non-limiting examples of salts, carbohydrates (e.g., sugars, such as glucose, fucose, fructose, maltose and trehalose), polyols (e.g., mannitol, glycerol, ethylene glycol), emulsifiers, water-soluble polymers, and any combination thereof. Such excipients are well known in the art and can be selected based on the interaction between the excipient and detection agent, the excipient and the polymer, the solubility of the excipient in a particular medium, and any combination of such factors. In some embodiments, the excipient can include PEG.

In addition, the detection agent may be conjugated or bound to a compound and/or molecule that can further aid in overall detection of the target analyte. For example, the detection agent may be an antibody conjugated to a compound and/or molecule that can enhance the change in an electrical property upon binding to the target analyte.

G. Additional Components

The sensor can include other components and/or additional layers that can be useful for sensor performance. The sensor can further include an electronic circuit that is configured to measure an electrical property of the carbon nanotube channel. Electrical properties include resistivity, capacitance, impedance, inductance or a combination thereof.

In some embodiments, the device can further comprise an agent to demarcate a patterned region on the polymer layer, such that a fluid (e.g., a biological fluid) will remain confined to a specified region on the polymer layer such that it contacts the capture region and/or the labile region. Such an agent can be, for example, a hydrophobic ink printed on the polymer layer prior to the deposition of the capture agent and/or the components of the labile region. Alternatively, the agent can be a wax. In other embodiments, the sample can be contained or directed on the device through selection of an appropriate geometry and/or architecture for the substrate, for example, a geometry that allows the sample to diffuse to the regions comprising the capture agent and the components of the labile spot. In some embodiments, the substrate can include a well, or a series of interconnected wells.

In some embodiments, the sensor may include one or more dams. Dams may be provided to separate one or more spots and/or regions from one or more other spots and/or regions. Dams may be water soluble and made out of any material known to those skilled in the art. Dams may be disposed on the sensor between the capture agent and the detection agent. Dams may include a water-soluble salt, water-soluble sugar, a water-soluble polymer, or any combination thereof. Suitable examples of materials from which a dam may be constructed include, but are not limited to, a phosphate salt, a citrate salt, trehalose, polyvinyl alcohol, polyethylene glycol, or any combination thereof.

In some embodiments, e.g., when the biological fluid is a blood sample, the labile region can comprise an anticoagulant to prevent the blood from clotting. Exemplary anticoagulants can include, but are not limited to, vitamin K antagonists such as Coumadin, heparins, and low molecular weight heparins.

In some embodiments, the sensor can further comprise regions printed with control agents. For example, when the detection agent comprises an anti-human antibody, control capture regions of human IgG can be printed alongside the capture regions to verify the activity of the anti-human detection antibody and to normalize the signal from the detection moiety.

3. Methods of Making the Sensors

Disclosed herein are methods of making the sensors. The conductive substrate may be provided by any traditional means known within the art, or otherwise may be purchased commercially. The dielectric layers may be applied to their respective supporting material(s) and/or layer(s) (e.g., the first dielectric layer applied to the conductive substrate) by any suitable means known with the art. For example, the first dielectric layer may be thermally grown as a layer onto a surface of the conductive substrate. In some embodiments, the conductive substrate is plasma treated prior to functionalizing the surface with the first dielectric layer. The second dielectric layer may be applied to the carbon nanotube channel (and in some embodiments applied to the carbon nanotube channel and the first dielectric layer) by atomic layer deposition.

The carbon nanotube channel may be applied to the first dielectric layer through a printing process. In some embodiments, the CNTs may be dispersed in a solvent (e.g., toluene) using a surfactant prior to printing onto the surface of the first dielectric layer. This dispersion may also be referred to as a CNT ink. The CNT ink may be printed using a sheath flow of about 30 sccm to about 45 sccm, an atomizer flow of about 15 sccm to about 30 sccm and an atomizer current of about 400 mA to about 500 mA. In some embodiments, the ink can be printed using a sheath flow of about 40 sccm, an atomizer flow of about 23 sccm and an atomizer current of about 470 mA. Following printing of the CNT channel, the intermediate sensor (e.g., conductive substrate-first dielectric layer-carbon nanotube channel) may be heated at a temperature of from about 130° C. to 160° C. for about 5 minutes to about 15 minutes. In some embodiments, the immediate sensor is heated at about 150° C. for about 10 minutes.

In addition, electrodes may be printed onto the carbon nanotube channel. For example, 40 wt % Ag nanoparticles (diameter 20 nm) dispersed in a solvent mixture of xylene and terpineol at a volume ratio of 9 to 1 respectively may be printed onto the carbon nanotube channel as silver lines. In some embodiments, the Ag ink can be printed using a sheath flow of about 25 sccm, an atomizer flow of about 20 sccm and an atomizer current of about 415 mA. The silver lines may then be placed in an oven at about 200° C. to sinter the nanoparticles together in order to form conducting lines.

The non-fouling polymer layer including POEGMA can be formed on the surface of the second dielectric layer using radical polymerization techniques, such as catalytic chain transfer polymerization, initiator mediated polymerization (e.g., photo initiator mediated polymerization), free radical polymerization, stable free radical mediated polymerization (SFRP), atom transfer radical polymerization (ATRP), and reversible addition-fragmentation chain transfer (RAFT) polymerization.

For example, free radical polymerization of monomers to form brush polymers can be carried out in accordance with known techniques, such as described in U.S. Pat. Nos. 6,423,465, 6,413,587 and 6,649,138, U.S. Patent Application No. 2003/0108879, all of which are incorporated by reference herein in their entirety. Atom transfer radical polymerization of monomers to form brush polymers can also be carried out in accordance with known techniques, such as described in U.S. Pat. Nos. 6,541,580 and 6,512,060, U.S. Patent Application No. 2003/0185741, all of which are incorporated by reference herein in their entirety. Further description of forming POEGMA brush-like structures on a substrate and/or layer can be found in International Application Publication WO 2017/015132, which is incorporated herein by reference in its entirety.

In some embodiments, the polymer layer can be formed by surface-initiated ATRP (SI-ATRP) of oligo(ethylene glycol)methyl methacrylate (OEGMA) to form a poly (OEGMA) (POEGMA) film. In some embodiments, the polymer layer is a functionalized POEGMA film prepared by copolymerization of a methacrylate and alkoxy terminated OEGMA. Suitably, the POEGMA polymer can be formed in a single step.

In addition to POEGMA, other types of monomers and/or polymers can be included within the growth of the polymer layer. Any suitable core vinyl monomer polymerizable by the processes discussed above can be used, including but not limited to styrenes, acrylonitriles, acetates, acrylates, methacrylates, acrylamides, methacrylamides, vinyl alcohols, vinyl acids, and combinations thereof.

Prior to deposition of further components (e.g. the capture agent) onto the polymer layer, the polymer layer can be dry or at least macroscopically dry (that is, dry to the touch or dry to visual inspection, but retaining bound water or water of hydration in the polymer layer). For example, to enhance immobilization of a capture agent, the polymer layer can suitably retain bound water or water of hydration, but not bulk surface water. If the polymer layer (on the sensor) has been stored in desiccated form, bound water or water of hydration can be reintroduced by quickly exposing the polymer layer to water (e.g., by dipping in to water) and subsequently blow-drying the surface (e.g., with a nitrogen or argon jet). Alternatively, bound water or water of hydration can be reintroduced by exposing the polymer layer to ambient air for a time sufficient for atmospheric water to bind to the polymer layer.

The capture agent can be deposited on the polymer layer by any suitable technique such as microprinting or microstamping, including piezoelectric or other forms of non-contact printing and direct contact quill printing. When the capture agent is printed on to the polymer layer, it can suitably be absorbed into the polymer layer such that it remains bound when the device is exposed to a fluid, such as a biological fluid. The brush polymer can also provide a protective environment, such that the capture agent remains stable when the device is stored. For example, in embodiments in which the capture agent is a peptide or protein, such as an antigenic protein or an antibody, a brush polymer layer can protect the capture agent against degradation, allowing the device to be stored under ambient conditions.

When an array is formed by the deposition of multiple capture agents at discrete locations on the polymer layer, probe densities of 1, 3, 5, 10, 100 or up to 1000 probe locations per $cm^2$ can be made. Non-contact arrays can be used in the deposition step to produce arrays having up to 1,000,000 probe locations per $cm^2$. For example, using dip-pen nanolithography, arrays with up to 1 billion discrete probe locations per $cm^2$ can be prepared. It will be appreciated that the specific molecular species at each capture spot can be different, or some can be the same (e.g., to provide some redundancy or control), depending upon the particular application, as described herein.

As describe above, the capture agent can be printed onto the polymer layer to form a capture region. The capture region(s) can be arranged in any particular manner and can comprise any desirable shape or pattern such as, for example, spots (e.g., of any general geometric shape), lines, or other suitable patterns that allow for identification of the capture region on the surface of the polymer and substrate. In some embodiments, a plurality of capture agents can be arranged in a predetermined pattern such that the identity of the capture agent is associated with a specific location on the sensor.

The detection agent and the excipient can be deposited on the polymer layer by any suitable technique such as microprinting or microstamping (as described above regarding the capture agent), including piezoelectric or other forms of non-contact printing and direct contact quill printing. A mixture of the detection agent and the excipient can be deposited simultaneously, or the excipient can be deposited prior to the detection agent.

After deposition of the capture agent, detection agent, excipient and other optional components, the device can be optionally dried, e.g., by mild desiccation, blow drying, lyophilization, or exposure to ambient air at ambient temperature, for a time sufficient for the article to be dry or at least macroscopically dry as described above. Once the device is dry or at least macroscopically dry, it can be sealed in a container (e.g., such as an impermeable or semipermeable polymeric container) in which it can be stored and shipped to a user. Once sealed in a container, the device can have, a shelf life of at least 2 months, or upwards to 1 year, when stored at a temperature of 25° C. (e.g., without loss of more than 20, 30 or 50 percent of binding activity).

4. Methods of Using the Sensors

Also disclosed herein are methods of using the sensors. The sensors can be used in a variety of different applications, and in particular, applications related to detection of a specific analyte within a sample. For example, the sensors can be used to detect the presence or absence of an analyte. The method may include contacting the sensor, as described above, with a sample. As used herein, the term "sample" or "biological sample" relates to any material that is taken from its native or natural state, so as to facilitate any desirable manipulation or further processing and/or modification. A sample or a biological sample can comprise a cell, a tissue, a fluid (e.g., a biological fluid), a protein (e.g., antibody, enzyme, soluble protein, insoluble protein), a polynucleotide (e.g., RNA, DNA), a membrane preparation, and the like, that can optionally be further isolated and/or purified from its native or natural state. A "biological fluid" refers to any fluid originating from a biological organism. Exemplary biological fluids can include, but are not limited to, blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid. A biological fluid can be in its natural state or in a modified state by the addition of components such as reagents, or removal of one or more natural constituents (e.g., blood plasma). A sample or biological sample can be, for example, blood, plasma, lymph, viral, bacterial, a human sample, a diseased human sample, an animal sample, a disease animal sample, saliva, mucus, cerebral spinal fluid, synovial fluid, stomach fluid, intestinal fluid, cytoplasmic fluid, or other type of sample.

After contacting the sensor with a sample, an electrical property of the carbon nanotube channel can be measured, such as resistivity, capacitance, impedance, inductance or a combination thereof. The presence (or absence) of the analyte can then be determined through a change in the electrical property of the carbon nanotube channel upon binding of the analyte to the capture agent. In some embodiments, the sample added to the sensor does may not directly contact the carbon nanotube channel.

In some embodiments, measuring the electrical property may be performed prior to the sample being added and up to 30 minutes after the sample is added. In some embodiments, determining the presence of the analyte may include comparing the electrical property measurement of the carbon nanotube channel prior to adding the sample to the electrical property measurement of the carbon nanotube channel after a certain amount of time following addition of the sample (e.g., after 1 minute, after 5 minutes, after 10 minutes, after 30 minutes, etc.).

5. EXAMPLES

The compositions and methods of the invention will be better understood by reference to the following examples, which are intended as an illustration of and not a limitation upon the scope of the invention.

Example 1

Synthesis and Characterization of Nonfouling POEGMA on Metal Oxide Surfaces Experimental Atomic Layer Deposition: Atomic layer deposition (ALD) was employed to deposit conformal thin films with atomic-scale precision. Metal precursors and oxygen sources are sequentially introduced to the chamber, leading to deposition of dielectric materials with monolayer-by-monolayer control. In this example, Savannah S200 ALD system by Ultratech/CambridgeNanotech (Waltham, Mass.) was used. Prior to ALD, silicon wafers were thoroughly cleaned with piranha (3:1 sulfuric acid: 30% hydrogen peroxide), rinsed copiously with deionized water and then isopropyl alcohol, and then gently blown dry with $N_2$ gas. The operating temperature for ALD was 150° C. For all runs, the Savannah S200 ALD system was first allowed to stabilize for at least 10 minutes prior to performing coating steps. The specific system settings and recipe used for each metal oxide dielectric material are summarized in Table 1 (values reflect experimental conditions using the Savannah S200 ALD system).

Surface functionalization with APTES and installation of bromide initiator: Unless otherwise stated, steps were performed under ambient conditions. The oxide samples described above were immersed in a 10% solution of 3-aminopropyltriethoxysilane (Gelest, Inc.; Morrisville, Pa.) in anhydrous ethanol overnight, and subsequently rinsed with ethanol and then three times with deionized water. Chips were spun dry and then cured in an oven at 120° C. for 2 h. Next, the chips were cooled to room temperature then placed in a dichloromethane solution containing 1% α-bromoisobutyryl bromide and 1% triethylamine (Sigma Aldrich; St. Louis, Mo.) for 45 min, followed by rinsing in fresh dichloromethane, then ethanol, and then three times in deionized water. The chips were spun dry at 150 rcf for 6 min, and then allowed to dry under ambient conditions.

Preparation of polymerization solution: A solution composed of 350 mL deionized water, 25 mg copper (II) bromide, 50 microliters of HMTETA, and 55 grams of inhibitor-free poly(ethylene glycol) methyl ether methacrylate (Mn≈300) were degassed by He-sparging for 3 hours.

Surface-initiated atom-transfer radical polymerization: Under an Ar environment, 600 mg of sodium ascorbate was added to the polymerization solution described above and gently stirred for 1 min, at which point the solution changed color from blue to violet. The chips were then placed in this solution for polymerization (without stirring). After allowing polymerization to proceed for the desired time, chips were rinsed three times with deionized water, then centrifuged at 150 rcf for 6 minutes and allowed to dry under ambient conditions. The thickness of POEGMA brush was determined by reflective-mode ellipsometry, as described below.

SI-ATRP of POEGMA on Gold: Si chips were coated with 10 nm of Au using electron-beam evaporation (Kurt J. Lesker Company, Jefferson Hills Pa.). Au-coated chips were immersed in a 10% solution of Bis[2-(2-bromoisobutyryloxy)undecyl] disulfide (Sigma-Aldrich; St. Louis, Mo.) in anhydrous ethanol overnight, and subsequently rinsed with ethanol and then three times with deionized water. The chips were centrifuged and then allowed to dry in ambient conditions. Subsequently, steps were performed as described above to grow POEGMA brushes.

Reflective Mode Ellipsometry: The thickness of thin films was measured using an M-88 spectroscopic ellipsometer (J.A. Woollam Co) at angles of 65, 70, and 75 degrees at wavelengths of 400 to 800 nm. The thickness of the layers underlying the POEGMA films were each determined experimentally based on the optical constants of these materials provided in the instrument software, and were then used to build a model. The POEGMA film thicknesses were then determined using a Cauchy layer algorithm. For all ellipsometric measurements, the chose thickness was for which the mean standard error between the predicted response from the model and the experimental response from the sample reached a global minimum. Only those data that yielded good fitting results (mean square error≤0.9) were used to determine film thicknesses.

X-ray Photoelectron Spectroscopy: All XPS experiments were performed on an AXIS Ultra photoelectron spectrometer (Kratos Analytical, NY) operating at 15 kV and 10 mA using monochromatic Kα1 x-rays. The x-ray spot size was 400 μm (full-width at half maximum). Survey scans and high-resolution core-level spectra were recorded with the following pass energy, energy step, dwell time, and number of sweeps: survey spectra—160 eV, 1 eV, 200 msec, and 10 sweeps; high-resolution core-level spectra—20 eV, 0.1 eV,

TABLE 1

| | Growth parameters for atomic layer deposition of metal oxide dielectrics. | | | | | |
|---|---|---|---|---|---|---|
| | Metal precursor | | Oxygen source | | Time between pulses (sec) | Deposit rate (nm/pulse) |
| Coating | Material | Step (msec) | Material | Step (sec) | | |
| $Al_2O_3$ | Tri-methylaluminum | 15 | $H_2O$ | 15 | 20 | 0.11 |
| $TiO_2$ | Tetrakis(dimethylamido)-Ti | 100 | $H_2O$ | 15 | 20 | 0.06 |
| $ZrO_2$ | Tetrakis(dimethylamido)-Zr | 200 | $H_2O$ | 15 | 30 | 0.1 |

269.7 msec, and 20 sweeps. The operating pressure of the instrument was ~1×10$^{-8}$ Torr. The spectral data were analyzed using CasaXPS software.

Electrical Characterization of POEGMA: Parallel plate capacitors with an area of 2 mm×2 mm were fabricated by growing POEGMA on p++Si wafers with a 10.4 nm overlayer of thermal SiO$_2$, and then utilizing a shadow mask to deposit 5 nm Ti (adhesion layer) and 30 nm Au top contacts with a custom-built Kurt J. Lesker electron-beam evaporator system. The capacitance-voltage (C-V) measurements were performed using an Agilent (Keysight Technologies) B1500A Semiconductor Parameter Analyzer connected via triaxial cables to a Lakeshore CRX 6.5K cryogenic probe station, where one probe was placed on the top contact and a second probe was connected to a back-gated chuck upon which the sample was placed. C-V measurements were obtained at frequencies of 1 MHz, 100 kHz, and 10 kHz from multiple capacitors on the same chip. In order to compare C-V measurements for hydrated POEGMA versus dried POEGMA, characterization was first performed on a dry sample, and then the chip was placed in 1× PBS buffer for 5 min to hydrate the POEGMA. The back of the sample was then dried using a gentle stream of nitrogen gas, and the C-V measurement process was repeated. Finally, the hydrated sample was dried under overnight under vacuum, and a final C-V measurement was obtained and the permittivity extracted once again. For further characterization, a breakdown of the POEGMA was obtained by growing POEGMA on a patterned gold electrode and then depositing a 5 nm Ti adhesion layer and a 30 nm Au top contact using a shadow mask, and the breakdown voltage was determined by measuring current density versus electric field.

Results and Discussion

The high-κ metal oxide dielectrics were fabricated as 10 nm thick layers using atomic layer deposition (ALD) onto Si wafers. The SiO$_2$ was thermally deposited as a 20 nm layer on a Si wafer. The layer-by-layer control offered by ALD allows ultra-thin films of just a few nanometers to be fabricated in a highly reproducible and precise manner, and is widely used in semiconductor manufacturing, especially for emerging electronic architectures with spatial demands below the 100 nm regime. Hence, these dielectric layers offer the most relevant surface for establishing a biointerfacial film that will serve to both protect the underlying CMOS structures from liquid biological environments and preserve the CMOS operation so that it can be used in conjunction with the biointerfacial film for biomolecular detection.

A summary of the synthesis route for the biointerfacial POEGMA brushes fabricated on metal oxide dielectric surfaces is shown in FIG. 1. The approach relies on surface-initiated atom transfer radical polymerization (SI-ATRP) to grow POEGMA from oxide surfaces that were pre-functionalized with an ATRP initiator, using a subtype of SI-ATRP that utilizes an aqueous environment and activators regenerated by electron transfer (ARGET). This approach was used as it produces films with tunable thickness, requires only small amounts of transition metal catalyst, uses an environmentally-friendly reducing agent (sodium ascorbate) that drastically reduces the requirements for tedious deoxygenation procedures, and is performed in water (rather than organic solvent) as the reaction medium. Combined, these features are attractive for reducing production costs and processing complications, especially when producing POEGMA films at scale.

Figure 2:
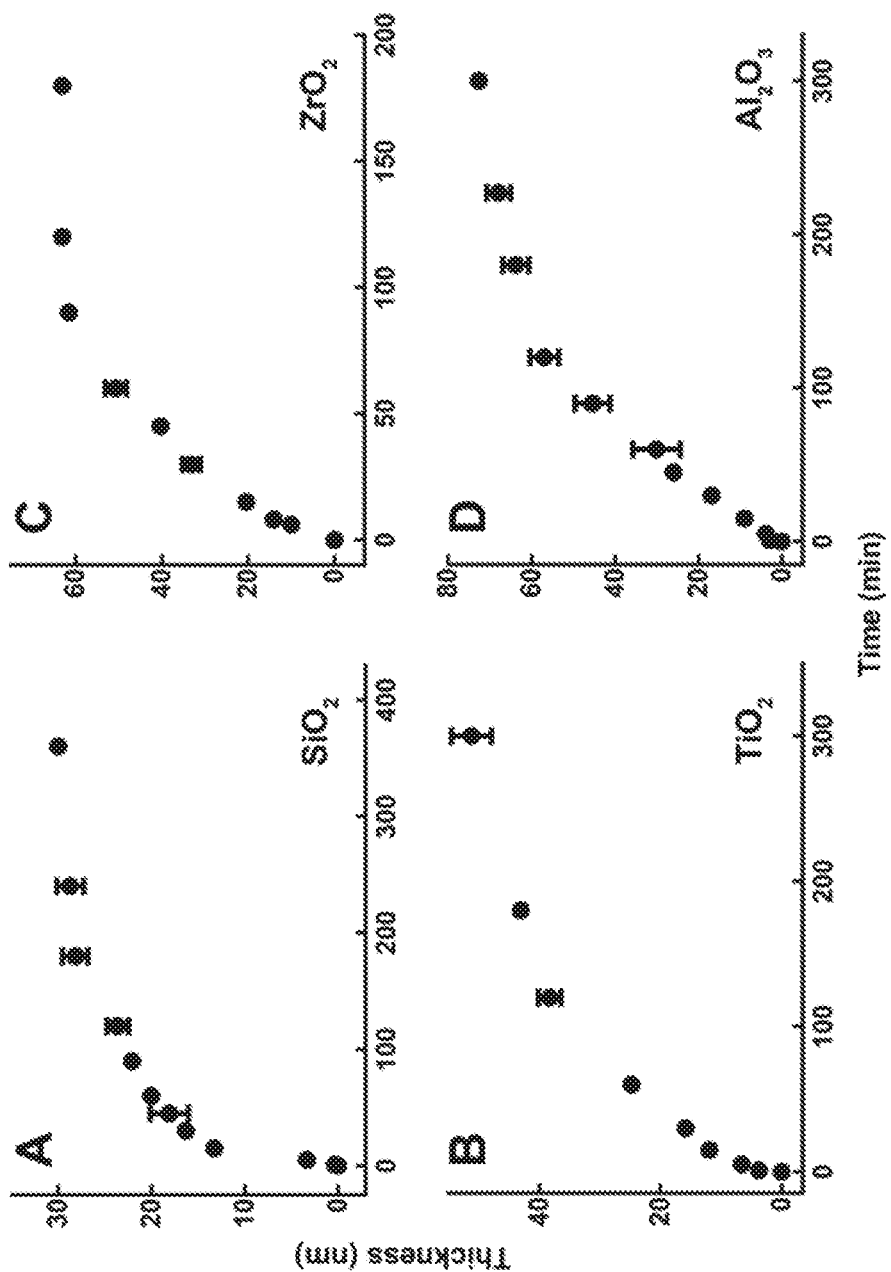
FIG. 2 is a set of graphs showing growth behavior of POEGMA brushes grown by SI-ATRP on metal oxides. POEGMA brush growth was measured by reflective mode ellipsometry at the indicated timepoints for (A) Si/SiO$_2$, (B) TiO$_2$, (C) ZrO$_2$, and (D) Al$_2$O$_3$.
Figure 3:
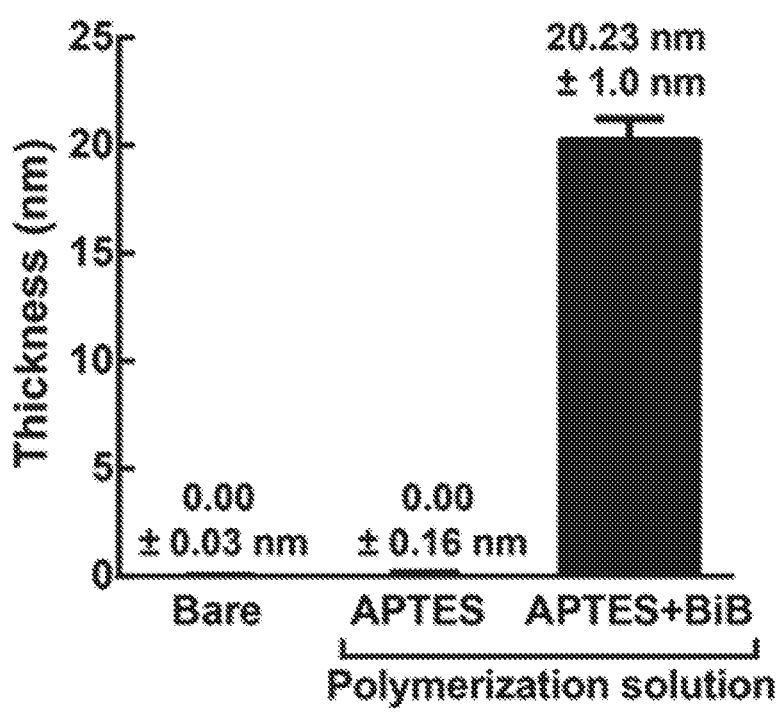
FIG. 3 is a graph showing the effect of bromide initiator on POEGMA brush growth.
Figure 4A:
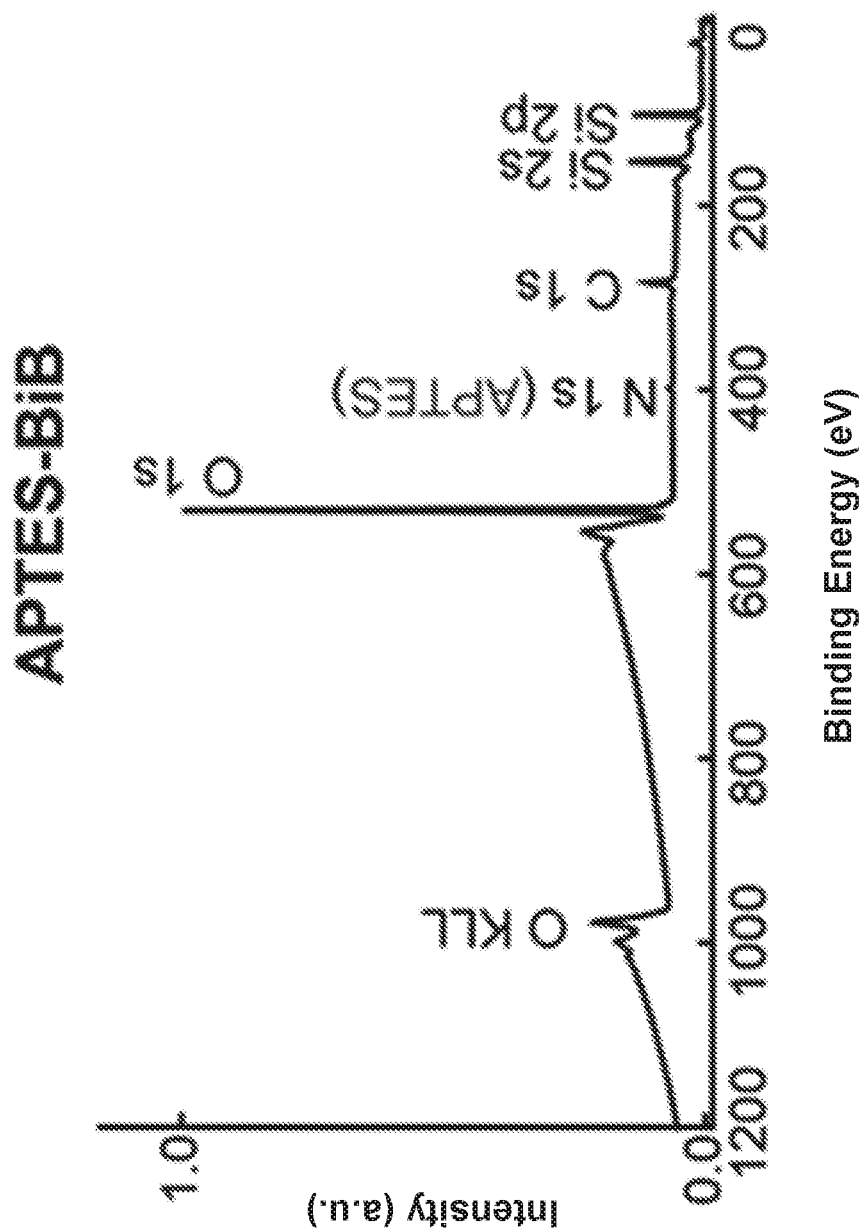
FIG. 4 A-D is a set of graphs showing X-ray photoelectron spectra prior to and after SI-ATRP on metal oxides. (A & B): survey spectra of initiator-grafted (APTES-BiB) surfaces on Si/SiO$_2$ and TiO$_2$, respectively. (C & D): survey spectra following SI-ATRP of POEGMA brushes. Insets: High resolution C1s spectra following SI-ATRP, showing peaks consistent with POEGMA brushes following peak fitting.
Figure 4B:
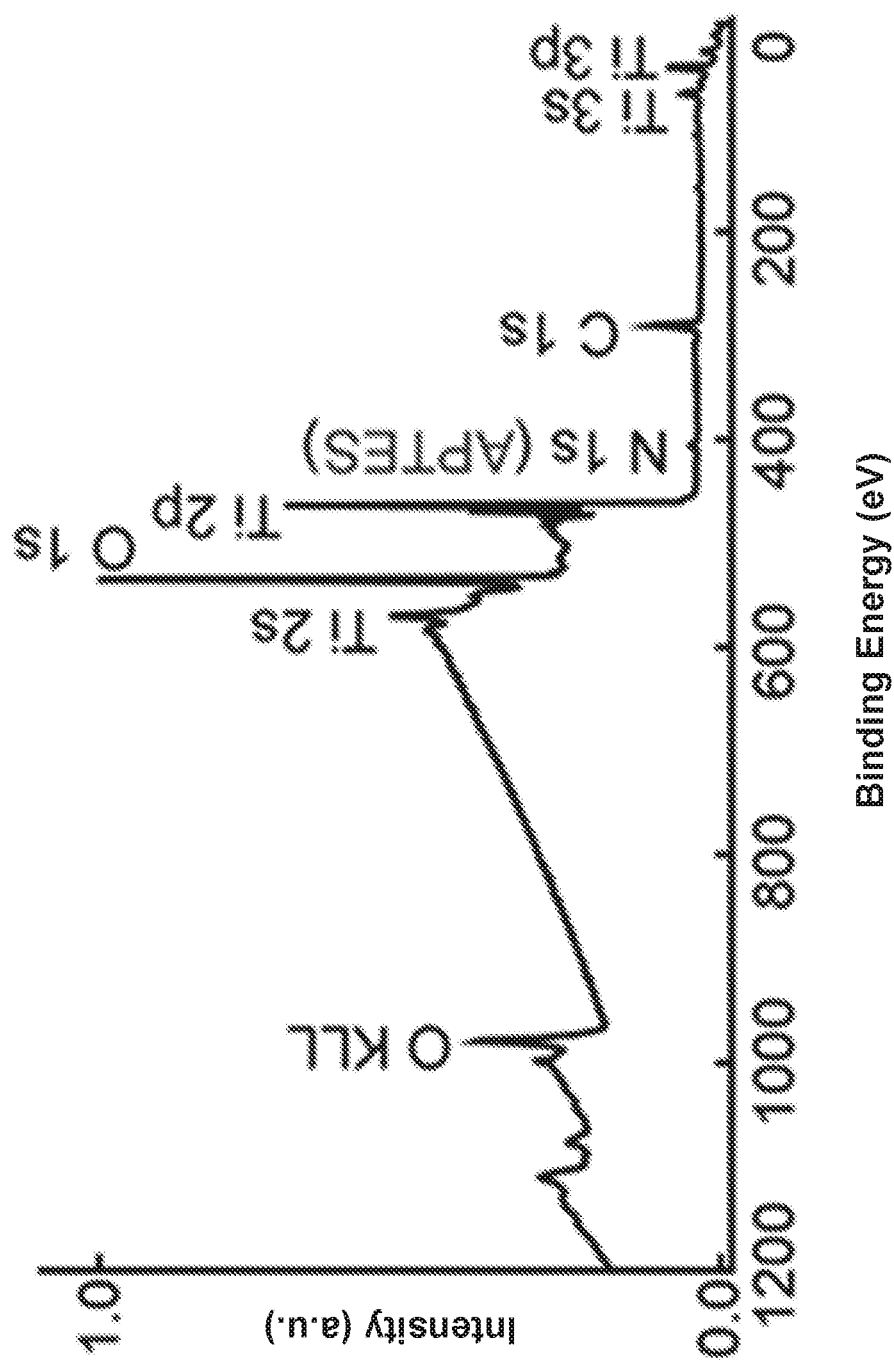
Figure 4C:
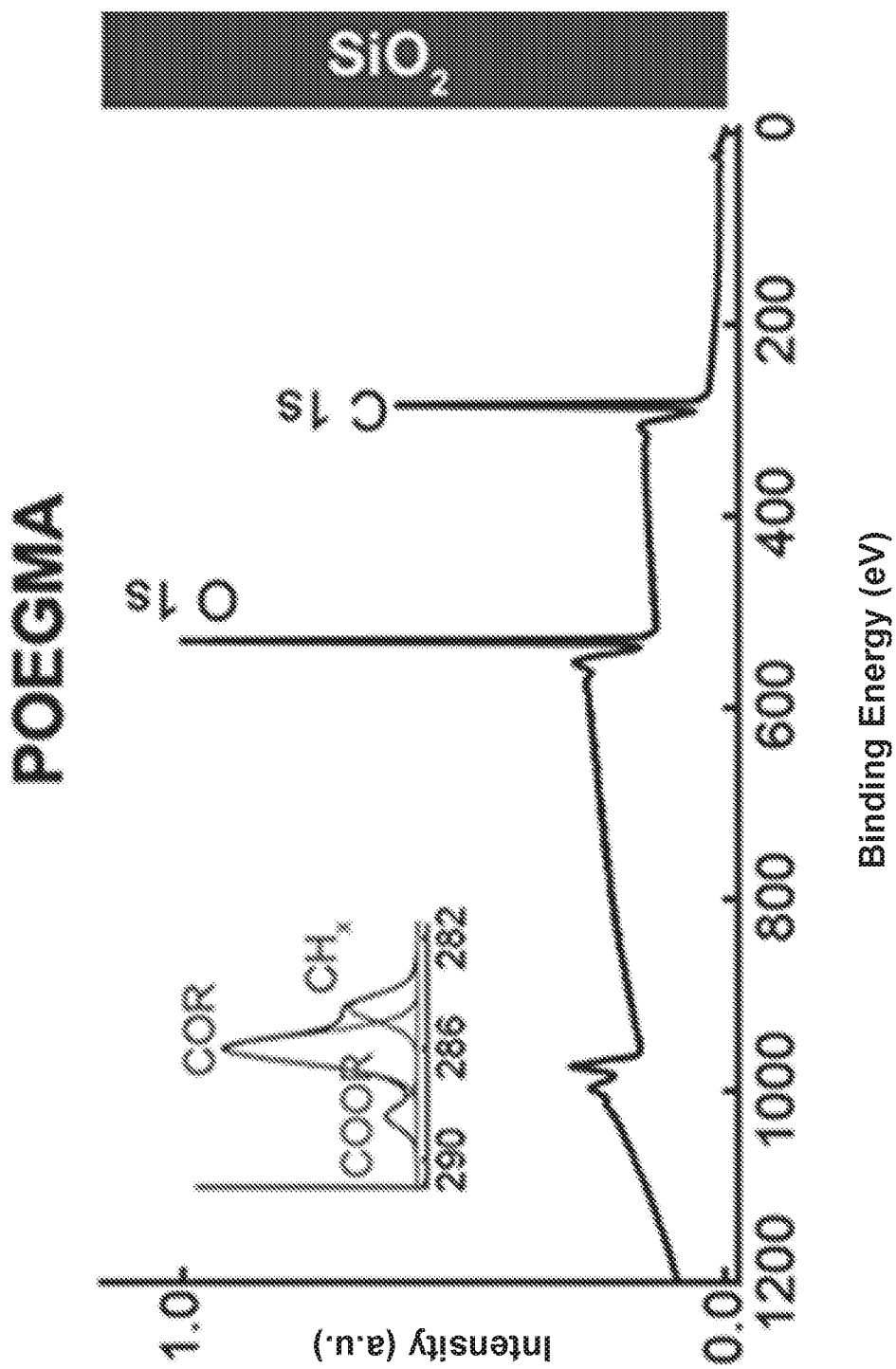
Figure 4D:
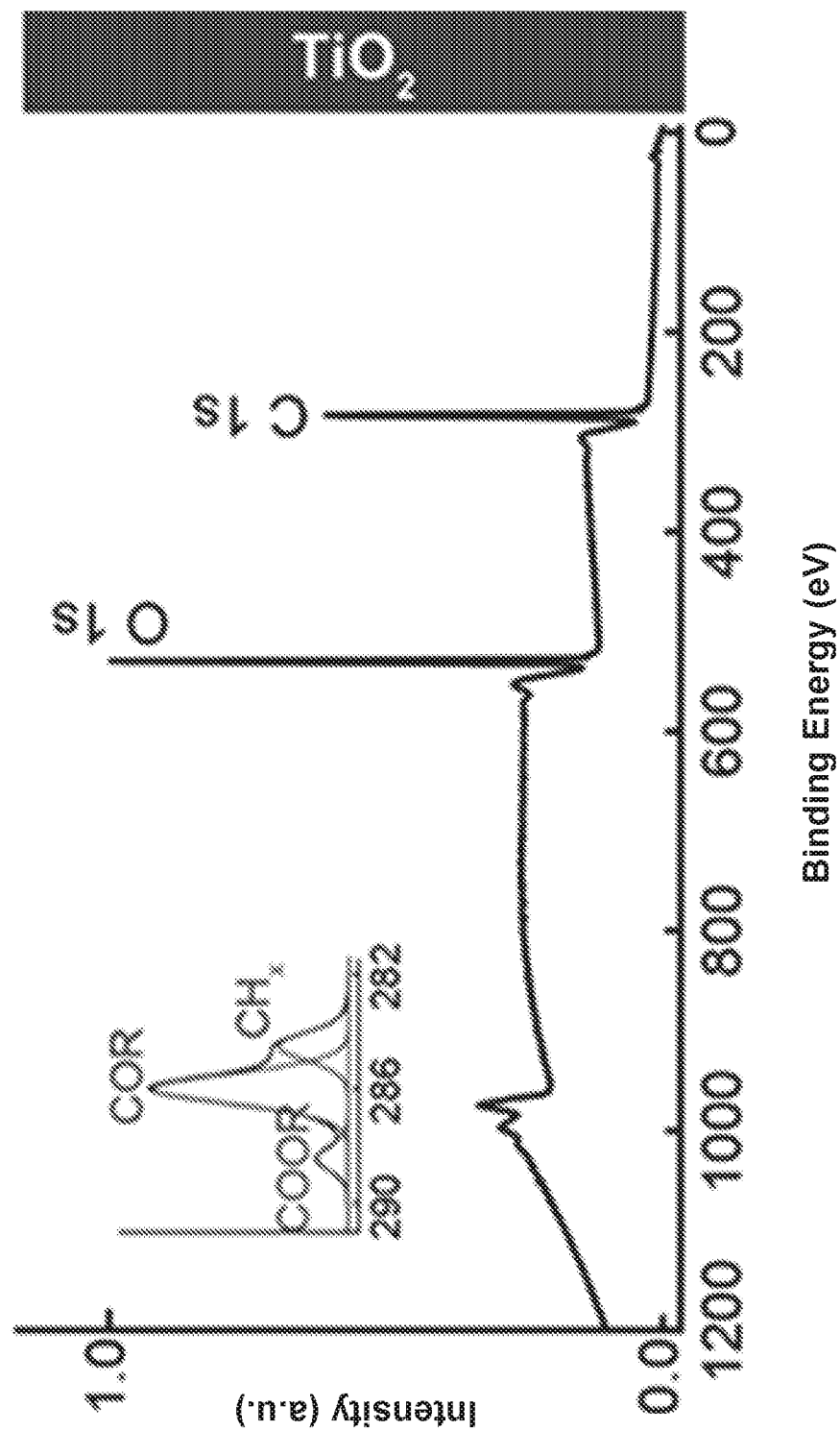
Figure 5A:
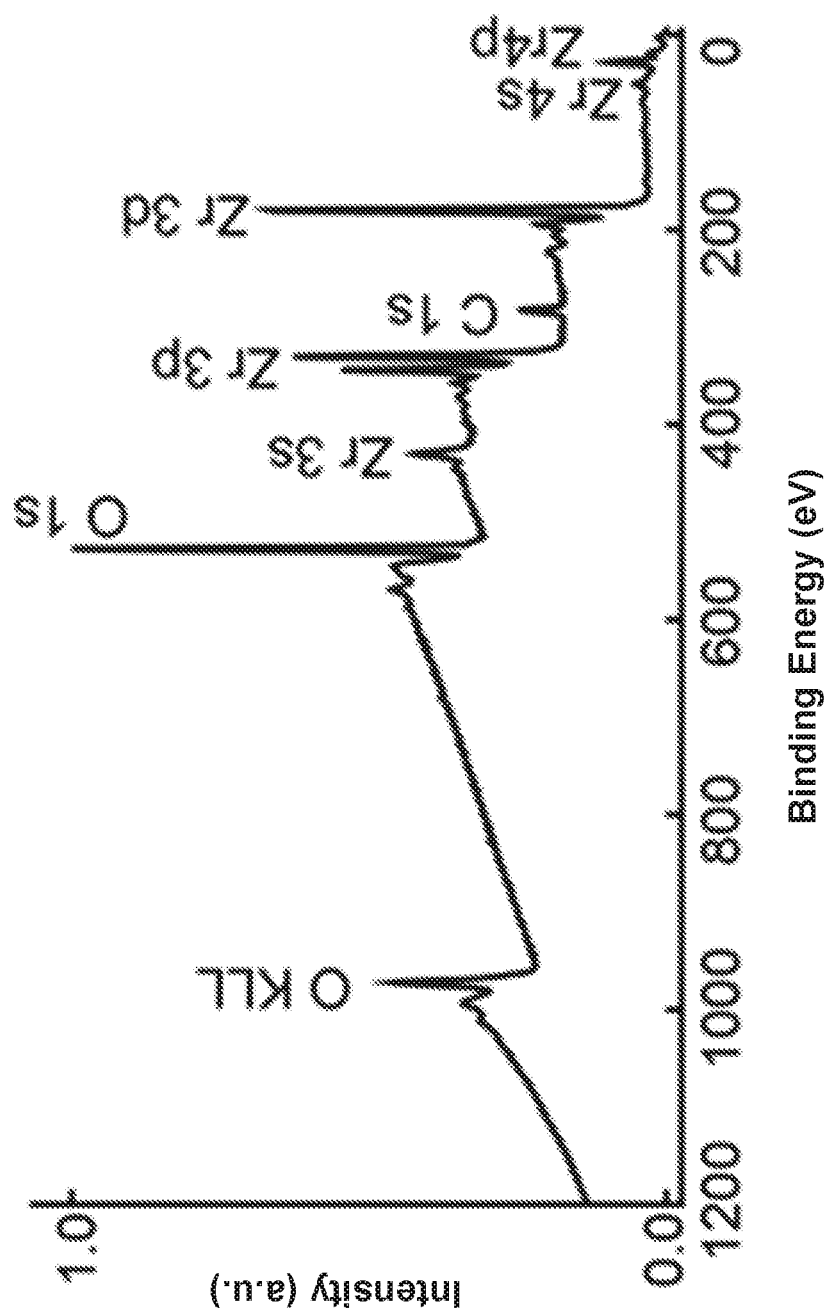
FIG. 5 A-D is a set of graphs showing X-ray photoelectron spectra prior to and after SI-ATRP on metal oxides. (A & B): survey spectra of initiator-grafted (APTES-BiB) surfaces on ZrO$_2$ and Al$_2$O$_3$, respectively. (C & D): survey spectra following SI-ATRP of POEGMA brushes. Insets: High resolution C1s spectra following SI-ATRP, showing peaks consistent with POEGMA brushes following peak fitting.
Figure 5B:
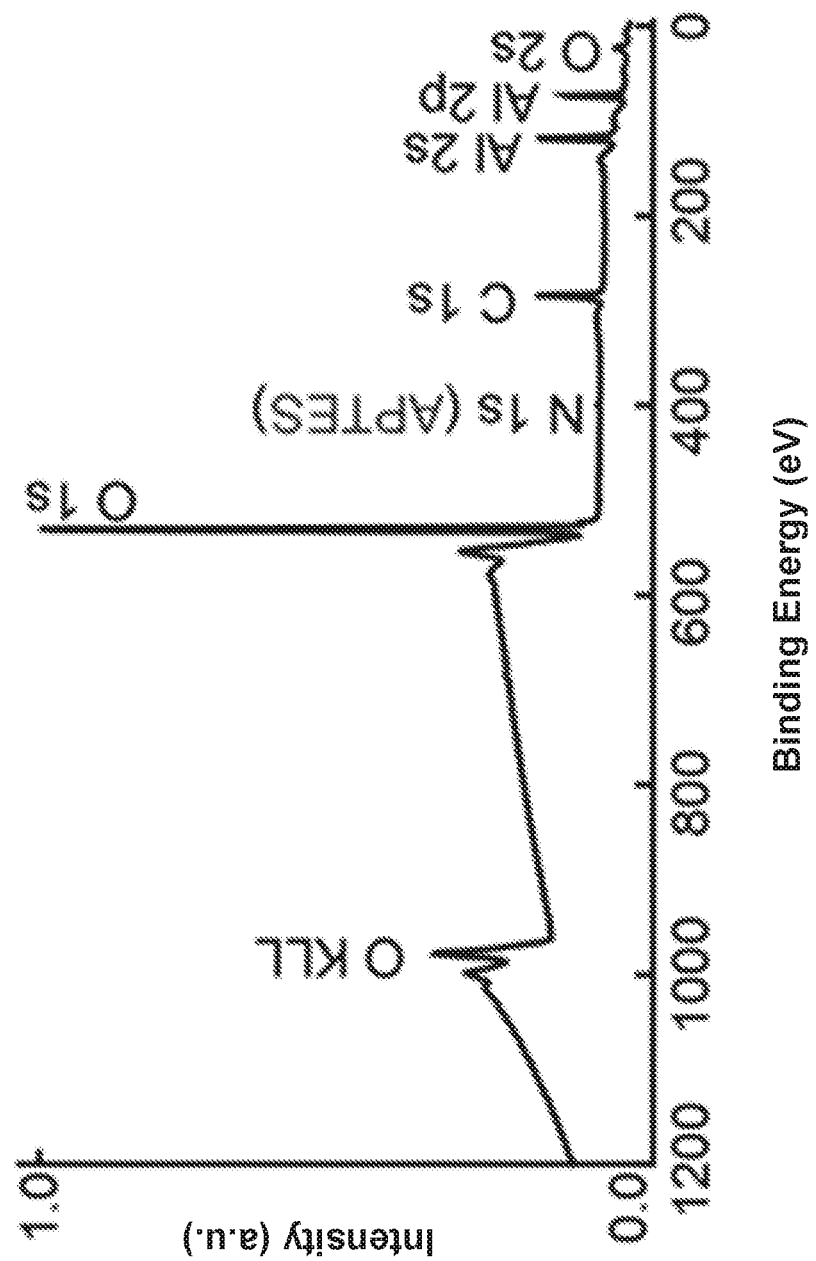
Figure 5C:
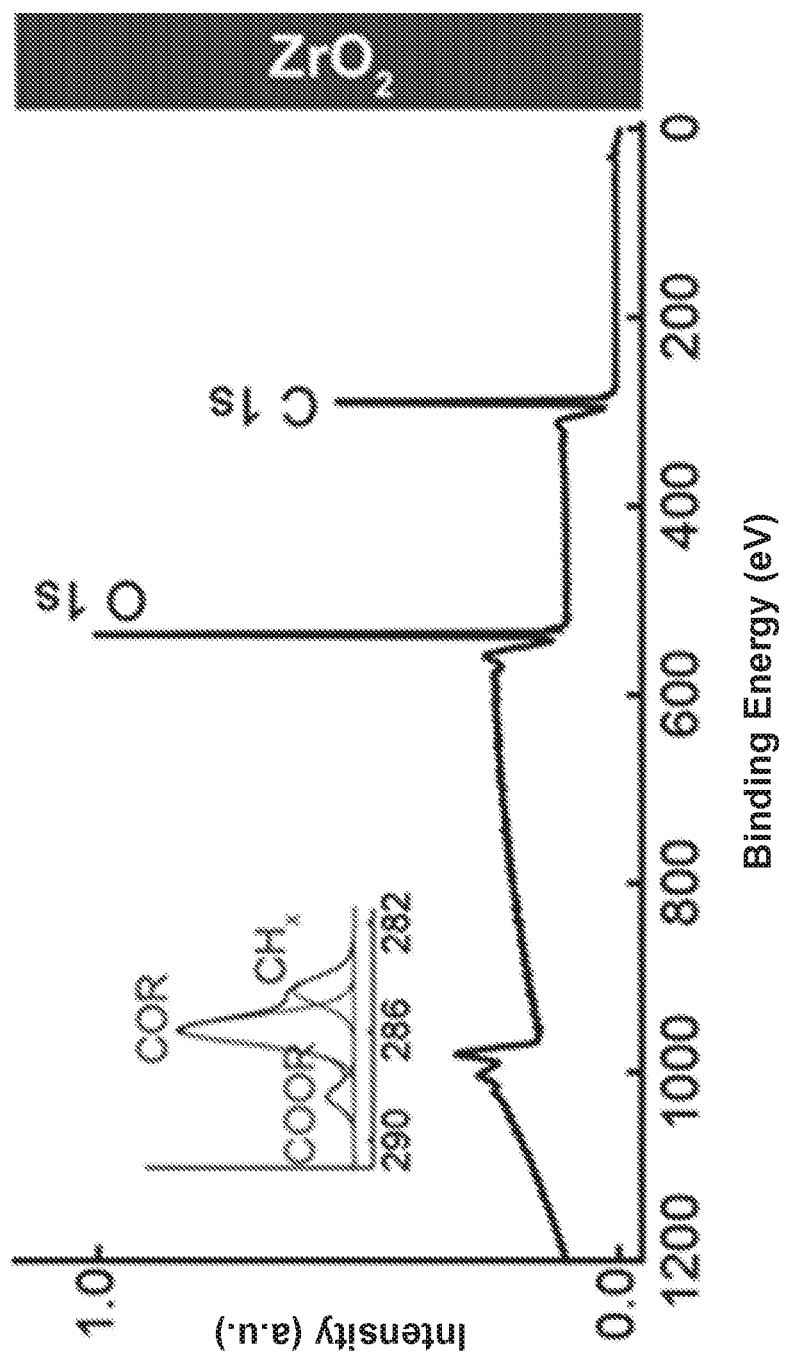
Figure 5D:
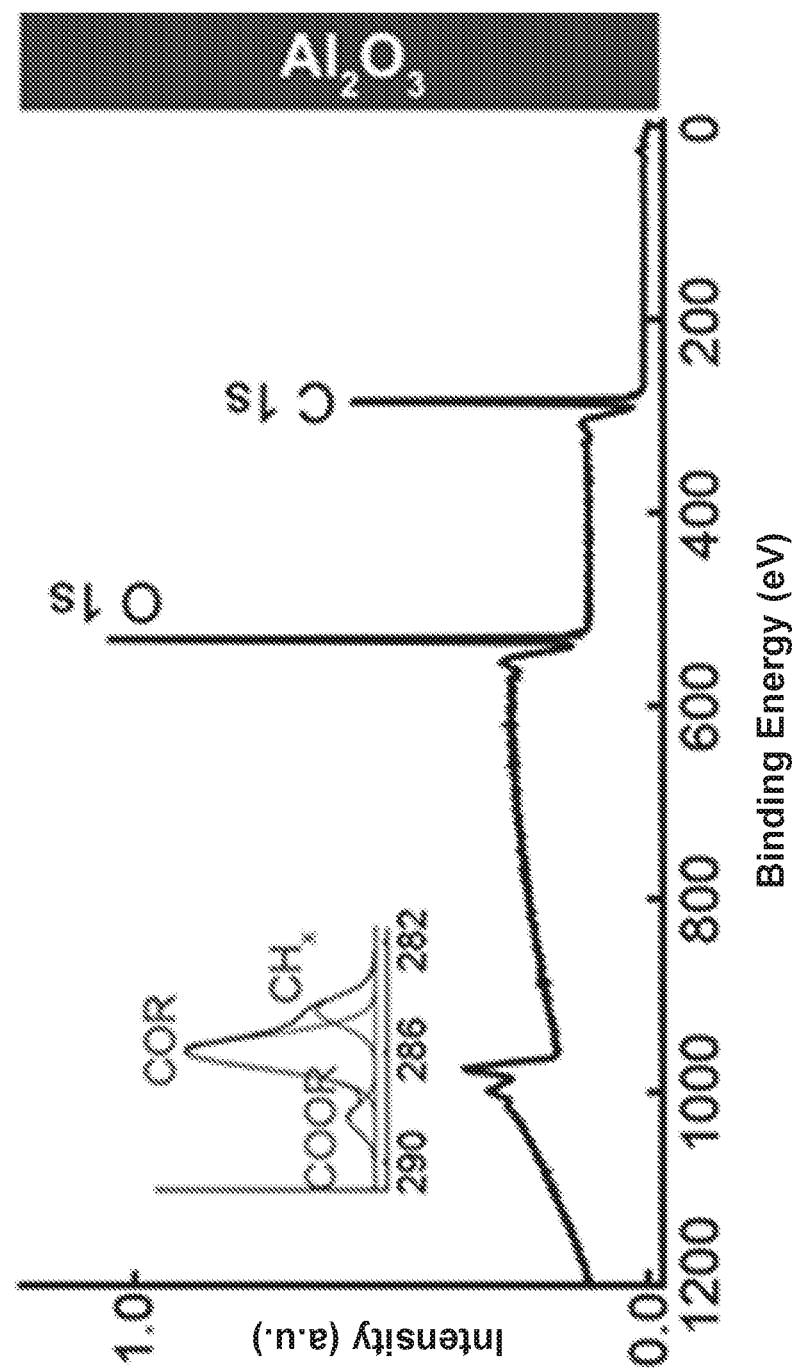

The growth behavior of ARGET SI-ATRP-based was investigated by reflective mode spectroscopic ellipsometry in air. FIG. 2 shows the growth of POEGMA on TiO$_2$, ZrO$_2$, and Al$_2$O$_3$ surfaces, and on SiO$_2$ as a comparison. The thickness of the POEGMA brush progressively increases over time in a controlled manner, reaching thicknesses of approximately 30-60 nm under these experimental conditions. The data show consistent film thicknesses between substrate replicates per time point, and the observed minor differences in final film thickness for each POEGMA brush layer is likely due to small variances in reaction conditions between batches (e.g. residual oxygen leading to premature chain termination). Importantly, the 30-60 nm brush thicknesses are well above the minimum values for which POEGMA surfaces exhibit non-fouling behavior: brushes thicker than ~9.5 nm can be exceptionally resistant to the adventitious adsorption of "sticky" proteins such as fibronectin, in addition to components of complex biological media such as undiluted serum. Thus, these methods lead to POEGMA brushes that reach adequate thicknesses for use as non-fouling biointerfacial layers on high-κ metal oxide dielectrics. As a control experiment, the growth of POEGMA on SiO$_2$ substrates coated with APTES only was compared to substrates coated with APTES plus bromide initiator (APTES-BiB). The data in FIG. 3 show that Si/SiO$_2$ chips coated with APTES alone and then placed in polymerization solution do now show any appreciable polymer brush growth after 60 minutes, while chips with bromide initiator installed (APTES+BiB) grew 20 nm brushes. These results unequivocally confirm that POEGMA only grows from a surface as a consequence of polymerization that originates from the ATRP initiator that is attached to the substrate surface.

To characterize the POEGMA films in greater detail, we used x-ray photoelectron spectroscopy (XPS) to analyze the molecular composition of the substrate, the initiator functionalized surface and the POEGMA overlayers (FIGS. 4 & 5). FIGS. 4 & 5 (A-B) show survey spectra of SiO$_2$, TiO$_2$, ZrO$_2$, and Al$_2$O$_3$ surfaces after surface functionalization with APTES-BiB, but prior to polymerization. Each of the survey spectra exhibits the characteristic peaks associated with each oxide dielectric. In addition, a small peak at ~399 eV matching an N is photoelectron peak is also observed, which corresponds to the nitrogen moieties from APTES immobilized on the surface (except in the case of ZrO$_2$, where this peak is obscured by the spectral contributions from the metal oxide). The bromide peaks associated with the ATRP initiator were unresolved in the survey spectra; these findings are consistent with previously reported XPS studies on electrochemically-assisted growth of TiO$_2$ films functionalized with APTES-BIB.

FIGS. 4 & 5 (C-D) show survey scan spectra of substrates having thick (greater than 25 nm) overlying POEGMA films after SI-ATRP. These film thicknesses are greater than the sampling depth of XPS (which is typically up to ~10 nm for Al Kα radiation depending upon the specific core level photoelectrons), and thus the vast majority of detected photoelectrons are expected to originate from the POEGMA layer. For each POEGMA-coated oxide substrate, the survey scan spectra clearly demonstrate significant changes in elemental composition compared to substrates before polymerization. The spectral peaks associated with the metal oxide dielectrics in FIGS. 4 & 5 (A-B) are virtually absent, and the spectra of POEGMA-coated substrates appear practically identical, with each showing a notably sharp increase in the C1s (284.5 eV) peak. High-resolution XPS of the C1s photoemission envelope for each polymer brush-modified substrate (insets, FIGS. 4 & 5 (C-D)) were fit to the three unique carbon moieties of POEGMA: $CH_x$ (284.5 eV), COR (286.7 eV), COOR (289.1 eV). The molecular composition of each overlayer are summarized in Table 2, all of which are reasonably close to the ~1:3:10 (COOR:$CH_x$:COR) stoichiometry of POEGMA assuming 4-5 ethylene glycol units in the side-chain of each POEGMA repeat unit.

TABLE 2

Atomic concentrations (%) of carbon and oxygen moieties before (BIB-APTES) and after polymerization.

| | Pre-ATRP (%) | | | Post-ATRP (%) | | | | | |
|---|---|---|---|---|---|---|---|---|---|
| | Survey | | | Survey | | | High-Res. C1s | | |
| | C | O | M | C | O | M | CHx | COR | COOR |
| $SiO_2$ | 13.5 | 61.4 | 25.1 | 71.1 | 28.6 | ND | 22.8 | 68.3 | 8.9 |
| $TiO_2$ | 22.5 | 57.4 | 20.1 | 71.3 | 28.7 | ND | 24.5 | 66.9 | 8.6 |
| $ZrO_2$ | 23.4 | 60.4 | 16.2 | 69.5 | 30.5 | ND | 23.6 | 67.8 | 8.6 |
| $Al_2O_3$ | 14.6 | 52.5 | 32.9 | 69.4 | 30.6 | ND | 20.4 | 71.0 | 8.6 |

"M" stands for metal (Ti, Zr, Al,), or metalloid in the case of Si.

Figure 6:
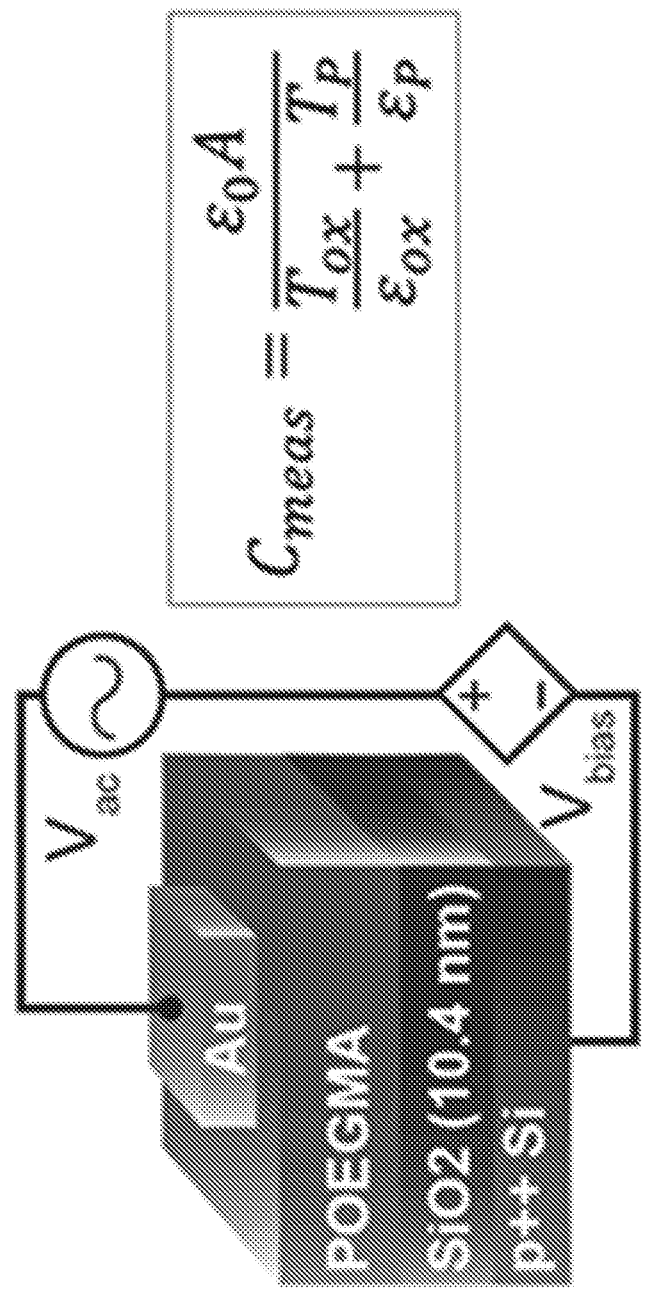
FIG. 6 is a schematic of the POEGMA samples used to obtain the capacitance-voltage curves with detailed expression for the total measured capacitance ($C_{meas}$) used for determining permittivity.

Next, the response of the POEGMA films under applied electric fields was studied to determine the material's electrical characteristics. Parallel-plate capacitors were fabricated as shown in FIG. 6, by first growing POEGMA on p++ doped, low-resistivity Si wafers with a 10.4 nm thick thermally grown $SiO_2$ overlayer. Top contact electrodes (4 mm² in size) were then formed by evaporating 5 nm Ti and 30 nm Au through a shadow mask in an electron-beam evaporator. Capacitance-voltage (C-V) measurements from these parallel-plate structures allow us to extract the relative permittivity of POEGMA ($\varepsilon_P$). When the device is biased in the strong accumulation regime, the measured capacitance is effectively the result of two capacitors in series—one with $SiO_2$ one with POEGMA. The expression for $C_{meas}$ described using a parallel-plate model by Equation 1, in which A is the area, $T_{ox}$ and $T_P$ is the thickness of the oxide and POEGMA (respectively), and $\varepsilon_{ox}$ and $\varepsilon_P$ are the relative permittivity of the oxide and POEGMA (respectively):

$$C_{meas} = \frac{\varepsilon_0 A}{\frac{T_{ox}}{\varepsilon_{ox}} + \frac{T_P}{\varepsilon_P}} \quad (1)$$

Figure 7:
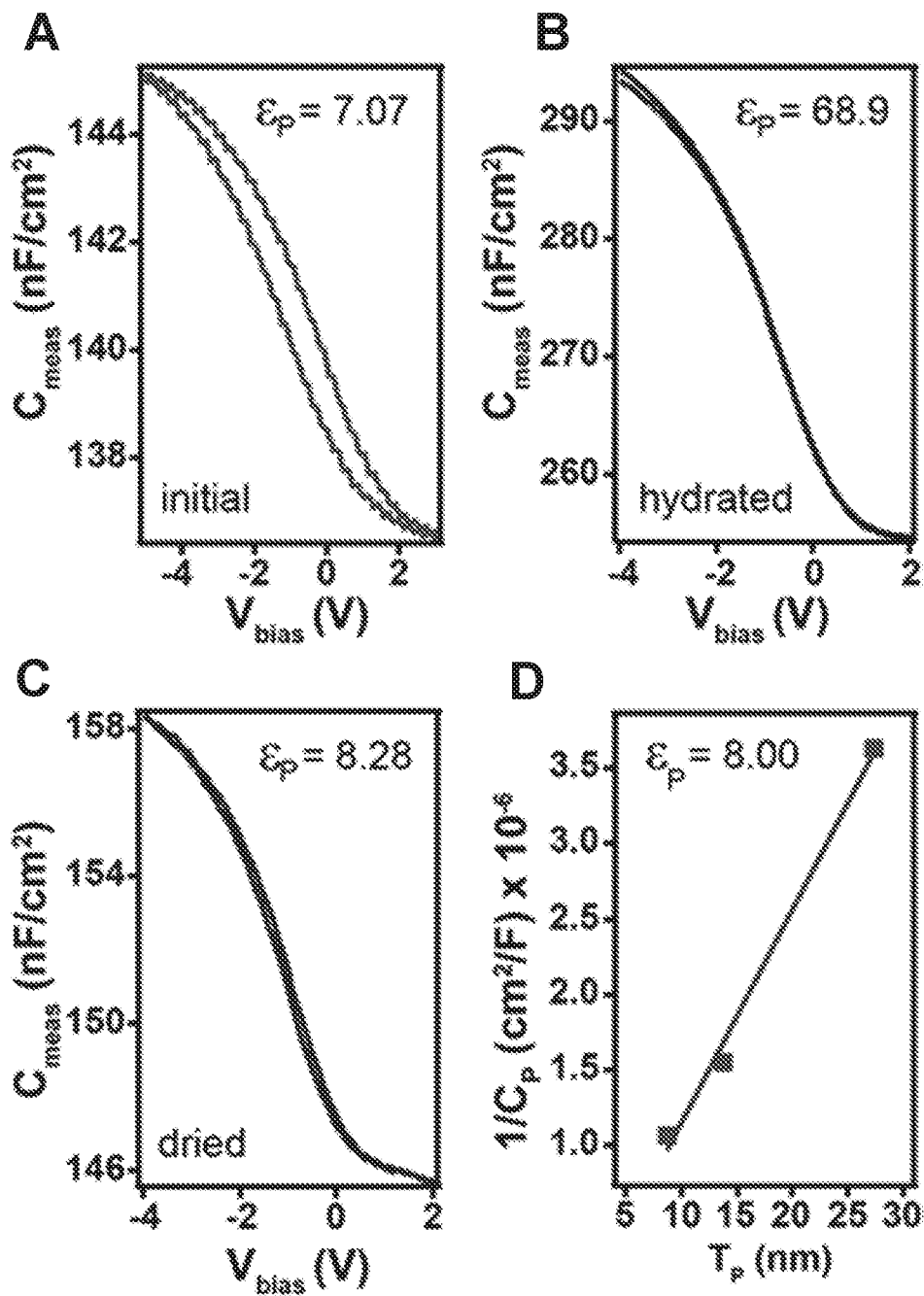
FIG. 7 is a set of graphs showing capacitance-voltage measurements on POEGMA. (A-C): sequence of capacitance-voltage curves from a POEGMA film of 24.3 nm thickness beginning with the initial characteristic (A), followed by the response post-hydration of the POEGMA (B), and finally after a drying step to dehydrate (C). (D): linear fit to plot of the inverse POEGMA capacitance versus thickness used to confirm the extracted permittivity Ep.

A representative C-V measurement from one of the POEGMA capacitors is given in FIG. 7A in which $C_{meas}$ is plotted against bias voltage from a device having a POEGMA film thickness of 24.3 nm. Substituting the strong accumulation capacitance for $C_{meas}$ into Eq. 1 led to an experimentally determined value for $\varepsilon_P$ as ~7.07. For biosensing-related applications, devices are exposed to wet environments and thus further C-V characterization was performed under conditions that more closely mimic the wet environment in which POEGMA films will need to operate. To this end, we submerged the same device from FIG. 7A in a 1× PBS buffer for 5 min to hydrate the POEGMA, followed by immediate electrical characterization under ambient conditions. The response of the POEGMA after hydration with 1× PBS is shown in FIG. 7B. The hydrated POEGMA shows a significantly increased relative permittivity ($\varepsilon_P$=68.9) compared to dry POEGMA, approaching a value closer to that of water. This behavior is consistent with the highly hydrophilic nature of POEGMA, leading to water molecules penetrating into and residing within the polymer brush by hydrogen bonding interactions. Subsequently, the same sample was dried overnight in a vacuum desiccator to return the POEGMA to a dry state for a final C-V measurement (FIG. 7C). The relative permittivity of the dried POEGMA showed a value $\varepsilon_P$ of 8.28 that was consistent with the initial measurement (FIG. 7A). The slight difference in experimental $\varepsilon_P$ between the initial and dried samples (FIGS. 7 A and C) may be attributed to the ability for oligoethyelene glycol brushes to retain residual amounts of water after drying. This overall behavior is consistent with several studies showing that oligoethylene glycol brushes can reversibly recover their original structure and retain non-fouling characteristics after dehydration cycles, which is particularly relevant to sensing applications requiring repeated use with the same device. To complete the extraction of the permittivity for POEGMA, films of different thicknesses were grown and C-V measurements were obtained for each sample. As depicted in Equation 2, the capacitance of the POEGMA film ($C_P$) is inversely related to its thickness ($T_P$):

$$C_P = \frac{\varepsilon_P \varepsilon_0 A}{T_P} \quad (2)$$

FIG. 7D plots values of $1/C_P$ versus $T_P$, which yields a linear fit for a more accurate relative permittivity for as-grown POEGMA, calculated to be $\varepsilon_P$=8.00.

Figure 8:
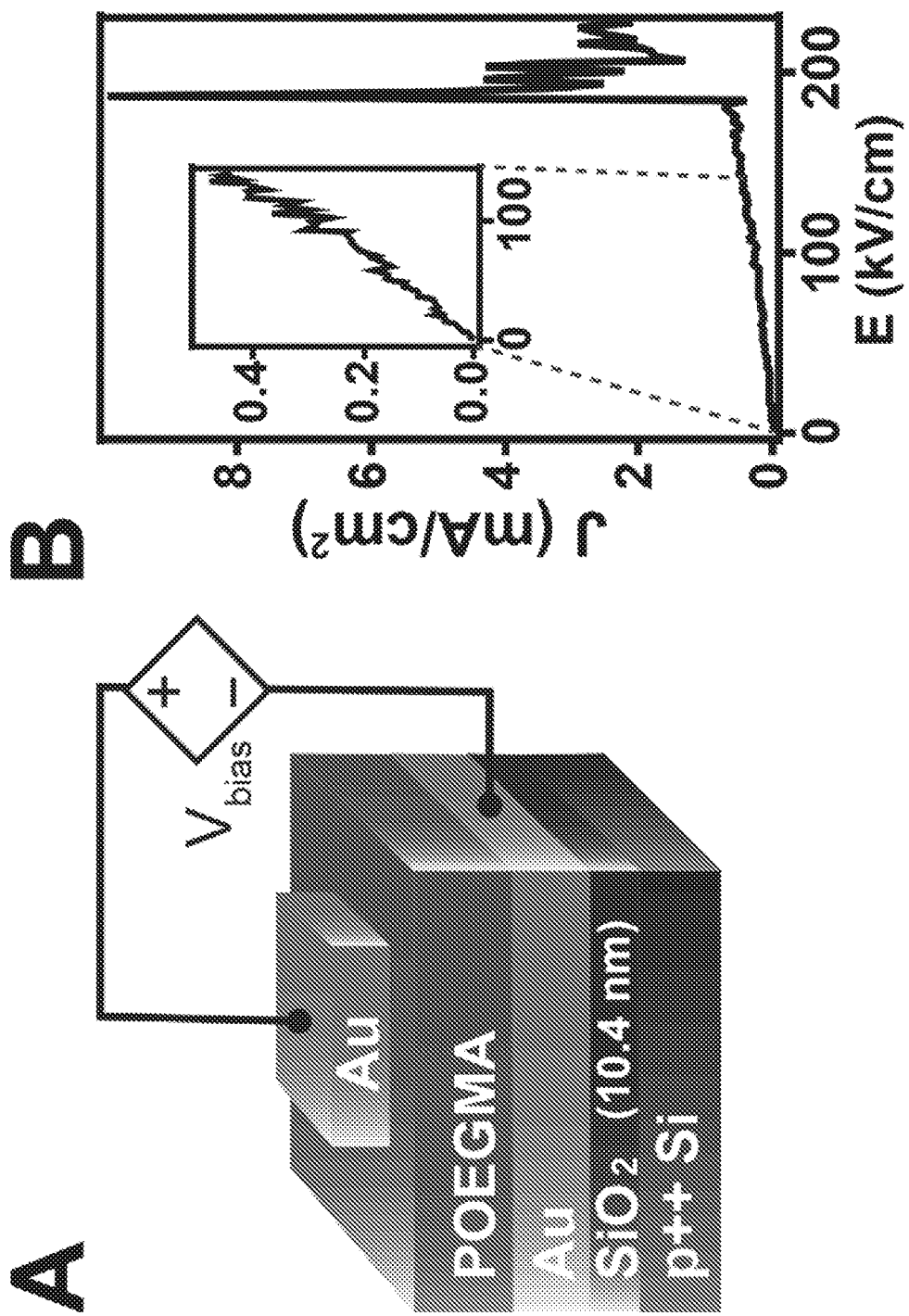
FIG. 8 is (A): a schematic of a POEGMA sample used to investigate the breakdown of POEGMA films. (B): is a graph showing the breakdown curve for a POEGMA film of 44.2 nm thick.

To assess the robustness of POEGMA as a dielectric material, the breakdown behavior was characterized, as shown in FIG. 8. For these measurements, the device geometry used is shown in FIG. 8a, by growing POEGMA (44.2 nm) on a patterned gold electrode and subsequently fabricating a gold top contact, then measuring current density under an increasing electric field. The results are shown in FIG. 8b, where breakdown is initiated at an applied field of 183.2 kV/cm, confirming that POEGMA functions as a stable dielectric material with a relatively robust breakdown field that is approximately within an order of magnitude of high-quality thermal $SiO_2$.

Figure 9:
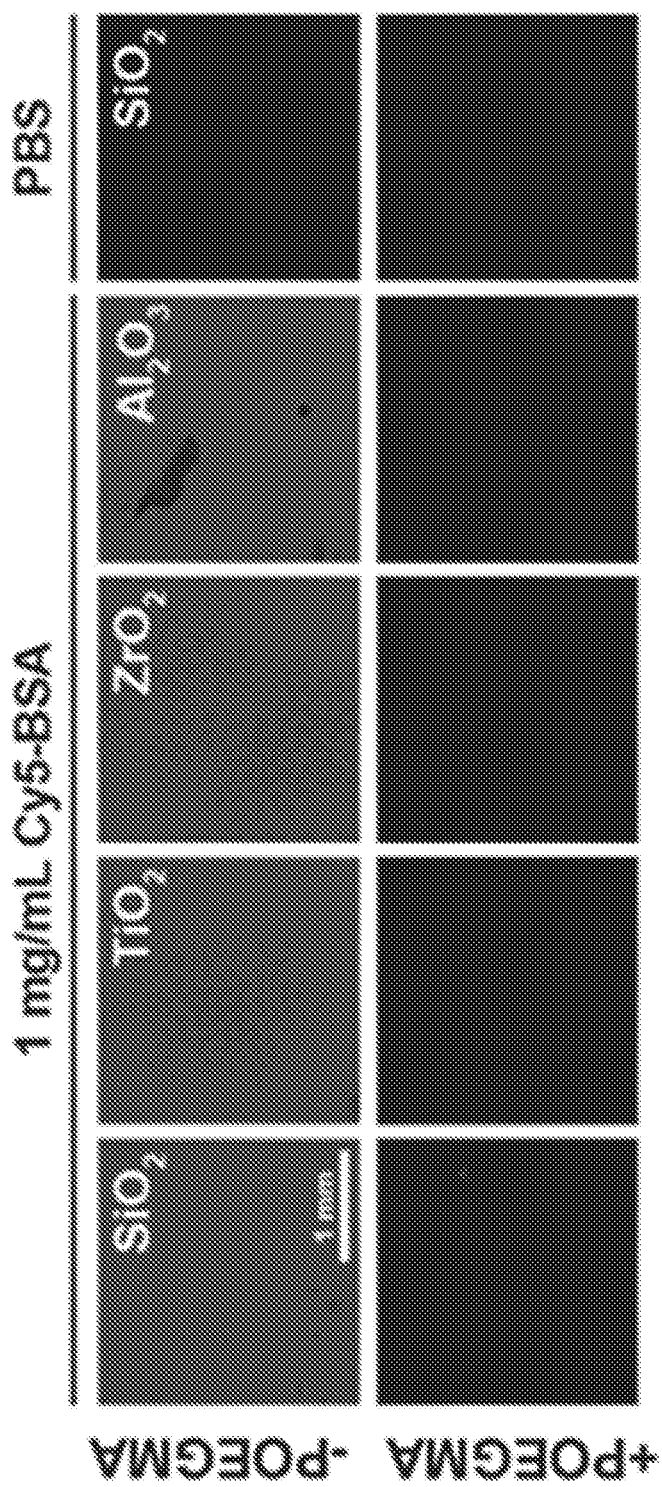
FIG. 9 is a set of fluorescence images of adsorption of Cy5-BSA onto dielectric metal oxide surfaces with and without POEGMA coatings. Images of SiO$_2$ surfaces (with and without POEGMA) treated with PBS vehicle also shown as negative control.
Figure 10:
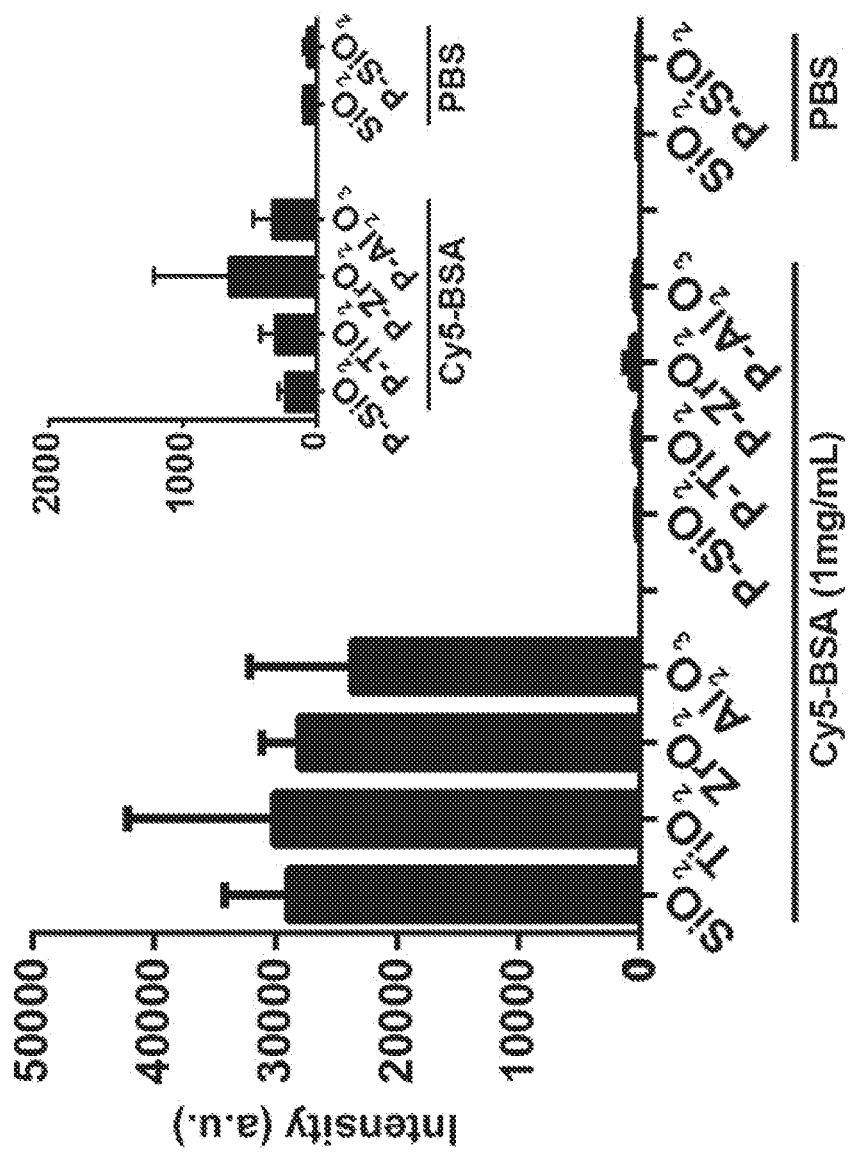
FIG. 10 is the quantitation of fluorescence from residual Cy5-BSA bound to surfaces at the conditions described in FIG. 9; data are average ±s.d. of 3 separate chips. Inset: magnified view of low fluorescence intensity data.

Lastly, to demonstrate the effects of POEGMA on the surface of dielectric metal oxides, POEGMA-coated dielectric oxides were incubated with fluorescently-labeled BSA. The superior non-fouling property of POEGMA can be seen in FIGS. 9 and 10.

In summary, POEGMA coatings can be reliably grown on the surface of high-κ metal oxide dielectric materials using a facile "grafting-from" SI-ATRP strategy. SI-ATRP enables POEGMA films to grow in a controlled manner and reach thicknesses at which POEGMA is known to exhibit highly non-fouling behavior, which can provide a high SNR in biological detection devices by eliminating adventitious adsorption of cells and proteins from the sensor interface. XPS confirmed the fidelity of POEGMA films with respect to their predicted stoichiometry, and showed consistent chemical composition of the coatings across each high-κ growth surface. Finally, electrical characterization studies enabled determination of the relative permittivity of POEGMA in both dry and hydrated states, and showed that the POEGMA film behaves as a stable dielectric material with a breakdown field strength that is sufficiently strong for integration in biosensing devices. While the present example focuses on representative high-κ metal oxide dielectrics ($TiO_2$, $ZrO_2$, $Al_2O_3$), the results described herein are applicable by extension to the metal oxides currently favored by the electronics industry such as $HfO_2$ and Hf-silicate ($HfSi_xOy$), and also to $Y_2O_3$, $La_2O_3$, $Sc_2O_3$ $Pr_2O_3$, $Gd_2O_3$ and $Lu_2O_3$ that may become relevant as CMOS technology continues to evolve.

Example 2

Printed, Nonfouling Biosensors

Experimental

Aerosol Jet Printed CNT Transistors: The first step in developing a fully printed CNT-TFT for biological sensing was to design the optimal geometry and print processing steps to obtain a stable, high performing transistor. For the biosensor device, top gated transistors were fabricated with silver nanoparticle contacts. These were chosen because: it is much more cost effective than gold nanoparticle ink; secondly, metallic CNT contacts were avoided due to their strong sensitivity to environmental factors; and lastly the top contacts were chosen in order to minimize the interaction of biological molecules/milieu at the CNT-Ag ink interface.

As for device geometry, one necessity was the ability to isolate the channel from the contact probes in order to not form conducting pathways between the source and drain. Therefore, an active area was designed in the middle of the wafer and would be protected by a rubber gasket. Contact pads were printed on the outside of the rubber gasket to allow for device testing during assays. For preliminary test results, substrate gated devices were focused on to remove any variables extending from a printed dielectric.

Figure 11:
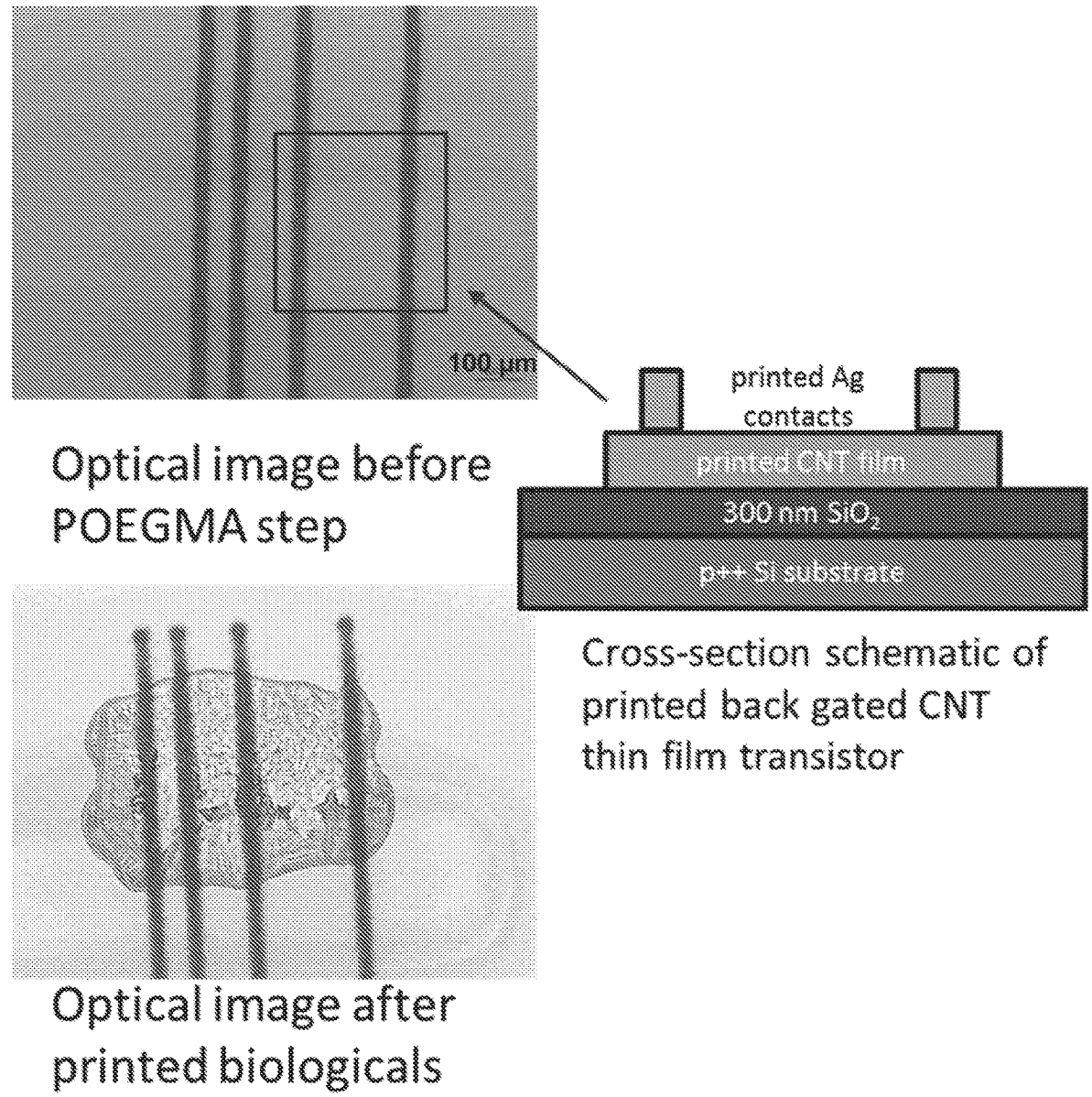
FIG. 11 is a schematic of printed substrate gate CNT-thin filmed transistor (CNT-TFT) profile without a second dielectric layer in between the carbon nanotube channel and the non-fouling polymer layer. Optical images (with a 100 μm scale bar) show sensors before POEGMA step and after printed biologicals.
Figure 16:
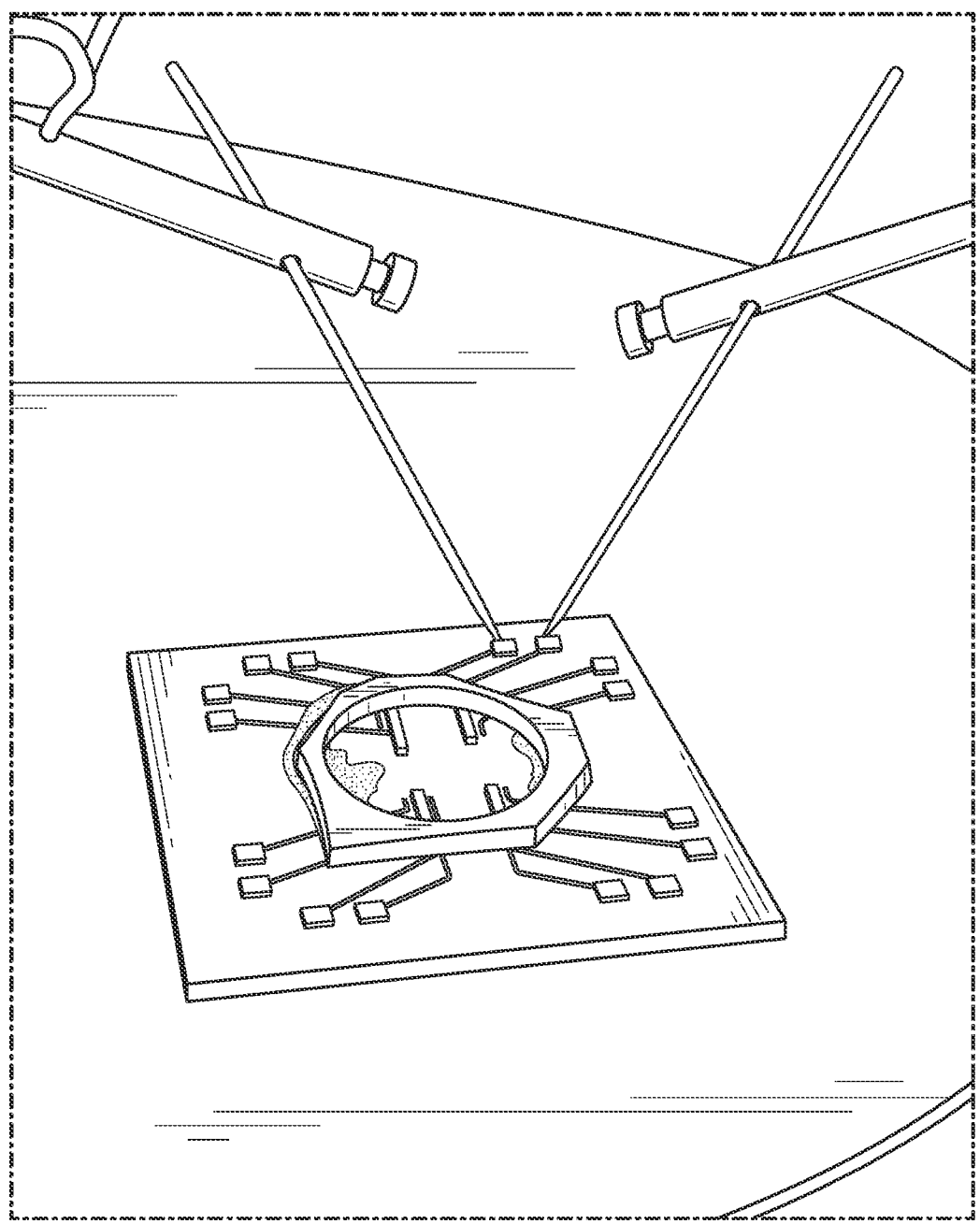
FIG. 16 is shows a fabricated device.
Figure 17:
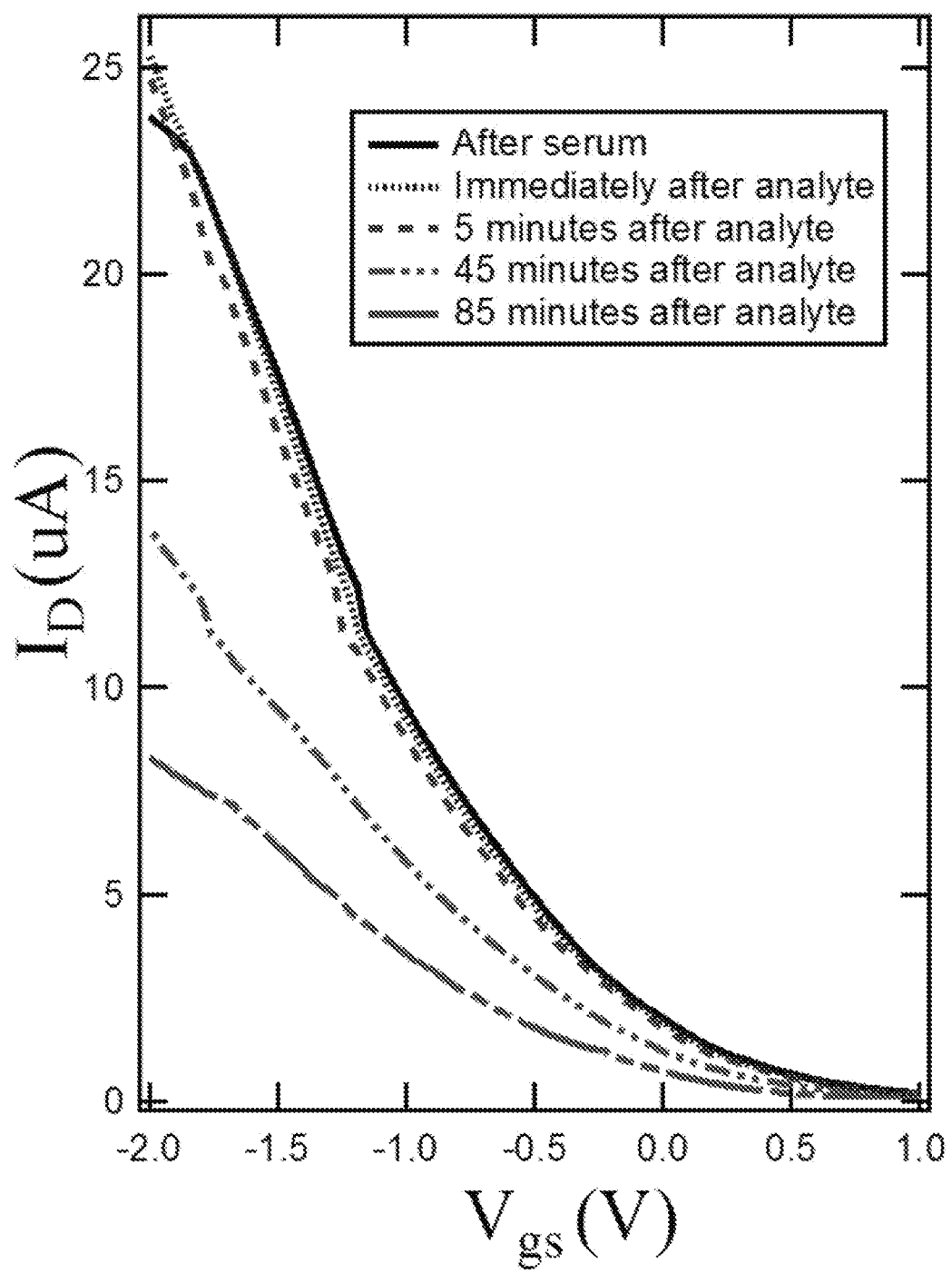
FIG. 17 is a plot of forward gate voltage swings (only) for a sensor (with a second dielectric layer) exposed to a sample including leptin.
Figure 18:
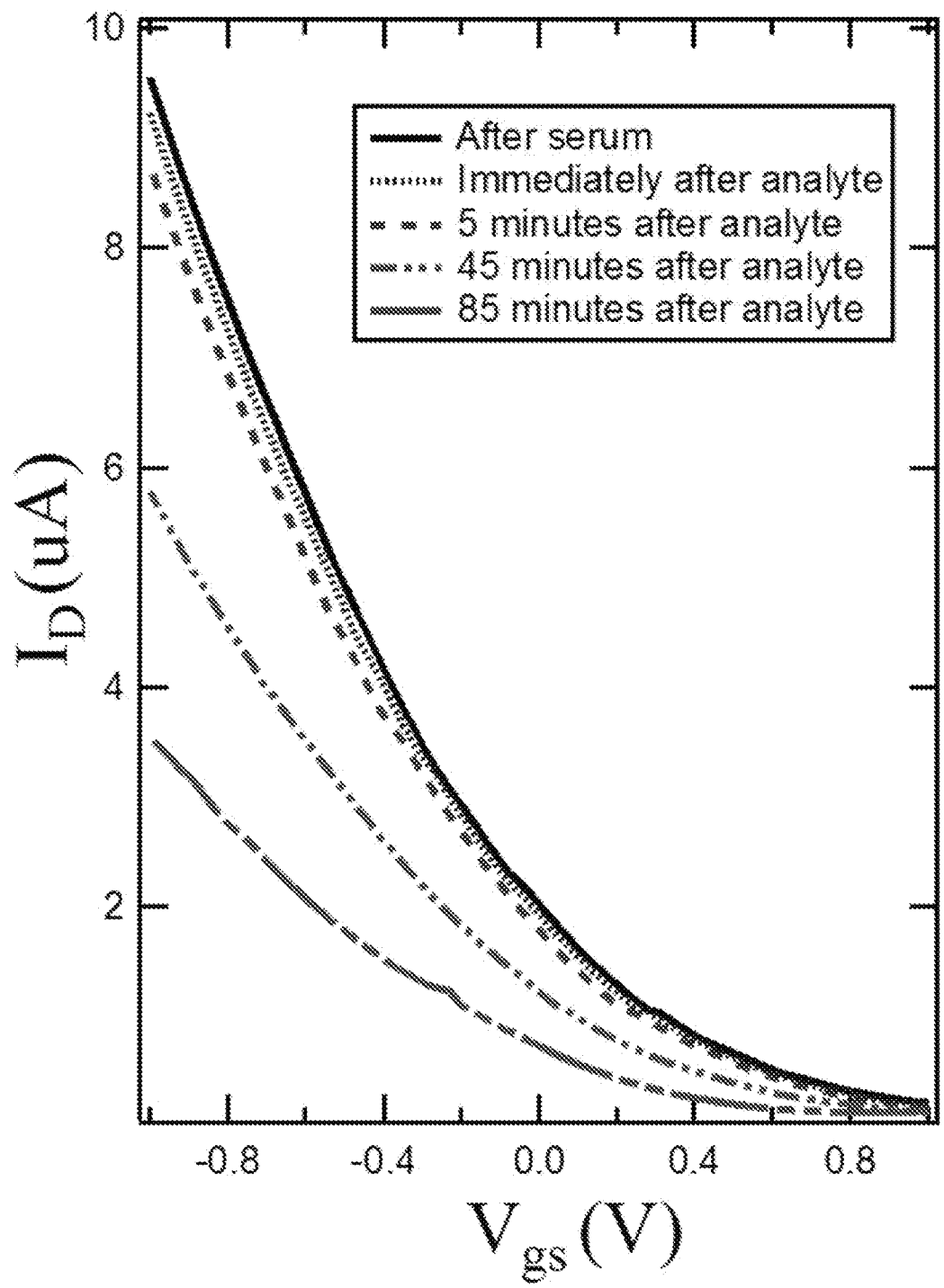
FIG. 18 is a plot of forward gate voltage swings to −1V for a sensor (with a second dielectric layer) exposed to a sample including leptin.
Figure 19:
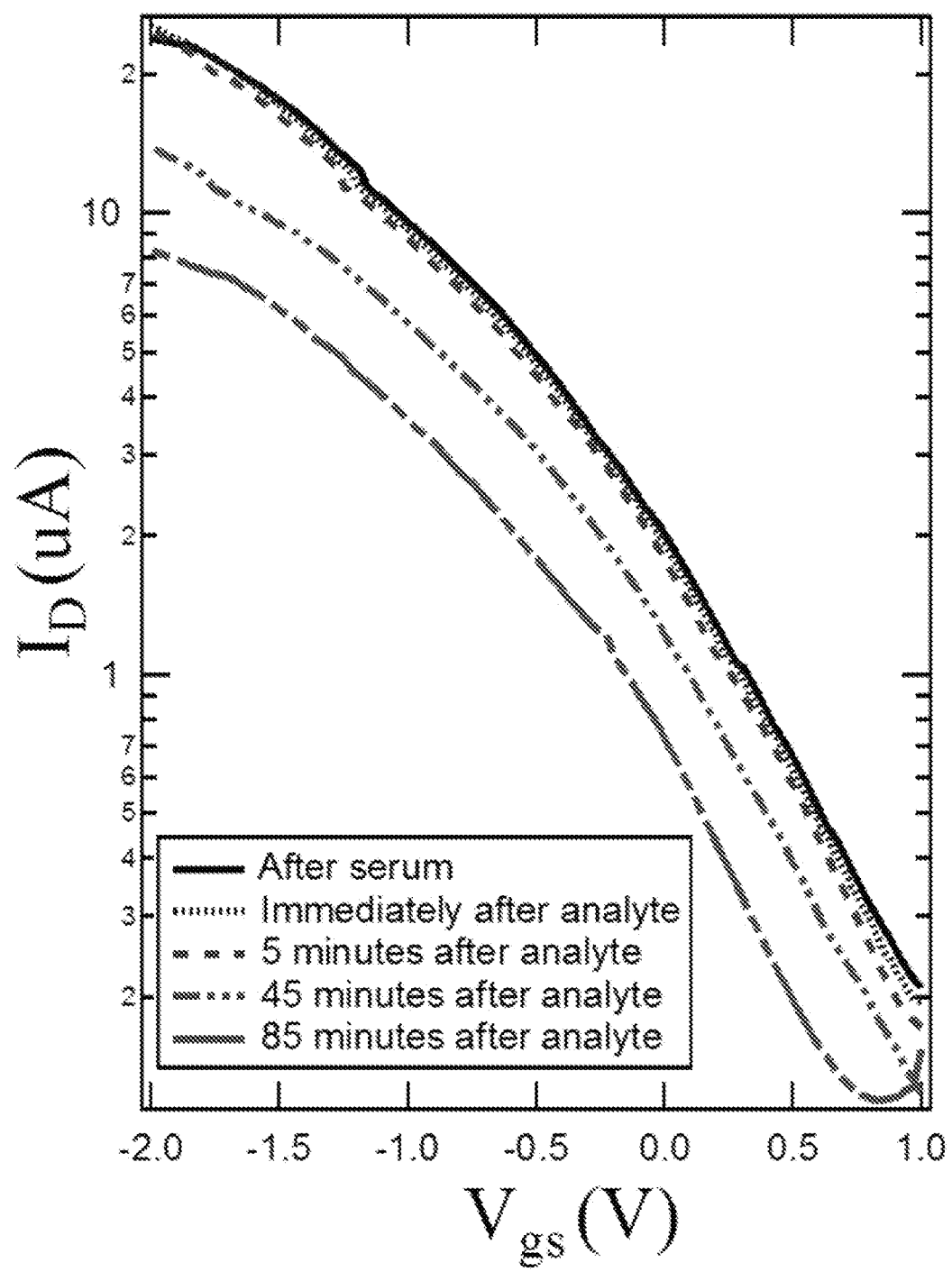
FIG. 19 is a plot of subthreshold curve forward gate voltage sweep for a sensor (with a second dielectric layer) exposed to a sample including leptin.
Figure 20:
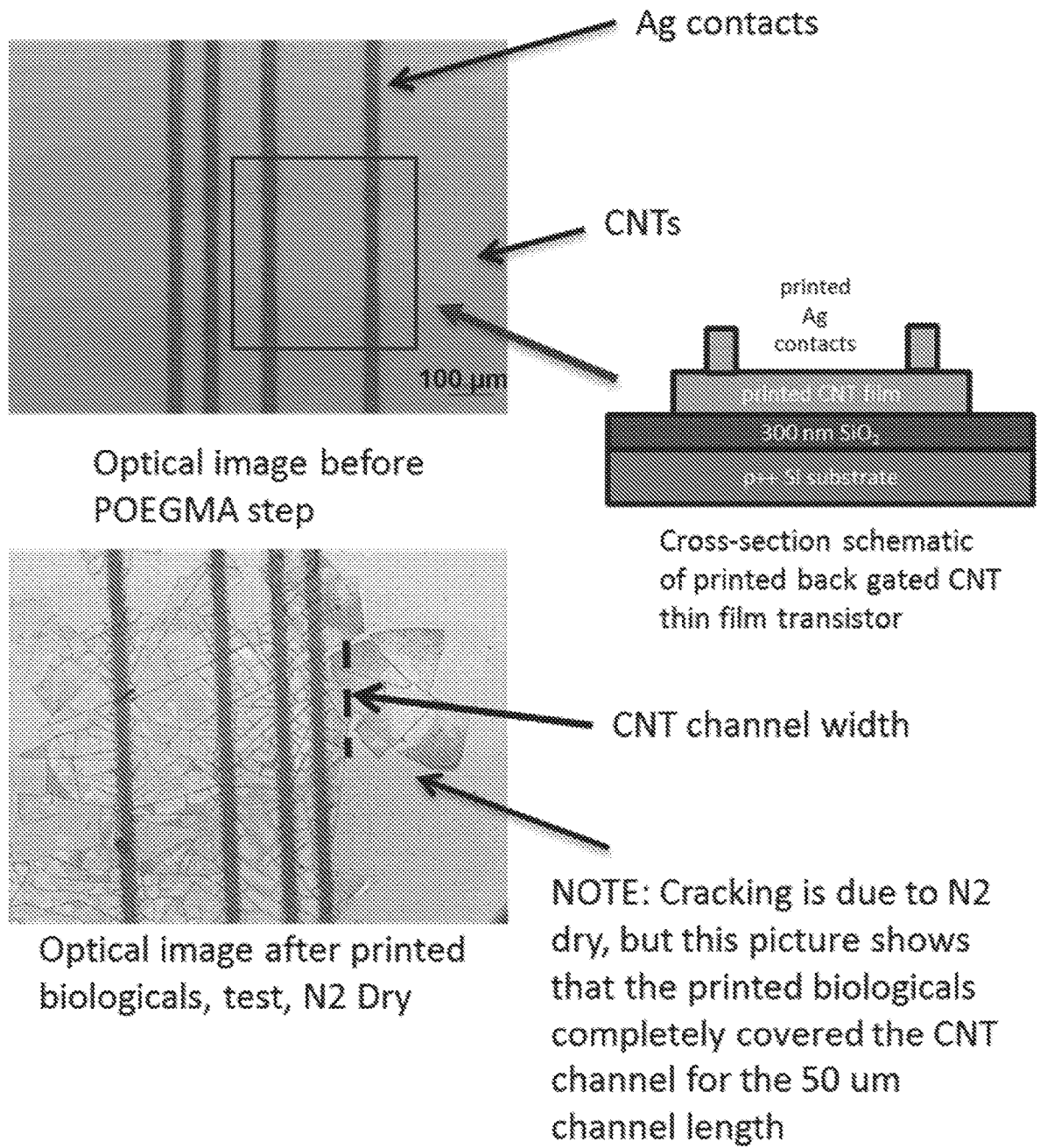
FIG. 20 is a schematic of printed substrate gate CNT-thin filmed transistor (CNT-TFT) profile without a second dielectric layer in between the carbon nanotube channel and the non-fouling polymer layer. Optical images (with a 100 μm scale bar) show sensors before POEGMA step and after printed biologicals.
Figure 23:
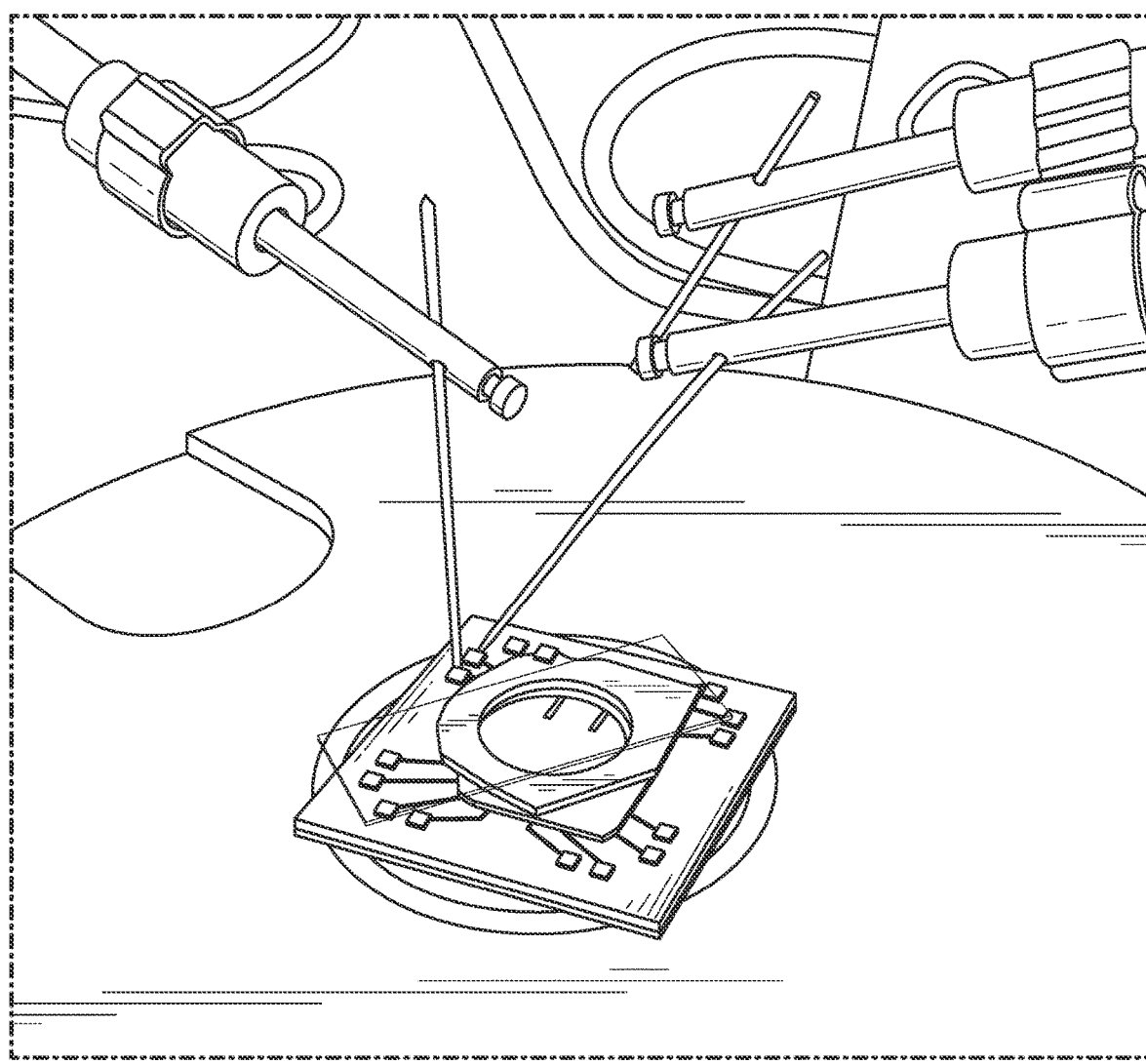
FIG. 23 shows a fabricated sensor.
Figure 30:
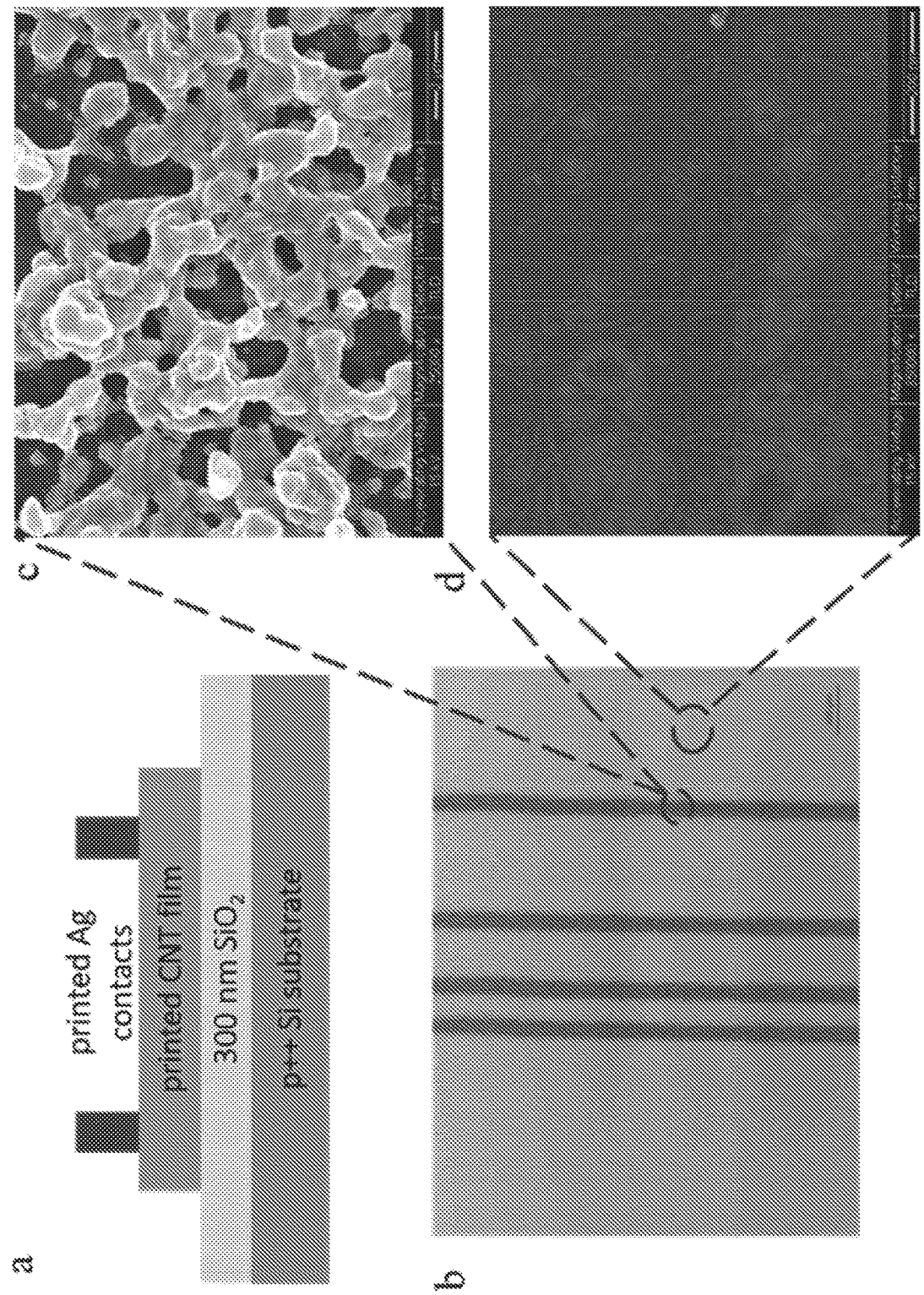
FIG. 30 is (a) a schematic of printed substrate gate CNT-TFT profile without a second dielectric layer in between the carbon nanotube channel and the non-fouling polymer layer; (b) optical image with a 100 μm scale bar; (c) SEM image at 25,000× magnification of silver nanoparticle source/drain; (d) SEM image at 350,000× magnification of CNT channel.

The substrates, either 1-inch by 1-inch or 1-inch by 3-inch diced Si wafers with a 300 nm thermally grown $SiO_2$ top layer, were first prepared by ultra-sonication in acetone and isopropyl alcohol (IPA) followed by a deionized (DI) water rinse and ultimately by an $O_2$ plasma ash to remove any molecular pollutants and functionalize the surface. For aerosol jet printing, there are three parameters of interest in the printing process. First is the sheath gas flow rate that focuses the ink, next is the carrier or atomizer gas flow rate that carries the ink, and finally there is the ultrasonic current that excites the liquid into an aerosol. First, semiconducting carbon nanotube ink (IsoSol-S100), which has a semiconducting purity of 99.9% semiconducting CNTs and was dispersed in toluene using a surfactant, was printed onto the silicon chip. The ink was printed using a sheath flow of 40 sccm, an atomizer flow of 23 sccm and an atomizer current of 470 mA. The channel width was held at 200 µm with a length of 1 mm to support 2 or 3 different channel lengths which will be defined by the contacts. After printing, the sample was placed in an oven at 150° C. in air for 10 minutes to facilitate solvent evaporation and then rinsed with toluene and DI water to remove any leftover surfactant on the nanotubes. Next, Ag nanoparticle ink (Ag-40x, UT Dots, Inc.) with 40 wt % Ag nanoparticles (diameter 20 nm) dispersed in a solvent mixture of xylene and terpineol at a volume ratio of 9 to 1 respectively was printed. The Ag ink was printed using a sheath flow of 25 sccm, an atomizer flow of 20 sccm and an atomizer current of 415 mA. The silver lines had a width of approximately 20 µm and were printed in a pattern to create three different channel length transistors (50 µm, 100, µm and 200 µm). After printing, the silver lines were placed in an oven at 200° C. in air to sinter the nanoparticles together in order to form conducting lines. These silver lines were also printed out towards the corner of the chip to allow room for the gasket in the center and to isolate the contact pads from the tested blood or serum (see FIGS. 16 and 23). A profile schematic, optical image and SEM image of the channel are shown in FIGS. 11, 20 and 30.

Figure 31:
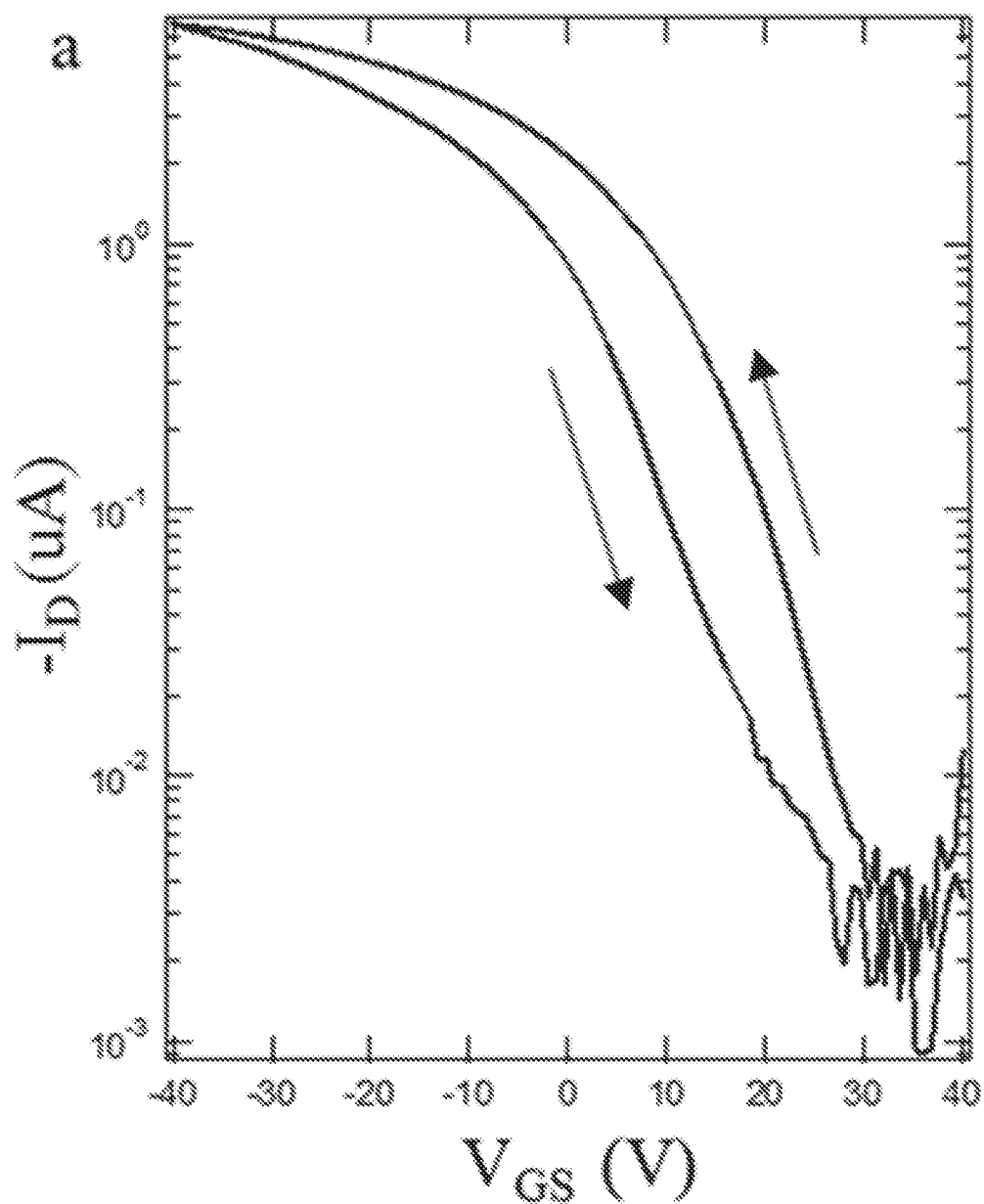
FIG. 31 is a plot of a subthreshold for a printed substrate gated CNT-TFT (lacking a second dielectric layer).
Figure 32:
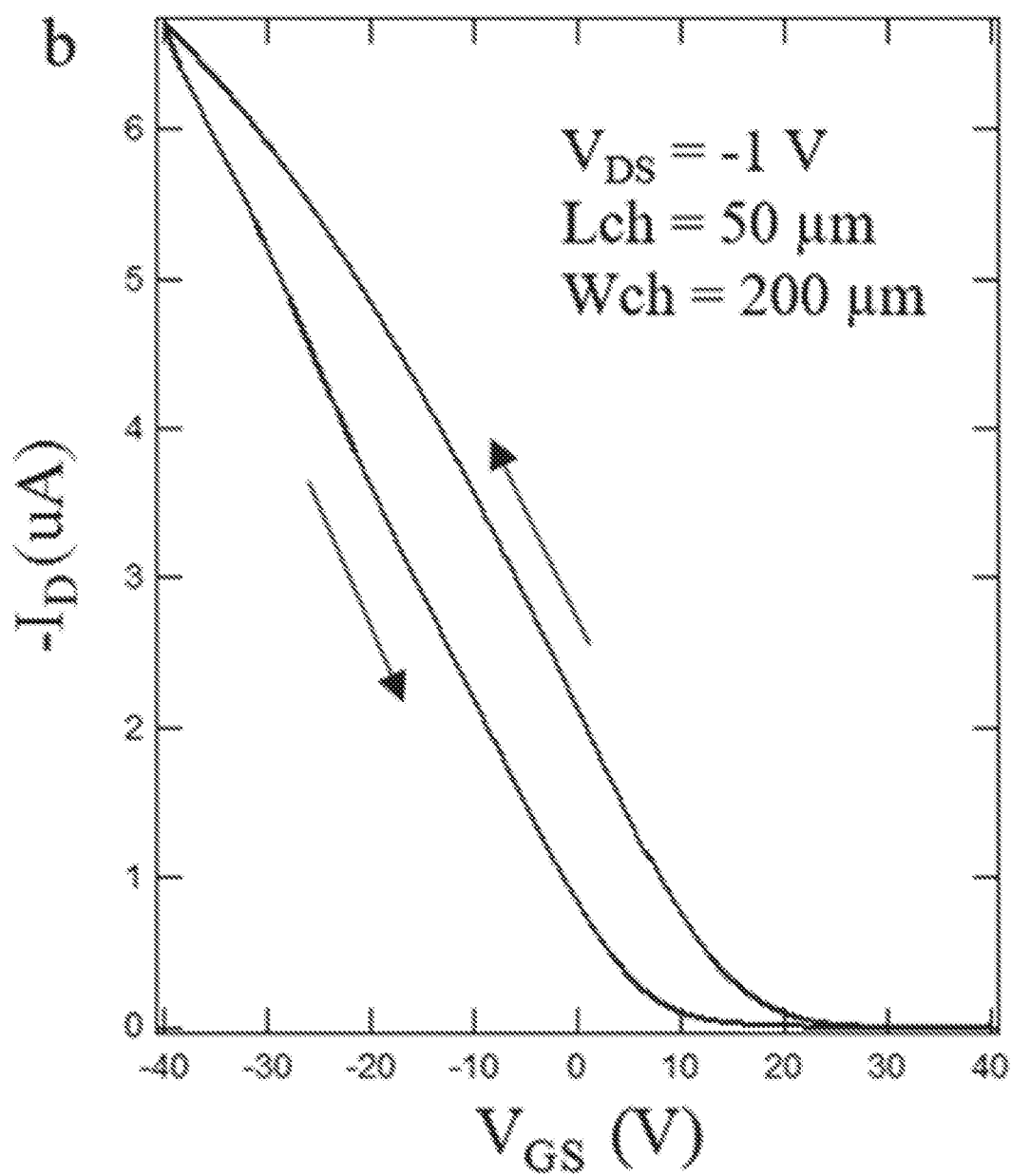
FIG. 32 is a plot of a transfer characteristics for a printed substrate gated CNT-TFT (lacking a second dielectric layer).

The devices were then tested using a device analyzer (B-1500 Semiconductor Parameter Analyzer). The sub-threshold and transfer characteristics of the device are shown in FIG. 31-32. The characteristics of the device will change drastically once the serum or blood is placed on top of the transistor and biological interface layer, but through these preliminary transistor measurements it was possible to rule out that the transistor is either not functional or shorted. The transistor showed relatively good $I_{on}/I_{off}$ ratio of >103, and a high on-current of ≈7 µA or ≈35 µA/mm.

Figure 12:
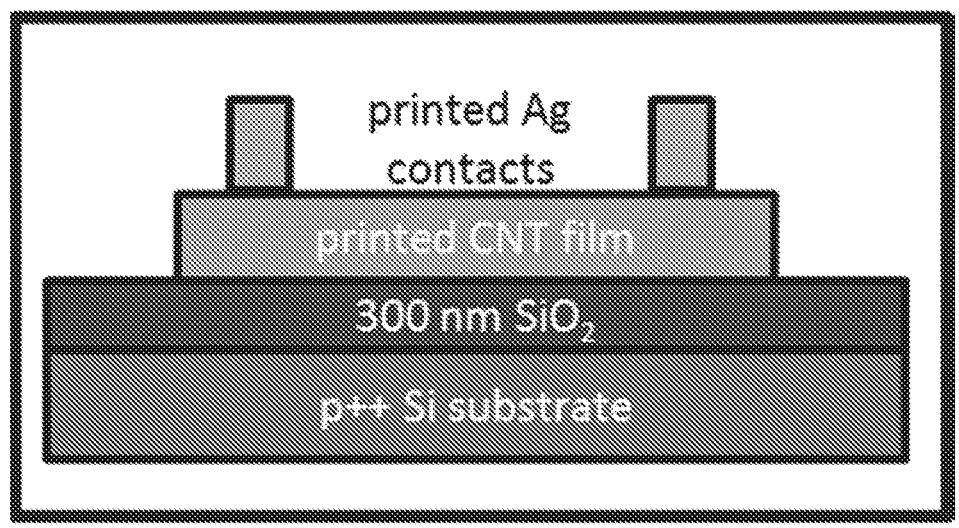
FIG. 12 is a schematic of a sensor that applies Al$_2$O$_3$ via atomic layer deposition (ALD).
Figure 12:
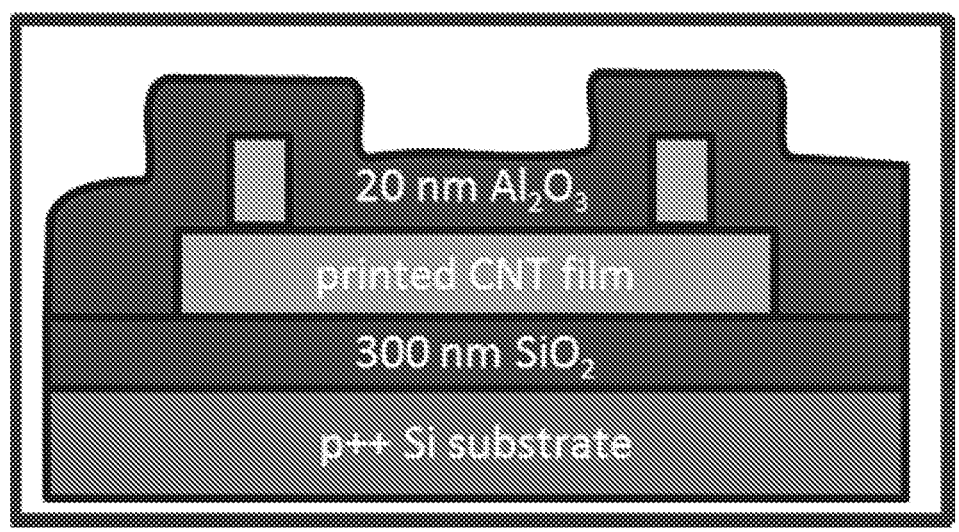
Figure 13:
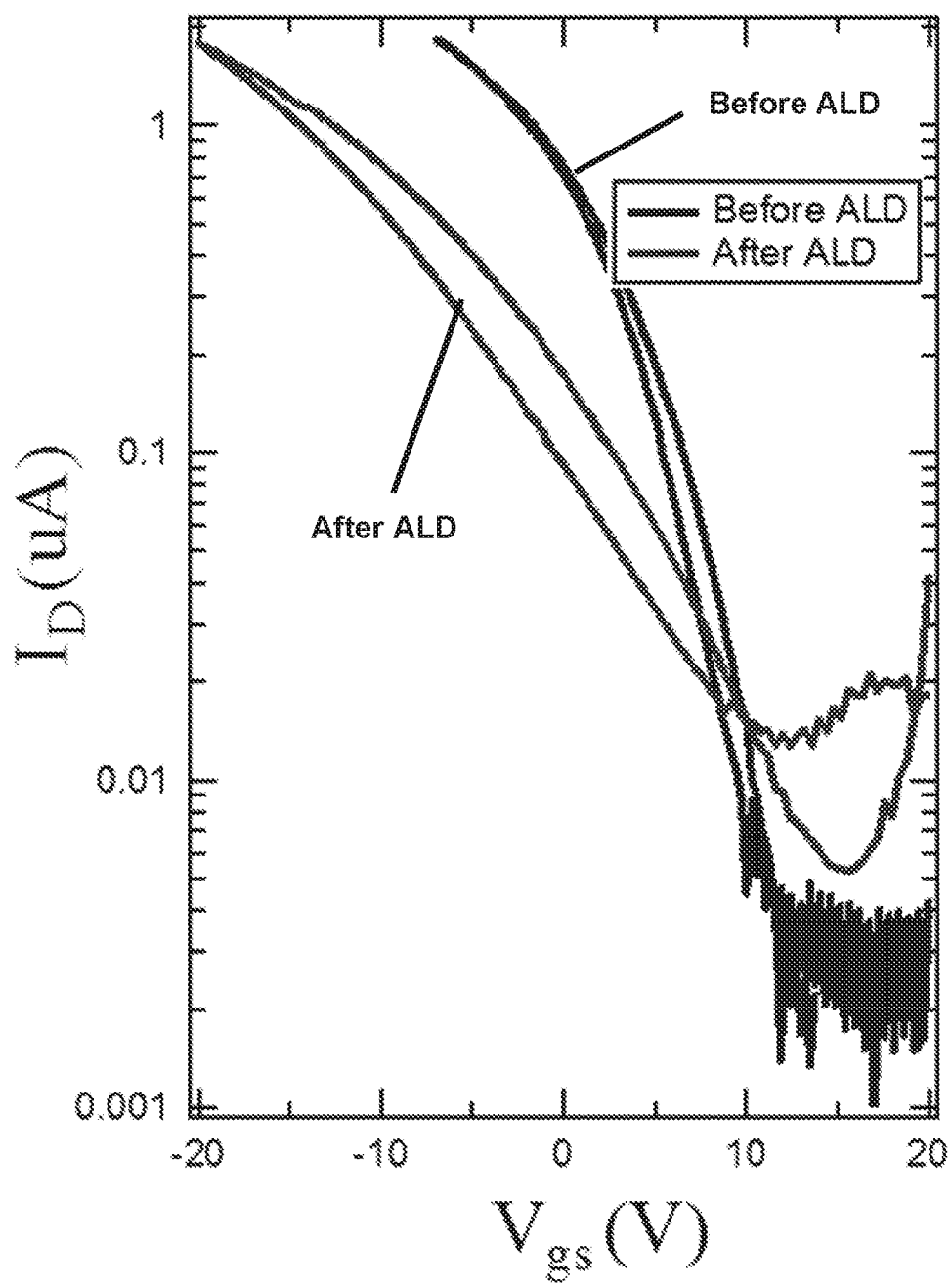
FIG. 13 is a plot of subthreshold curves of a sensor before and after atomic layer deposition of a dielectric layer onto the carbon nanotube channel.
Figure 14:
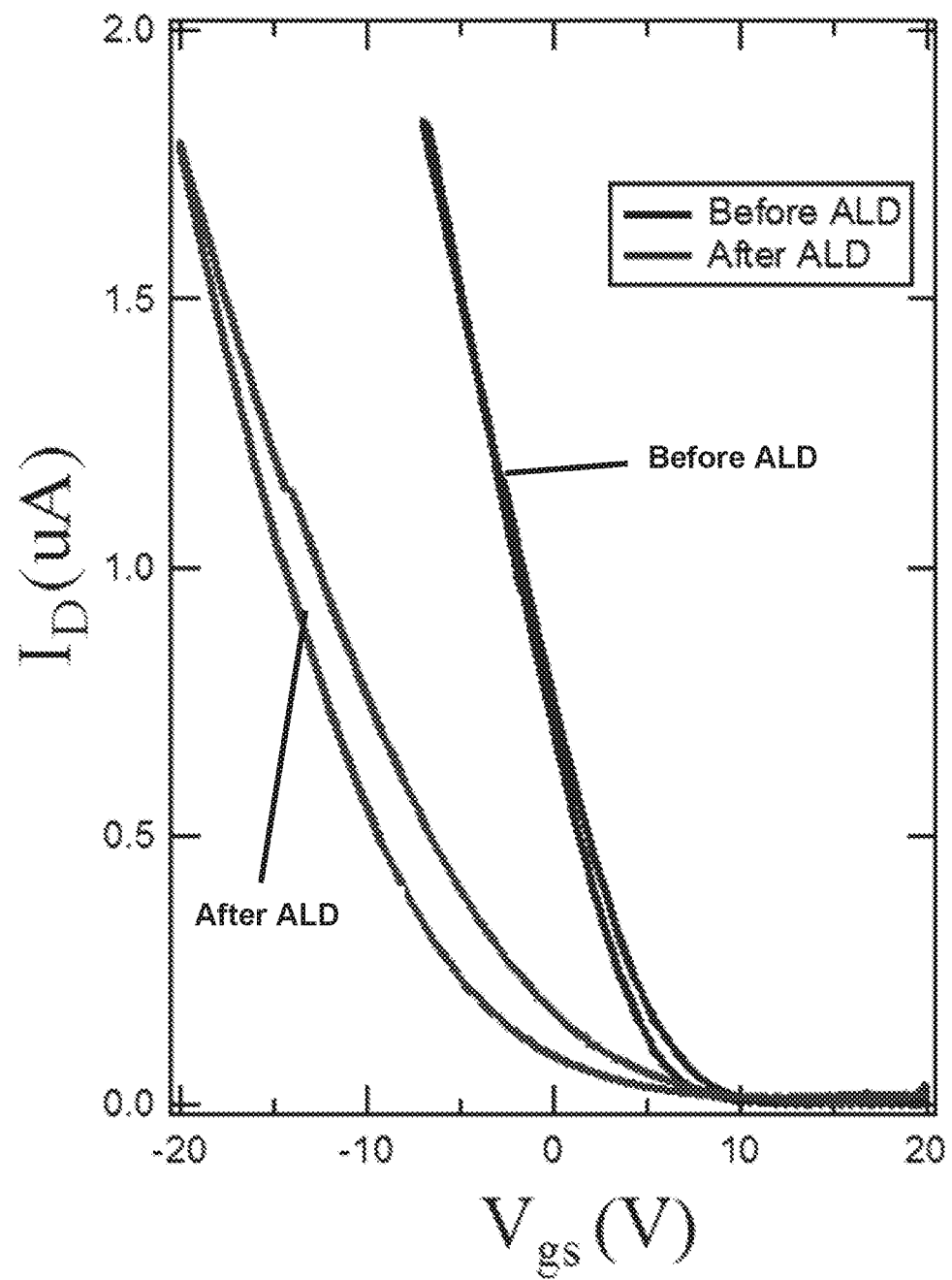
FIG. 14 is a plot of transfer curves of a sensor before and after atomic layer deposition of a dielectric layer onto the carbon nanotube channel.

$Al_2O_3$ Passivated CNT-TFT Biosensor: An embodiment of the devices were encapsulated by an insulating high-k dielectric layer. A 20 nm layer of $Al_2O_3$ was deposited onto the surface of the chip at 120° C. using Kurt J. Lesker custom built ALD system. The ALD involved 234 cycles of alternating trimethylaluminum and $H_2O$ at a growth rate of 0.08544 nm/cycle. (see FIG. 12-14)

Surface-initiated atom transfer radical polymerization of POEGMA: After ALD, samples were immersed in a 10% solution of 3-aminopropyltriethoxysilane (APTES) (Gelest, Inc.; Morrisville, Pa.) in ethanol overnight, and subsequently rinsed with fresh ethanol and then with deionized water. Chips were spun dry at 150 rcf for 5 minutes and then cured in an oven at 120° C. for 2 h. Next, the chips were cooled to room temperature then placed in a dichloromethane solution containing 1% α-bromoisobutyryl bromide (BIB) and 1% triethylamine (TEA) (Sigma Aldrich; St. Louis, Mo.) for 45 min, followed by rinsing in fresh dichloromethane, then ethanol, and then in deionized water. The chips (now functionalized with bromide ATRP initiator) were spun dry 150 rcf for 5 minutes and then stored under ambient conditions. Meanwhile, a solution composed of 350 mL deionized water, 25 mg copper (II) bromide, 50 microliters of 1,1,4,7,10,10-Hexamethyltriethylenetetramine (HMTETA), and 75 grams of inhibitor-free poly(ethylene glycol) methyl ether methacrylate (Mn 300) were degassed by He-sparging for 3 hours. After degassing, under an argon environment, 800 mg of sodium ascorbate was added to the polymerization solution described above and gently stirred for 1 min, at which point the solution changed color from blue to violet. The chips were then placed in this solution for polymerization (without stirring). After allowing polymerization to proceed for 2 hours, chips were rinsed three times with deionized water, then centrifuged at 150 rcf for 6 minutes and allowed to dry under ambient conditions. The thickness of POEGMA brush was determined by reflective-mode ellipsometry.

Figure 21:
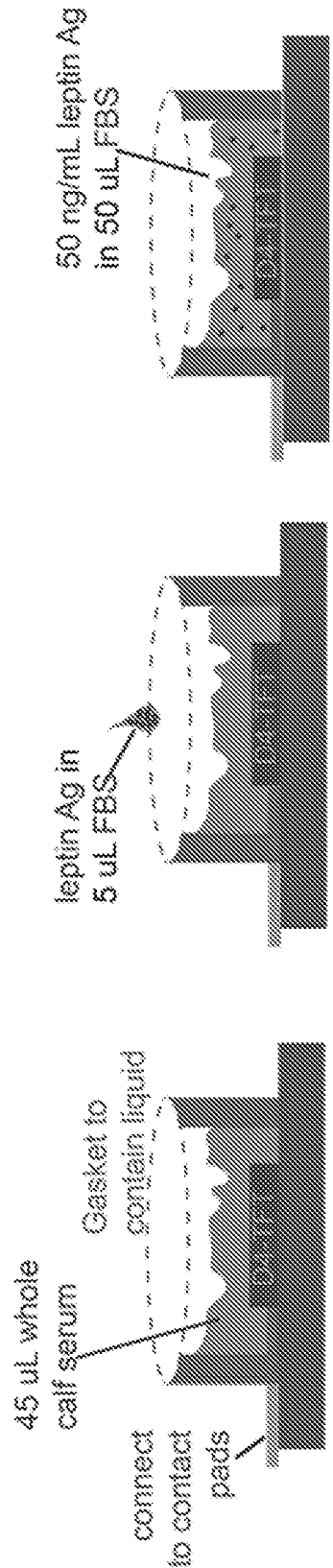
FIG. 21 is a schematic of how the sensors can be used to detect the presence (or absence) of an analyte within a sample.
Figure 28:
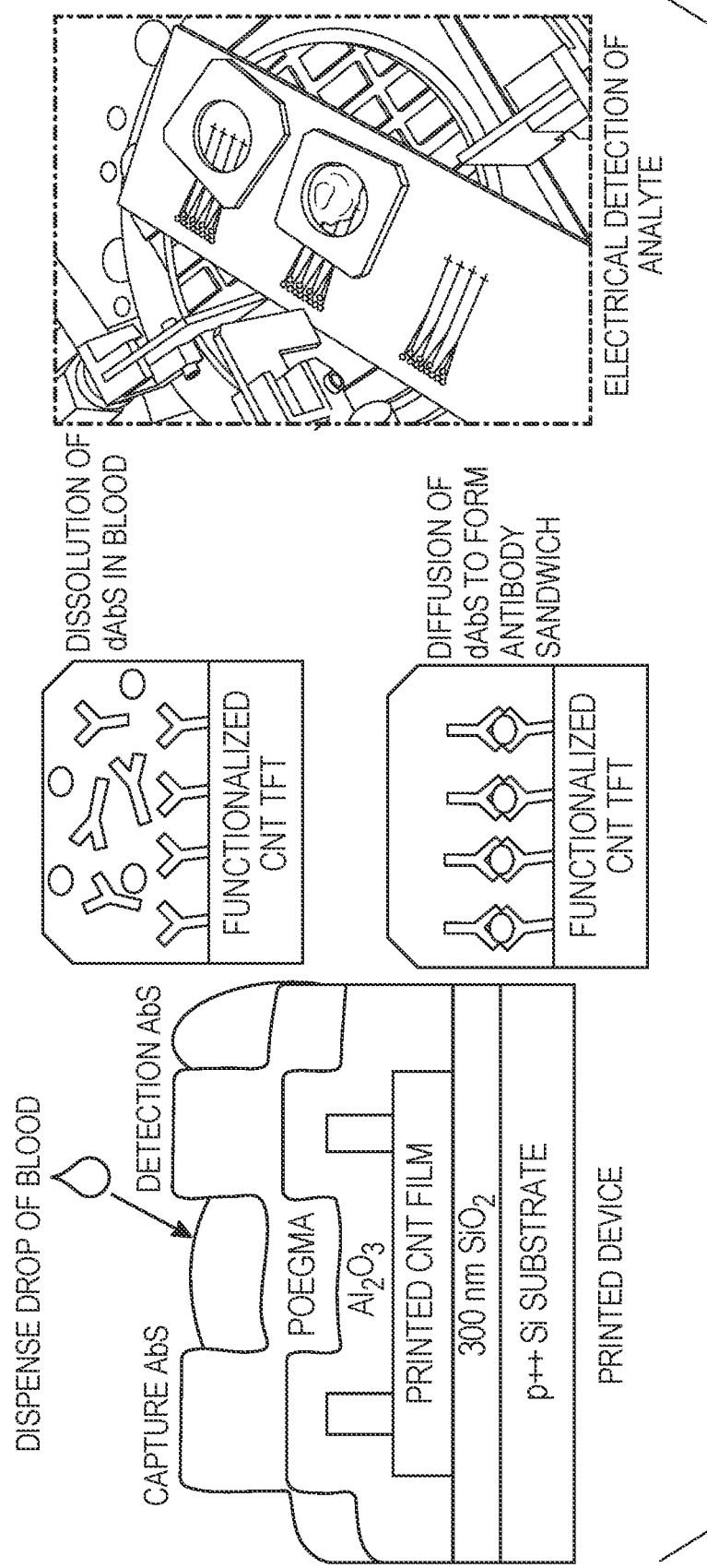
FIG. 28 shows a schematic of a method for using the disclosed sensors to detect the presence (or absence) of an analyte in a sample.
Figure 29:
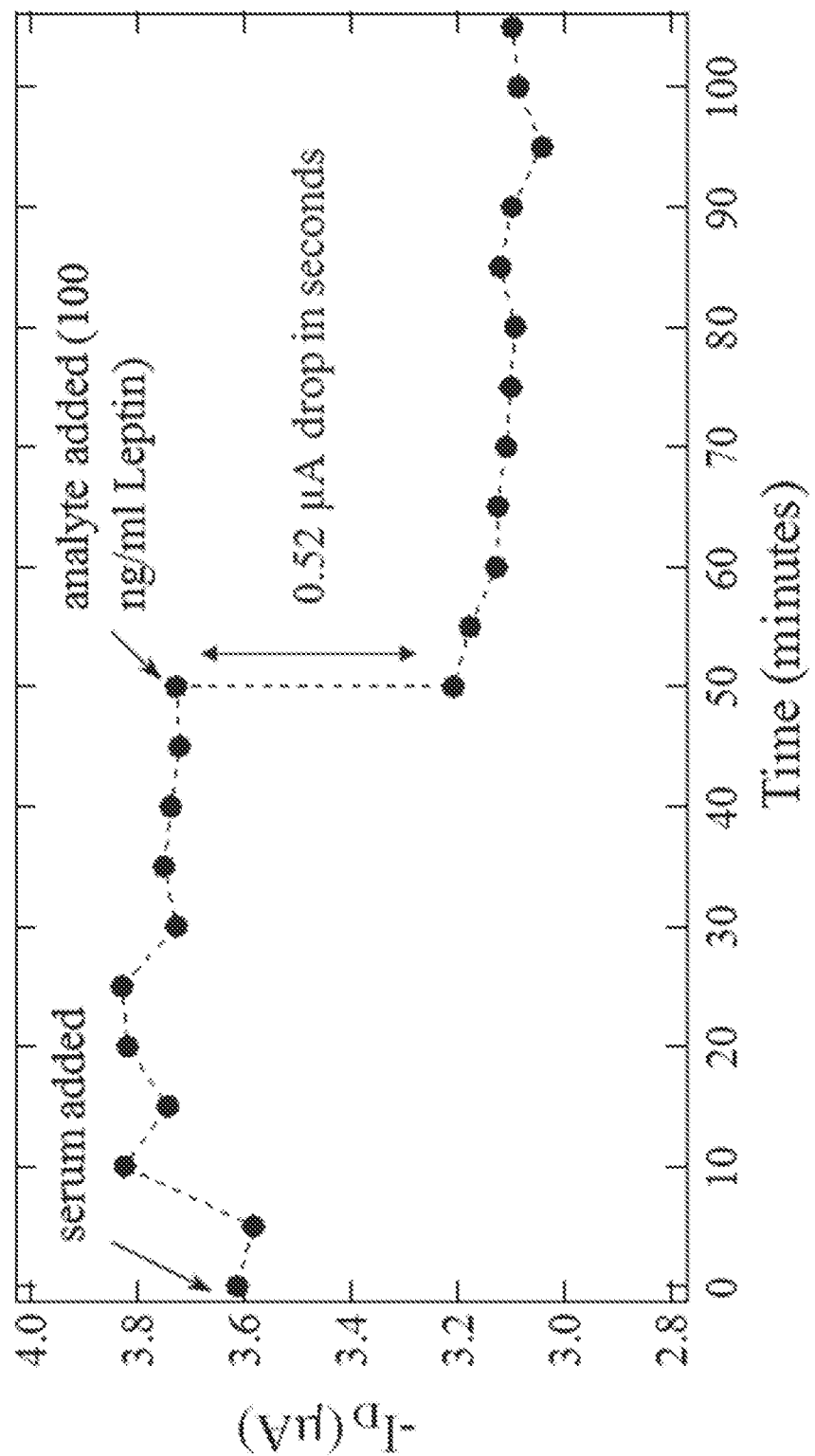
FIG. 29 is a plot showing that the charge from antibodies causes a shift in the threshold voltage (turn-on voltage) and the transconductance of the transistor (where the sensor has a second dielectric layer).

Printing of biological reagents: Next, capture and detection antibodies were printed onto the substrate in order to facilitate specific binding of a target analyte. The sensing mechanism of these devices relies on a conventional sandwich assay, in which capture and detection antibodies both attach to the same analyte at different locations ("epitopes") in effect forming a sandwich. The biosensor targeting the adipocytokine hormone leptin used antibodies purchased from R&D systems—both reagents were printed at concentrations of 1 mg/mL. The first set of printed antibodies (capture antibodies) were printed directly on the channel region. The POEGMA layer noncovalently immobilizes these antibodies and prevented their diffusion, even when a liquid medium was placed on top of the substrate. Next, a second of set of antibodies (detection antibodies) were printed on the perimeter of the channel. The detection antibodies were printed in extreme excess to facilitate their diffusion into the blood/serum in order to react with any present analytes. When blood/serum is added to the system, the detection antibodies diffuse, attach to the analytes, and then as they diffuse to the surface, attach to the capture antibodies that are printed directly onto the CNT channel. A schematic illustrating the sandwich assay with the disclosed sensors is shown in FIGS. 21 and 28.

After the printing of the biologicals was completed, the assay was performed using leptin-spiked fetal bovine serum. 45 µl of bovine serum was first added and $I_d$-$V_{gs}$ sweeps were done to obtain a baseline prior to adding the leptin analyte. Next, the leptin analyte was introduced by adding a highly concentrated 5 µl of bovine serum with leptin to bring the total serum to 50 µl with a leptin concentration of 110 ng/ml. The subthreshold and transfer characteristics taken throughout the test are shown in FIGS. 17-19 and 29.

Results and Discussion

The results from the experiment with the ALD chip provided insight into the sensing mechanism and the transistor operation within a liquid environment. A particularly interesting observation was the significant decrease in subthreshold swing (SS). Before the liquid serum was added the transistor had a typical TFT substrate gated SS of close to 6 V/decade, but with the serum added on top of the transistor the SS was lowered to about 1.5 V/decade. This is perhaps due to the ionic nature of the liquid in effect providing another "gate" on top of the nanotube channel. A mirror charge from the substrate gate would be transported to the ionic liquid and this phenomenon is most likely the cause for the lower SS and also the cause for the increased current. The high off current could be explained by some electron transport through the liquid itself, even when the nanotube channel is "off". Most interestingly however is the decrease in both the threshold voltage and the decrease in channel conductance. The threshold voltage shifts from −0.5 V with just the serum to −0.2 V after 85 minutes of the analyte being in the solution. This suggests a gating effect provided by the antibody sandwich. The antibody sandwich can exhibit a negative charge that is electrostatically "doping" the channel and causing a decrease in the threshold voltage. The change in conductance of the channel could be due to a capacitive effect caused by the antibody sandwich forming a significant layer between the channel and the ionic liquid that is in essence gating the device. Overall, the device passivated by $Al_2O_3$ provided insight into the operation of the sensor, thereby indicating that the antibody sandwich technique is a viable method for detection of leptin analyte using a CNT-TFT biosensor.

Figure 22:
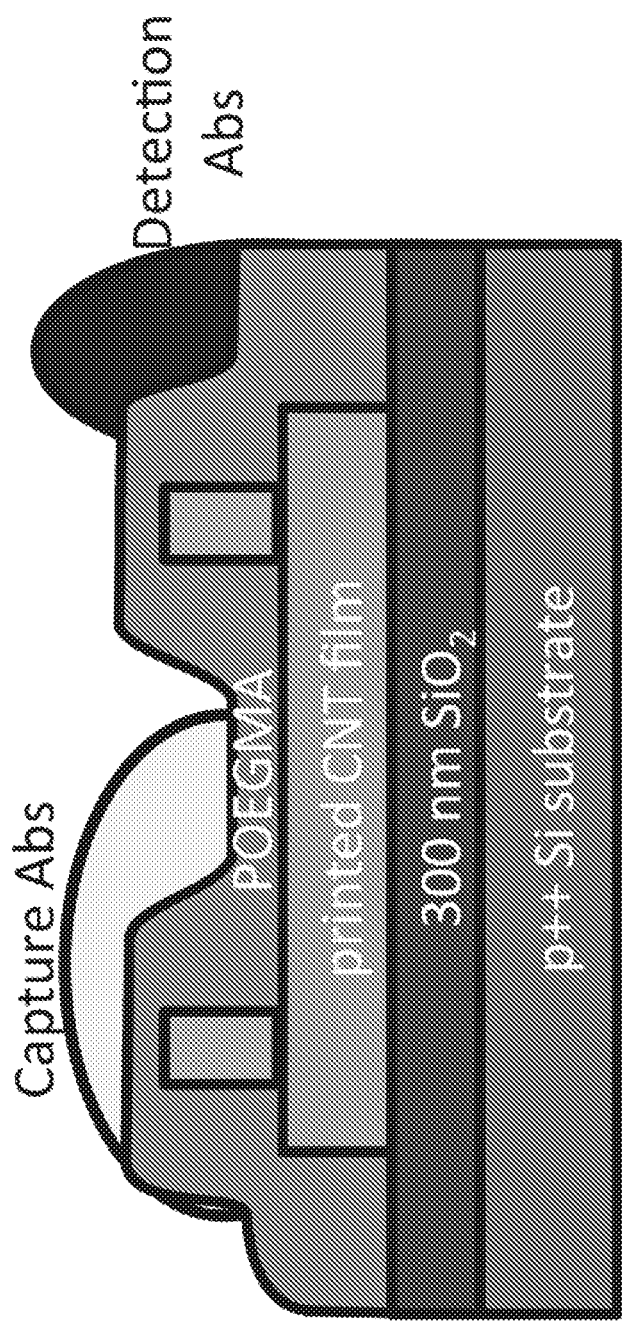
FIG. 22 is a schematic of a sensor that has the non-fouling polymer layer directly contacting the carbon nanotube channel, as well as capture and detection agents printed onto the non-fouling polymer layer.
Figure 24:
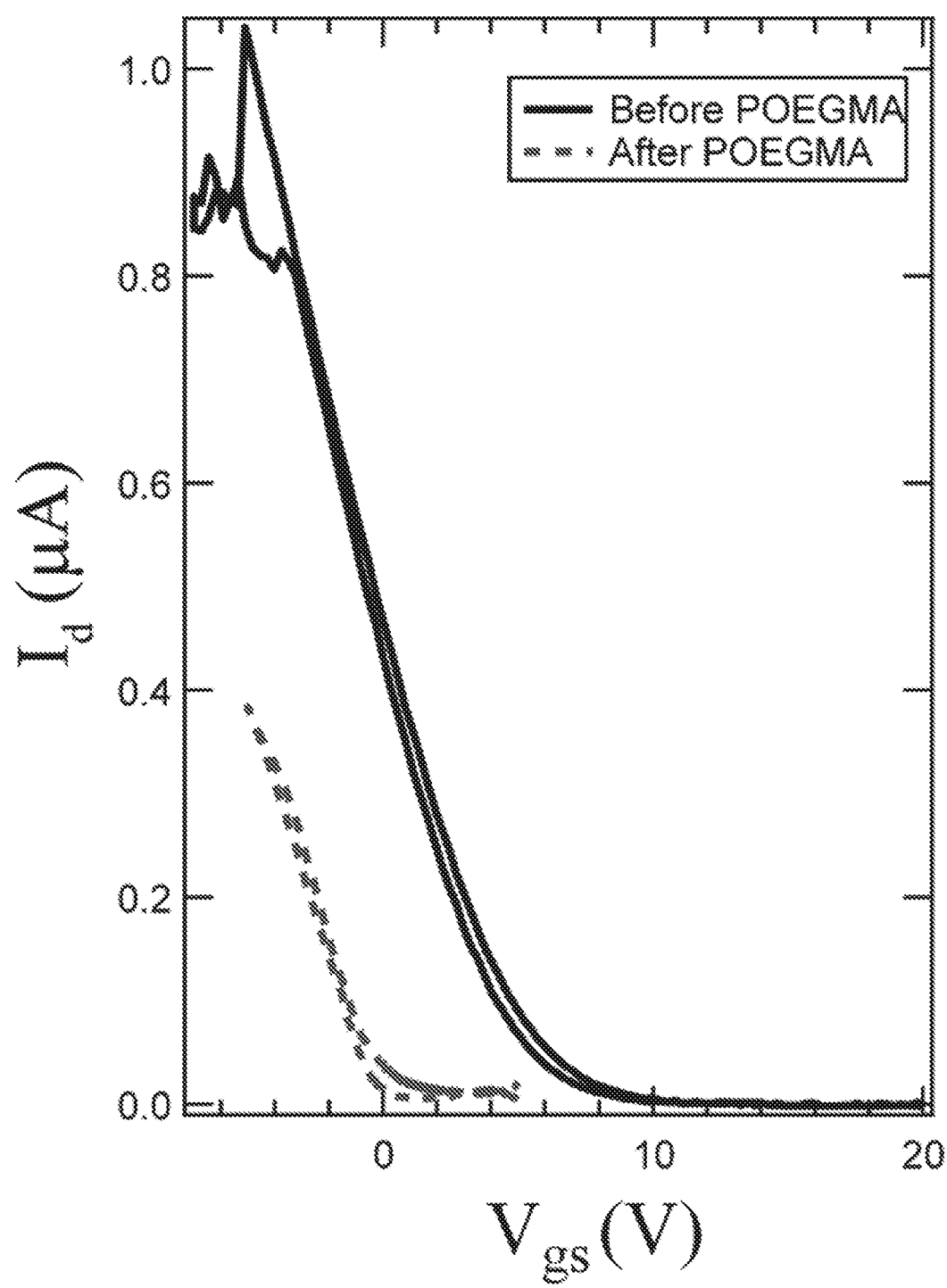
FIG. 24 is a plot of transfer (linear) curves of a sensor (without a second dielectric layer) before and after POEGMA growth.
Figure 25:
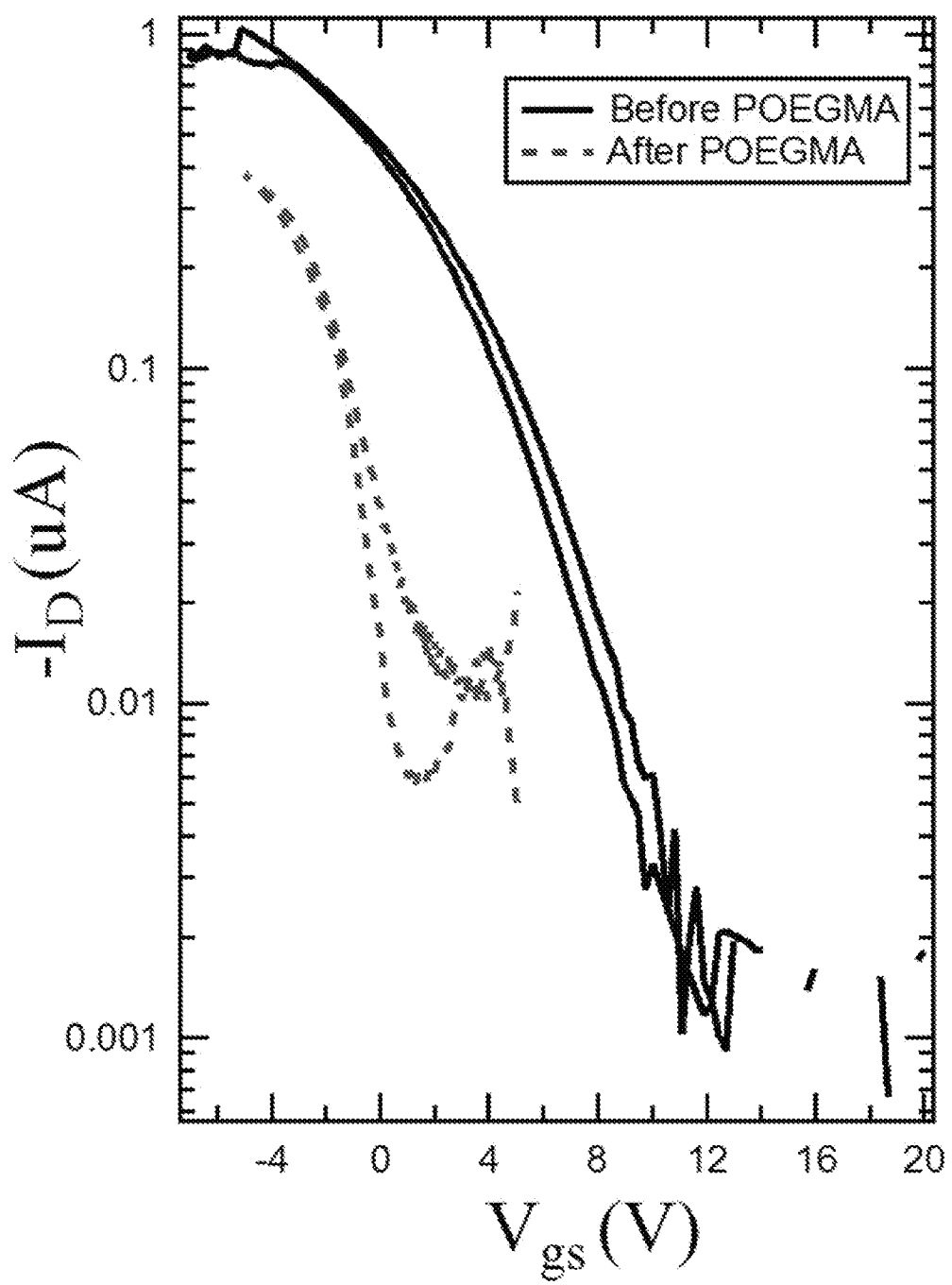
FIG. 25 is a plot of subthreshold (log-scale) curves of a sensor (without a second dielectric layer) before and after POEGMA growth.

As previously mentioned, a second sensor was fabricated without the $Al_2O_3$ layer and with a different initiation method for the POEGMA bio interface layer (see FIG. 22). The device was printed with the exact same conditions previously discussed and the POEGMA was then grown using a method that did not involve DCM solvent—in brief, substrates were immersed in a 10% solution of a silane pre-functionalized with a bromide ATRP initiator (3-Trimethoxysilylpropyl 2-bromo-2-methyl-propionate (Gelest, Inc.; Morrisville, Pa.)), deionized water, and ethanol in a 5:5:90 ratio overnight, and subsequently rinsed with fresh ethanol and then with deionized water. Chips were spun dry at 150 rcf for 5 minutes and then cured in an oven at 120° C. for hour. The bromide-functionalized chips were then processed for POEGMA growth via SI-ATRP in an identical manner as bromide-functionalized chips described in the previous section. The device operation was similar before and after POEGMA growth, except for a shift in threshold voltage and a higher off current (see FIGS. 24 and 25).

Figure 26:
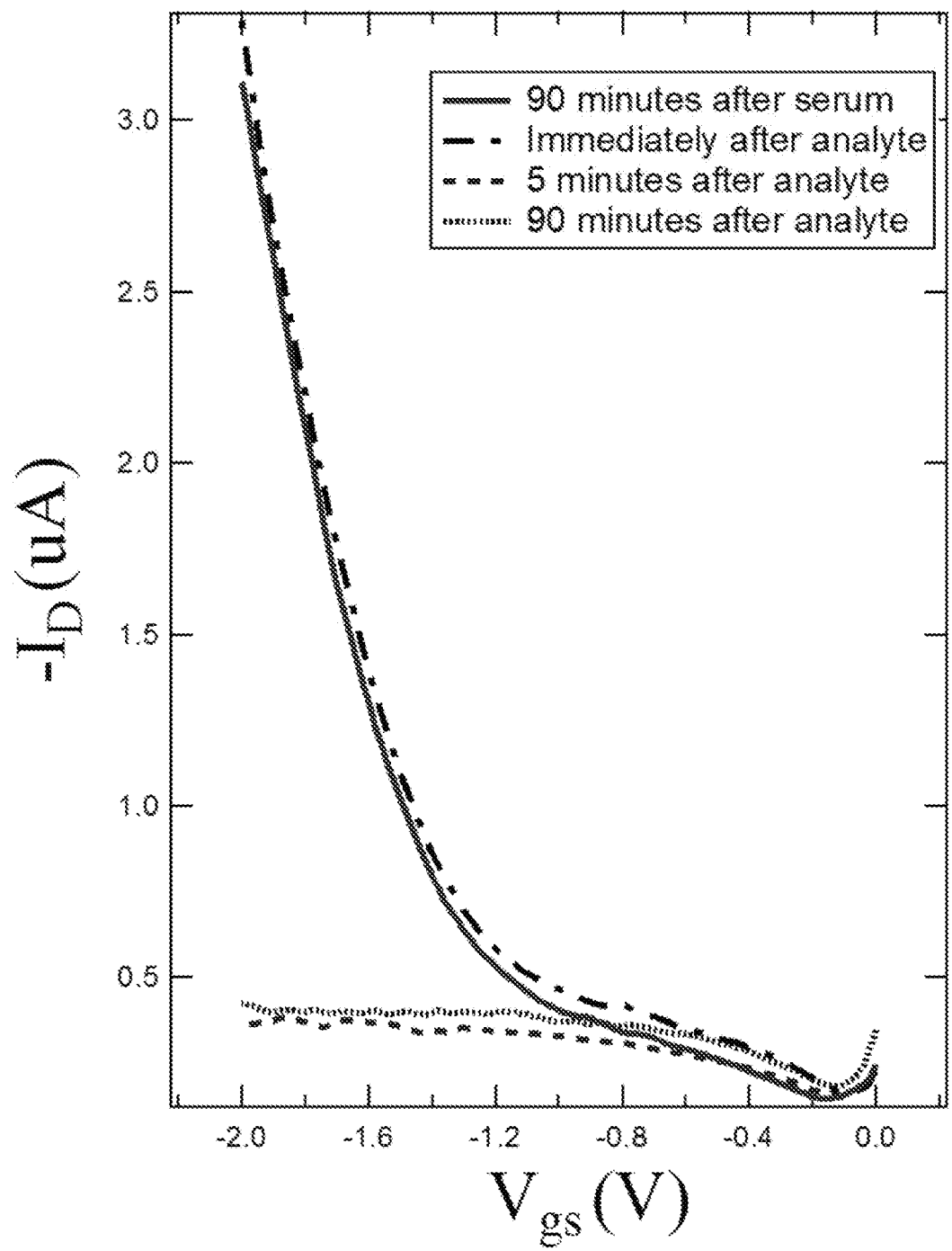
FIG. 26 is a plot of transfer (linear) curves of a sensor (without a second dielectric layer) exposed to a sample including leptin.
Figure 27:
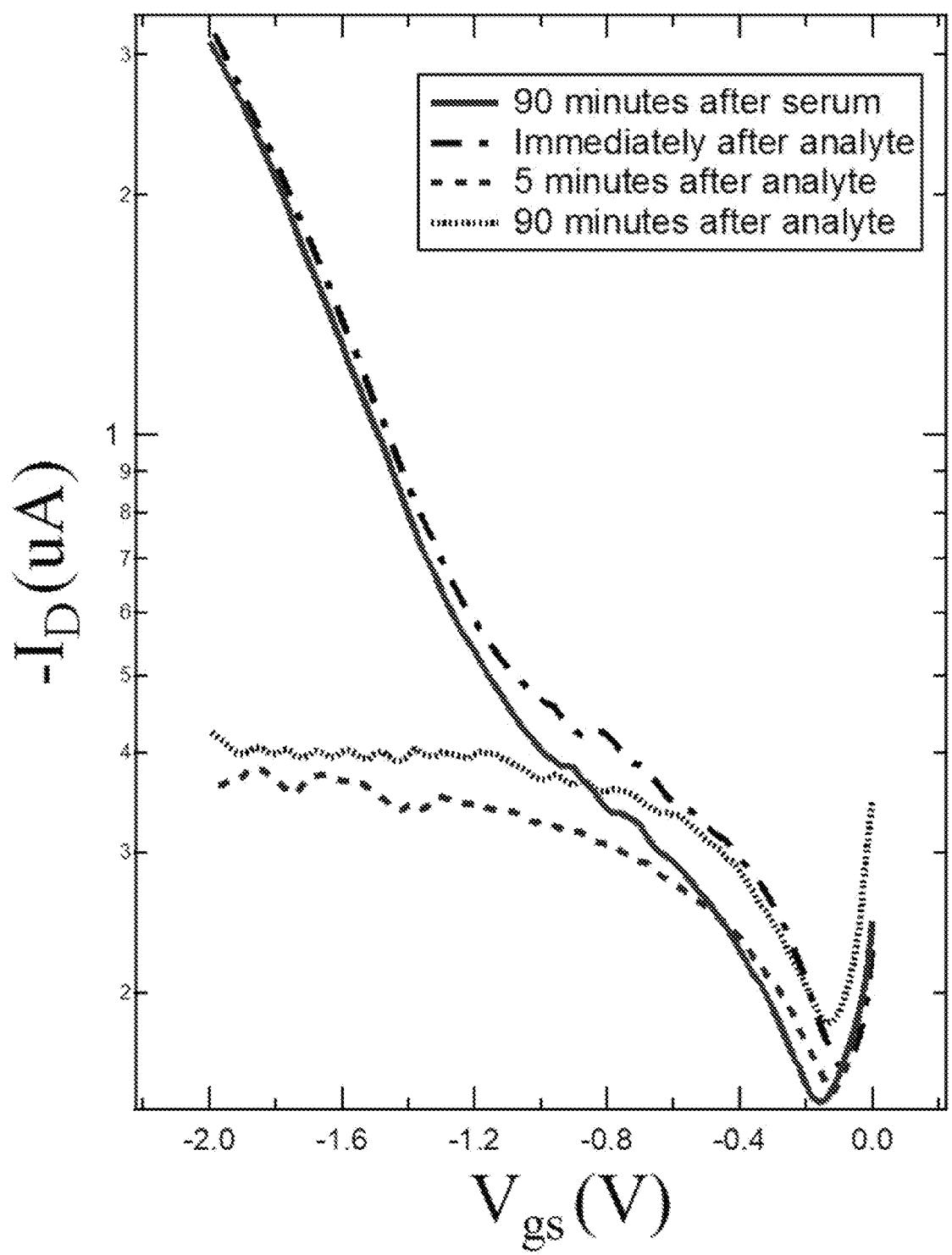
FIG. 27 is a plot of subthreshold (log-scale) curves of a sensor (without a second dielectric layer) exposed to a sample including leptin.

The immunoassay was done in a similar manner as before. This time however, the serum was allowed to sit on the sample for 90 min in order to make sure the effects previously observed were not simply due to the serum sitting on the sample for a long period of time. First 45 µl of bovine serum was added on top of the active area of the transistor within a gasket to protect the contact pads. The serum was left for 90 minutes with $I_d$-$V_{gs}$ curves taken over that time. After 90 minutes, 5 µl of bovine serum containing a high concentration of leptin analyte was added to the solution to create a solution with a total concentration of 50 ng/ml leptin analyte. Also, a glass slide was also placed over the gasket to ensure that there was no evaporation or drying of the serum over the 3-hour test. The results from the test are shown in FIGS. 26 and 27.

This device exhibited similar characteristics to the one that was passivated with $Al_2O_3$, but had a much more extreme response. The operation is most likely due to the same mechanisms as the $Al_2O_3$ device. The threshold voltage shift is not visible within the transfer characteristics due to the extremely low current of the device after analyte addition. However, in the subthreshold plot, the voltage at which the minimum current occurs does shift right from −0.2 V directly before the serum is added to −0.15 V after just 5 minutes of the analyte being in solution. Also, the current is severely diminished after the addition of the analyte. This could be due to the antibody sandwich directly on top of the device is causing a change in capacitance, ultimately decreasing the electrostatic control that the liquid gate has on the surface. It was also noted that the yield based of devices without the ALD layer between the transistor and POEGMA was much lower. This was hypothesized to be attributed to defects or holes within the POEGMA leading to electrical breakdown of the POEGMA dielectric. This ultimately indicates that the ALD layer is key for a more robust and useful sensor, and without such a layer the sensor would likely not be applicable to large-scale production and application.

Figure 33:
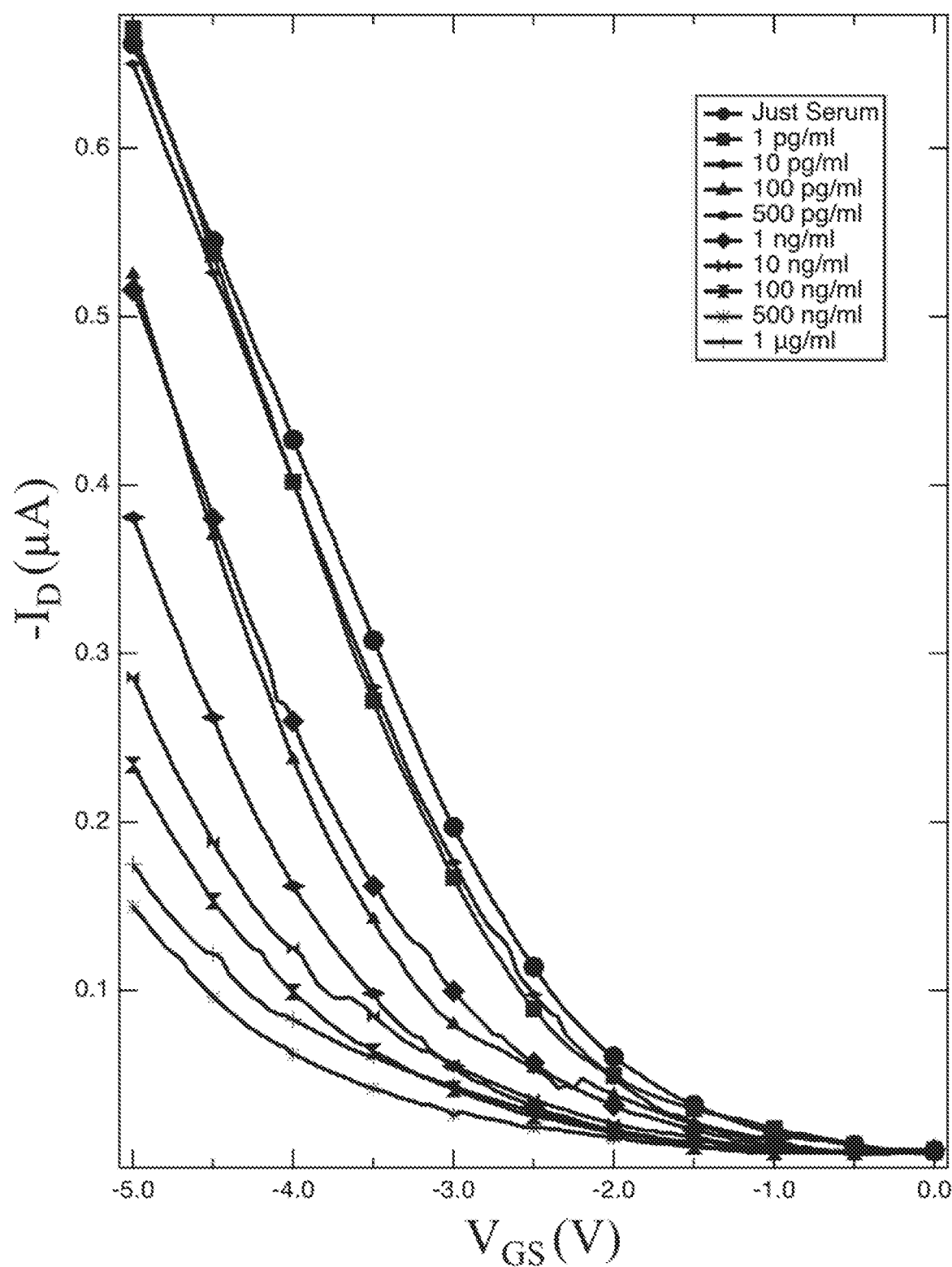
FIG. 33 is a plot of transfer characteristics of a sensor (with a second dielectric layer) following being contacted with a sample that includes leptin.
Figure 34:
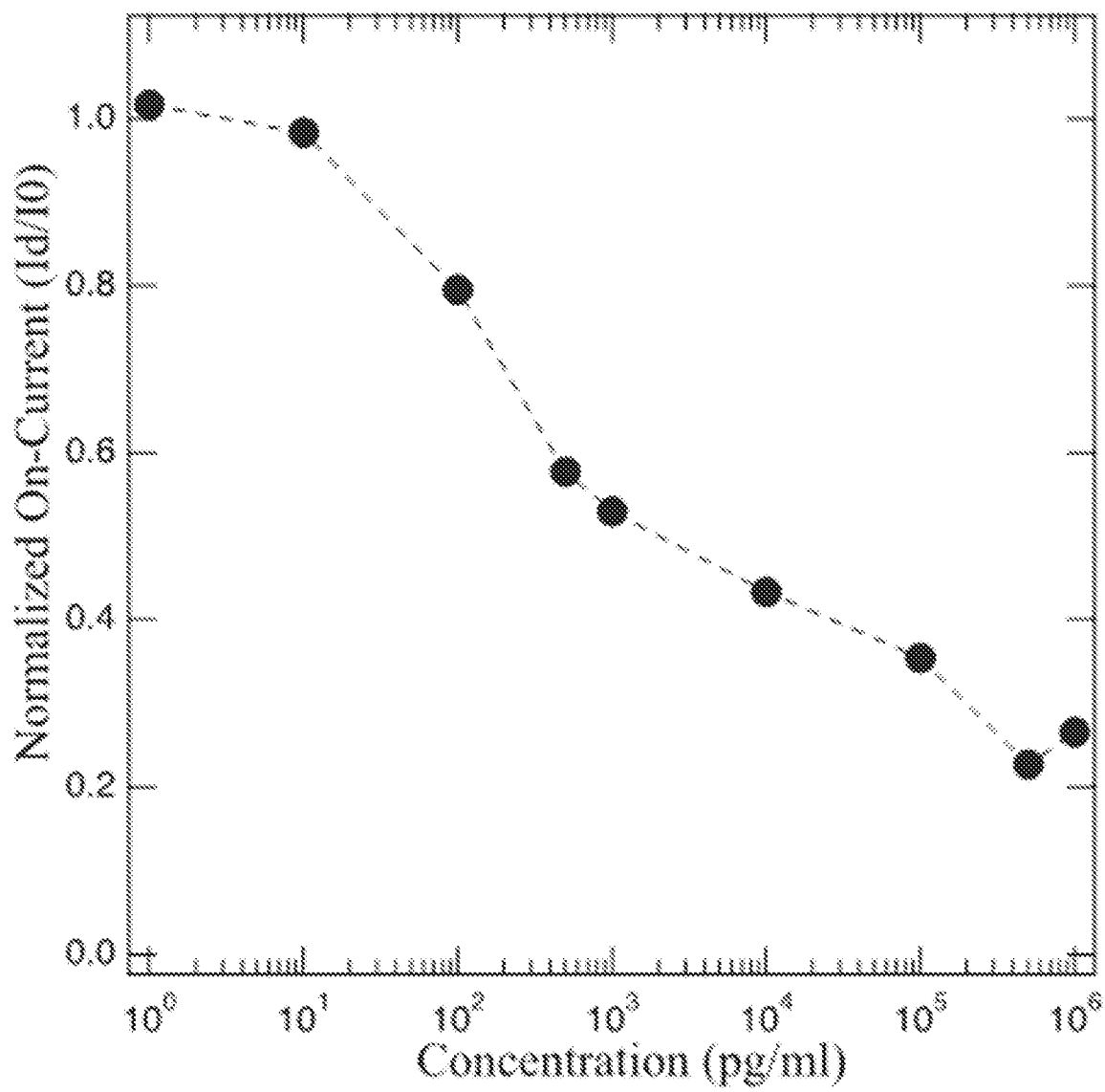
FIG. 34 is a plot of normalized on-current as a function of leptin concentration (where the sensor has a second dielectric layer).

In addition, devices were fabricated in the fashion as described in the printed transistor section above and are an example of the embodiment with the ALD dielectric layer between the CNT channel and the POEGMA bio-interface layer. The only difference is that the ALD $Al_2O_3$ layer was deposited at a slightly thinner, 15 nm thickness. For the testing of the device, the devices were probed using a device analyzer and the dry transistor characteristics were measured. Next, 45 ul of serum was added to the device and allowed to stabilize over approximately 90 minutes. The transistor characteristics were measured after the device stabilized. Next, a 2 uL of leptin-spiked serum (1 pg/mL) was added and the transistor characteristics were taken after a 30 minute stabilization time. This was repeated at each concentration. The On-current v. concentration for each concentration are shown in FIGS. 33 and 34. On-current is defined as the current at a certain operating point (Constant Vgs and Vds) and is normalized to the on-current with no analyte added. The data show a dose-dependent shift in the I-V response as a function of analyte concentration, with an inverse relationship between on-current and concentration.

Figure 35:
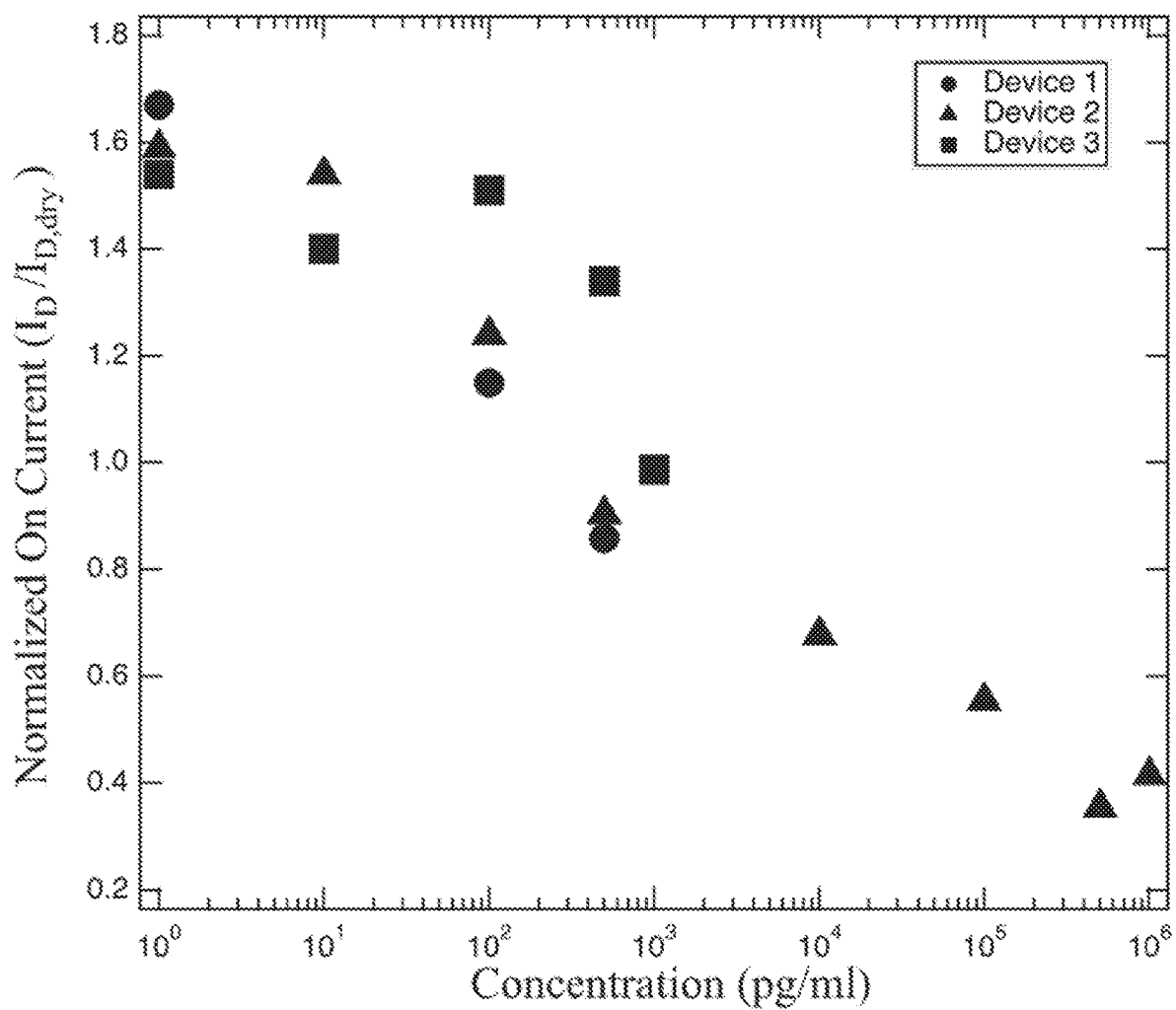
FIG. 35 is a plot of dose response curves normalized to pre-serum on-current across a sensor (with a second dielectric layer), each sensor measured individually.
Figure 36:
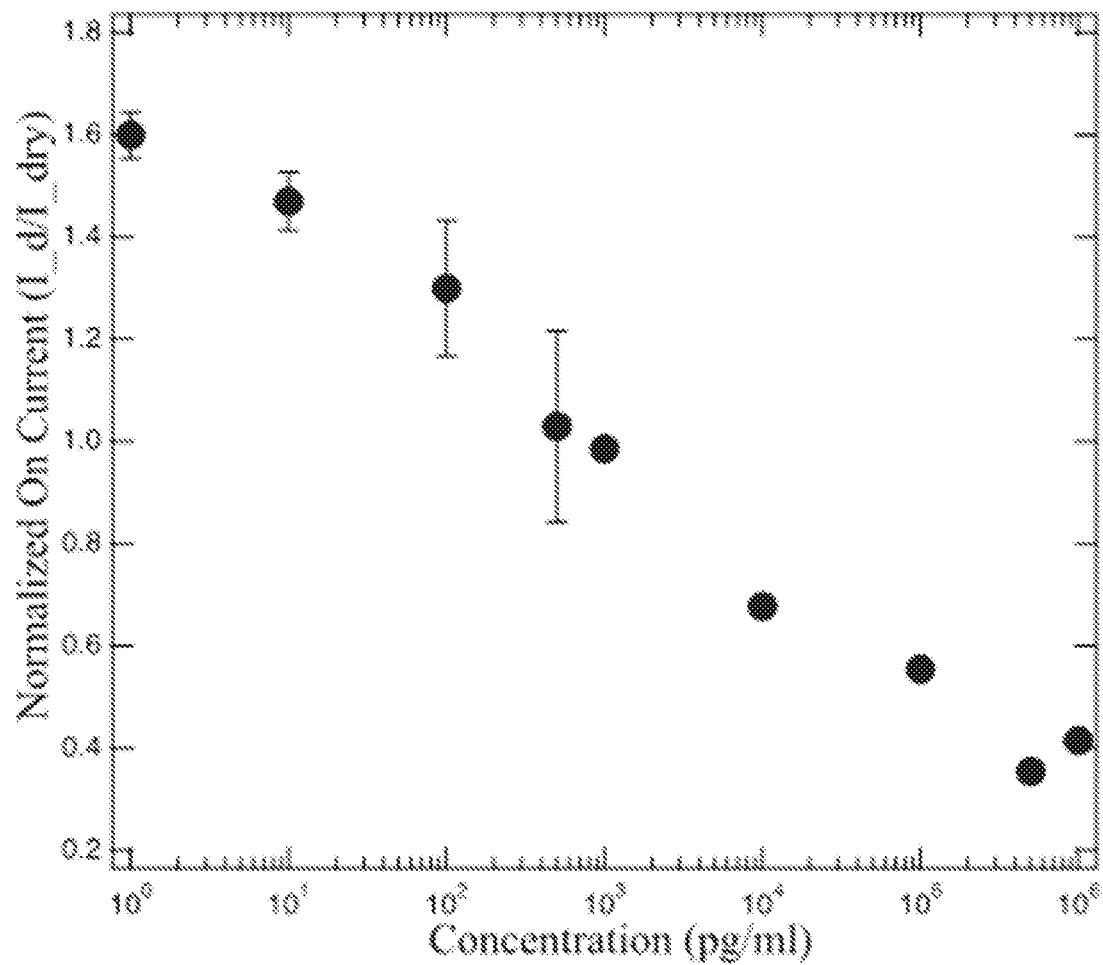
FIG. 36 is a plot of dose response curves normalized to pre-serum on-current across a sensor (with a second dielectric layer), the average of the three sensors shown.

The next step was to normalize the on-current with the dry sensor on-current. This may be crucial in a commercial application so that a patient could directly put their blood onto a sensor without first having to calibrate the sensor with a non-positive serum/blood sample. Three devices were tested and normalized this way and the individual/averaged data are shown in FIGS. 35 and 36. Two of the devices broke down before a full concentration test could be completed. It was observed that normalization of on-current to pre-serum on-current offered a reliable approach towards addressing inter-device variations in transfer characteristics.

Overall, a fully functional, CNT-TFT biosensor has been experimentally verified. An embodiment that consists of a fully printed TFT, encapsulated by an ALD dielectric and a POEGMA biointerface layer has been shown to detect 10 pg/ml Leptin in serum with a detection range of $10^5$. Moreover, the device needs calibration only with the dry transistor characteristics, furthering its viability as a real world, commercial biosensor application.

What is claimed is:

1. A sensor comprising:
   a conductive substrate;
   a first dielectric layer positioned on the conductive substrate;
   a carbon nanotube channel comprising at least one carbon nanotube, the carbon nanotube channel being positioned on the first dielectric layer;
   a source electrode and a drain electrode positioned on the carbon nanotube channel;
   a second dielectric layer positioned on the carbon nanotube channel and having a thickness of from about 10 nm to about 30 nm;
   a non-fouling polymer layer comprising hydroxy terminated poly oligo(ethylene glycol) methyl methacrylate (POEGMA), alkoxy terminated POEGMA, a copolymer of alkoxy-terminated POEGMA and hydroxy-terminated POEGMA, or a combination thereof, the non-fouling polymer layer being positioned on the second dielectric layer and having a thickness of from about 10 nm to about 150 nm;
   at least one capture agent adapted to specifically bind to a target analyte, the capture agent being bound to the non-fouling polymer layer; and
   an electronic circuit configured to measure an electrical property of the carbon nanotube channel.

2. The sensor of claim 1, wherein the conductive substrate comprises silicon, doped silicon, a III-V group semiconductor substrate, a II-VI group semiconductor substrate, an epitaxially grown silicon-germanium substrate, a glass substrate, a quartz substrate, a metal substrate or a plastic substrate.

3. The sensor of claim 1, wherein at least one of the first and second dielectric layers comprise a metal oxide.

4. The sensor of claim 3, wherein the metal oxide comprises $SiO_2$, $Sc_2O_3$, $Al_2O_3$, $TiO_2$, MgO, $In_2O_3$, $SnO_2$, ZnO, ZnMgO, or a combination thereof.

5. The sensor of claim 1, wherein the first dielectric layer has a thickness of from about 10 nm to about 500 nm.

6. The sensor of claim 1, wherein the carbon nanotube channel has a thickness of from about 1 nm to about 10 nm.

7. The sensor of claim 1, wherein the carbon nanotube channel is printed onto the first dielectric layer.

8. The sensor of claim 1, wherein the carbon nanotube channel comprises a plurality of carbon nanotubes.

9. The sensor of claim 1, wherein the carbon nanotube is semi-conducting.

10. The sensor of claim 1, wherein the non-fouling polymer layer has an ethylene glycol repeat unit of greater than or equal to 2.

11. The sensor of claim 1, wherein the non-fouling polymer layer does not directly contact the carbon nanotube channel.

12. The sensor of claim 1, wherein the capture agent is non-covalently bound to the non-fouling polymer layer.

13. The sensor of claim 1, further comprising a detection agent adapted to specifically bind to a target analyte.

14. The sensor of claim 1, wherein at least one of the capture agent and detection agent comprises a nucleic acid, a carbohydrate, a protein or a peptide.

15. The sensor of claim 14, wherein the protein is an antibody.

16. The sensor of claim 15, wherein the antibody is printed onto the non-fouling polymer layer.

17. The sensor of claim 1, wherein the electrical property is selected from the group consisting of resistivity, capacitance, impedance, inductance, and a combination thereof.

18. The sensor of claim 1, wherein the capture agent is separated from the carbon nanotube channel by a distance of greater than 20 nm.

19. The sensor of claim 1, wherein the sensor has a sensitivity of analyte detection of at least 10 pg/ml.

20. A method of detecting the presence or absence of an analyte, the method comprising:
    contacting the sensor of claim 1 with a sample;
    measuring an electrical property of the carbon nanotube channel; and
    determining the presence of the analyte,
    wherein the presence of the analyte is detected through a change in the electrical property of the carbon nanotube channel upon binding of the analyte to the capture agent.

21. The method of claim 20, wherein the sample does not directly contact the carbon nanotube channel.

* * * * *